US012109262B2

(12) United States Patent
Kobayashi et al.

(10) Patent No.: US 12,109,262 B2
(45) Date of Patent: Oct. 8, 2024

(54) METHOD FOR PRODUCING ARTIFICIAL RECOMBINANT ROTAVIRUS

(71) Applicant: Osaka University, Os

(56) References Cited

OTHER PUBLICATIONS

Trask, Shane D. et al., "Dual selection mechanisms drive efficient single-gene reverse genetics for rotavirus" PNAS, Oct. 2010, pp. 18652-18657, vol. 107, No. 43.
International Search Report for PCT/JP2017/034783 dated Dec. 26, 2017.
International Preliminary Report on Patentability for PCT/JP2017/034783 (2017).
Supplementary Partial European Search Report for EP 17856149 dated Mar. 27, 2020.
Martin, Davy et al., "Structural Organisation of the Rotavirus Nonstructural Protein NSP5" J. Mol. Biol., 2011, pp. 209-221, vol. 413.
Trask, S.D. et al., "Dual selection mechanisms drive efficient single-gene reverse genetics for rotavirus" Proceedings of the National Academy of Sciences, Oct. 2010, pp. 18652-18657, vol. 107, No. 43.
European Search Report for EP 23187345 dated Mar. 21, 2024.

METHOD FOR PRODUCING ARTIFICIAL RECOMBINANT ROTAVIRUS

CROSS REFERENCE TO RELATED APPLICATIONS

This application is a divisional application of U.S. patent application Ser. No. 16/336,735, filed on Mar. 26, 2019, which is the U.S. National Phase application of PCT International Application No. PCT/JP2017/034783, filed on Sep. 26, 2017, designating the United States of America and published in the Japanese language, which is an International Application of and claims the benefit of priority to Japanese Patent Application No. 2016-188881, filed on Sep. 27, 2016 and Japanese Patent Application No. 2017-068323, filed on Mar. 30, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-IWAT007-003D1.txt, the date of creation of the ASCII text file is Jun. 3, 2022, and the size of the ASCII text file is 75 KB.

TECHNICAL FIELD

The present invention relates to a method for producing an artificial recombinant virus of the family Reoviridae, particularly to a method for producing an artificial recombinant rotavirus.

BACKGROUND ART

Rotaviruses, members of the family Reoviridae, are known as a causative virus of infant diarrhea. Infants aged from 6 months to 2 years are at high risk of rotavirus infection and rotavirus disease development. Almost all children will have been infected with rotaviruses by the age of five. Vaccines against rotaviruses are in practical use and their preventive efficacy has been proven in practice. In the meanwhile, next-generation rotavirus vaccines that are less expensive and have highly preventive effect are under research and development.

Reverse genetics (RG) systems that allow artificial virus production have been established for a wide variety of RNA viruses and have greatly contributed to the progress of virological basic research and applied research such as viral vector development and vaccine vector development. However, the development of RG systems for Reoviridae viruses, which have a 10 to 12 segmented double-stranded RNA (dsRNA) genome, lags behind that of RG systems for other RNA viruses due to the complexity of their segmented genome.

Various RG systems for Reoviridae viruses have been developed so far. For bluetongue virus and African horse sickness virus in the genus *Orbivirus*, RNA-based RG systems have been developed, and these systems allow recombinant virus production based on the introduction of viral RNA into cells (Non Patent Literature 1 and 2). For Mammalian orthoreovirus in the genus *Orthoreovirus*, an entirely DNA-based RG system using cDNA has been developed (Non Patent Literature 3). For rotaviruses in the genus *Rotavirus*, partially DNA-based RG systems using a helper virus have been reported (Non Patent Literature 4 and 5). However, the helper virus-dependent RG systems have disadvantages in that a potent means of separating the virus of interest from the helper virus is required; that mutation can be introduced only into limited types of segment genes (VP4 gene, NSP2 gene); and that production efficiency is low. Under such circumstances, the development of complete RG systems that allow rotavirus production based on the introduction of only cDNA or RNA without using a helper virus is eagerly anticipated.

CITATION LIST

Non Patent Literature

Non Patent Literature 1

Boyce, M., Celma, C. C., and Roy, P., Development of reverse genetics systems for bluetongue virus: recovery of infectious virus from synthetic RNA transcripts, J Virol 82:8339-8348, 2008.

Non Patent Literature 2

Kaname Y, Celma C C, Kanai Y, Roy P., Recovery of African horse sickness virus from synthetic RNA, J Gen Virol 94:2259-2265, 2013.

Non Patent Literature 3

Kobayashi, T, Antar, A A R, Boehme, K W, Danthi, P, Eby, E A, Guglielmi, K M, Holm, G H, Johnson, E M, Maginnis, M S, Naik, S, Skelton, W B, Wetzel, J D, Wilson, G J, Chappell, J D, and Dermody, T S, A plasmid-based reverse genetics system for animal double-stranded RNA viruses. Cell Host Microbe 1:147-157, 2007.

Non Patent Literature 4

Komoto, S, Sasaki, J, and Taniguchi, K, Reverse genetics system for introduction of site-specific mutations into the double-stranded RNA genome of infectious rotavirus. Proc Natl Acad Sci USA 103:4646-4651, 2006.

Non Patent Literature 5

Trask S D, Taraporewala Z E, Boehme T S, Dermody T S, Patton J T, Dual selection mechanisms drive efficient single-gene reverse genetics for rotavirus. Proc Natl Acad Sci USA 107:18652-18657 2010.

SUMMARY OF INVENTION

Technical Problem

An object of the present invention is to provide a method for producing an artificial recombinant virus of the family Reoviridae using an improved reverse genetics system for Reoviridae viruses, which method is more efficient in virus production as compared with conventional ones. Another object of the present invention is to provide a method for producing an artificial recombinant rotavirus without using a helper virus. A yet another object of the present invention is to provide an artificial recombinant rotavirus as a vaccine candidate, the artificial recombinant rotavirus having a mutation introduced in a viral genome segment.

Solution to Problem

The present invention includes the following to achieve the above-mentioned objects.

[1] A method for producing an artificial recombinant virus of the family Reoviridae, the method comprising the steps of:
(1) introducing a FAST protein expression vector and/or a capping enzyme expression vector into host cells;
(2) introducing a vector containing expression cassettes for individual RNA genome segments of a virus or introducing a set of single-stranded RNA transcripts from the expression cassettes into host cells; and
(3) culturing the host cells.

[2] The method according to the above [1], wherein the artificial recombinant virus has a mutation introduced in at least one of the RNA genome segments and/or a foreign gene inserted in at least one of the RNA genome segments.

[3] The method according to the above [1] or [2], wherein the FAST protein is at least one kind selected from Nelson Bay reovirus p10, Avian reovirus p10, Broome reovirus p13, Reptilian reovirus p14, Baboon reovirus p15, grass carp reovirus p16 and Atlantic salmon reovirus p22.

[4] The method according to any one of the above [1] to [3], wherein the capping enzyme is a capping enzyme of a DNA or RNA virus which replicates in the cytoplasm of host cells.

[4-1] The method according to any one of the above [1] to [3], wherein the capping enzyme is a capping enzyme of a virus of the family Poxviridae.

[5] The method according to any one of the above [1] to [4], wherein the expression cassette for an RNA genome segment comprises an RNA polymerase promoter, a DNA encoding the RNA genome segment and a DNA encoding a self-cleaving ribozyme.

[6] The method according to the above [5], wherein the RNA polymerase promoter is T7 promoter, and the host cells are recombinant T7 RNA polymerase-expressing cells.

[7] The method according to the above [5] or [6], wherein the ribozyme is a hepatitis D virus ribozyme.

[8] The method according to any one of the above [1] to [7], wherein the host cells are co-cultured with highly virus-susceptible cells.

[9] The method according to any one of the above [1] to [8], wherein the artificial recombinant virus of the family Reoviridae is an artificial recombinant rotavirus.

[10] The method according to the above [9], comprising overexpressing a rotavirus NSP2 gene product and/or a rotavirus NSP5 gene product in the host cells.

[11] The method according to the above [9] or [10], wherein the artificial recombinant rotavirus expresses a foreign gene, and wherein a vector containing an expression cassette for an RNA genome segment encoding NSP1 which cassette has an insertion of the foreign gene in an NSP1 gene and a 100- to 1550-base deletion in the NSP1 gene is used instead of a vector containing an expression cassette for an RNA genome segment encoding NSP1.

[12] A method for promoting viral replication, comprising infecting host cells expressing a FAST protein with a virus and culturing the host cells.

[13] The method according to the above [12], wherein the FAST protein is at least one kind selected from Nelson Bay reovirus p10, Avian reovirus p10, Broome reovirus p13, Reptilian reovirus p14, Baboon reovirus p15, grass carp reovirus p16 and Atlantic salmon reovirus p22.

[14] An artificial recombinant rotavirus having a mutation resulting in functional suppression of at least one selected from NSP1, NSP3 and NSP4.

[15] An artificial recombinant rotavirus expressing a foreign gene.

[16] An artificial recombinant reassortant rotavirus.

[17] A vaccine comprising the artificial recombinant rotavirus according to any one of the above [14] to [16].

[18] A method for producing an artificial recombinant rotavirus, comprising introducing a vector containing expression cassettes for 11 individual RNA genome segments of a rotavirus or introducing a set of 11 single-stranded RNA transcripts from the expression cassettes into host cells expressing neither a FAST protein nor a capping enzyme, and culturing the host cells.

[19] The method according to the above [18], comprising overexpressing a rotavirus NSP2 gene product and/or a rotavirus NSP5 gene product in the host cells, and culturing the host cells.

[20] A method for producing an artificial recombinant virus of the family Reoviridae, the method comprising introducing a vector containing expression cassettes for individual RNA genome segments of a virus or introducing a set of single-stranded RNA transcripts from the expression cassettes into host cells;
overexpressing, in the host cells, a gene product involved in the formation of viral inclusion bodies in infected cells; and
culturing the host cells.

Advantageous Effects of Invention

The present invention provides a method for producing an artificial recombinant virus of the family Reoviridae using a reverse genetics system that allows more efficient artificial recombinant virus production as compared with conventional ones. Also provided is a method for producing an artificial recombinant rotavirus without using a helper virus, which method has not been available so far. Also provided is an artificial recombinant rotavirus as a vaccine candidate, the artificial recombinant rotavirus having a mutation introduced in a viral genome segment.

DESCRIPTION OF EMBODIMENTS

Figures 1, 2:
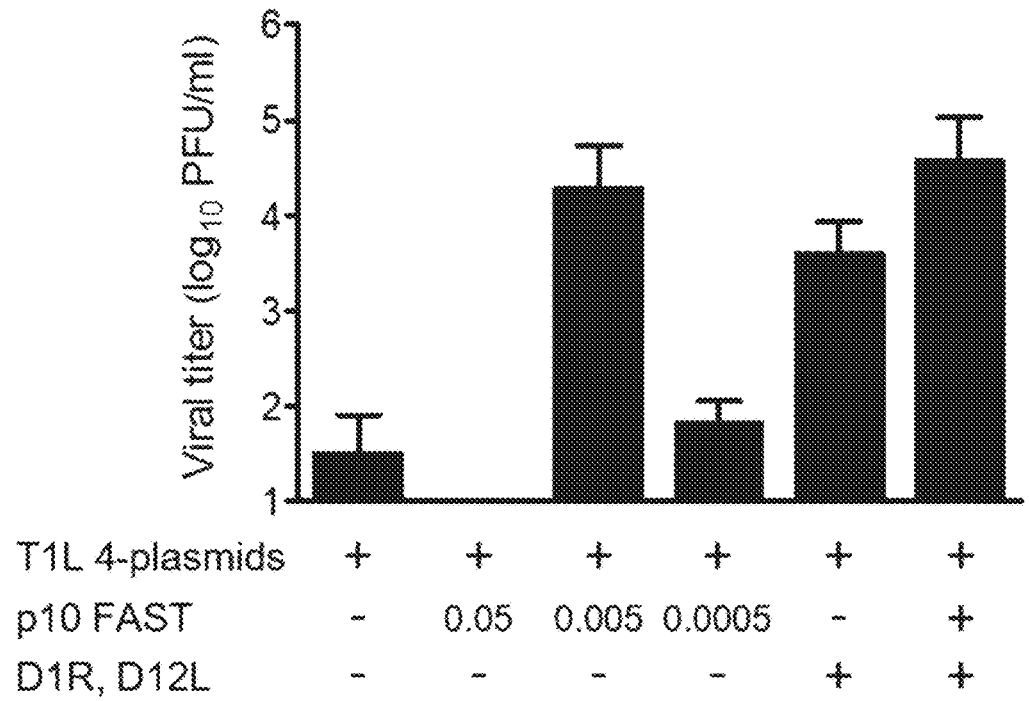
FIG. 1 graphically illustrates the results of the enhancement effect on the efficiency of artificial recombinant virus production using a Mammalian orthoreovirus reverse genetics system by co-expression with a FAST protein and/or a capping enzyme in host cells.
FIG. 2 shows the mutation sites of plasmids having a marker mutation(s) used for artificial recombinant rotavirus production.

Method for Producing an Artificial Recombinant Virus

The present invention provides a method for producing an artificial recombinant virus of the family Reoviridae (hereinafter, referred to as the "production method of the present invention"). The production method of the present invention comprises the steps of:
(1) introducing a FAST protein expression vector and/or a capping enzyme expression vector into host cells;
(2) introducing a vector containing expression cassettes for individual RNA genome segments of a virus or introducing a set of single-stranded RNA transcripts from the expression cassettes into host cells; and
(3) culturing the host cells.

The viruses in the family Reoviridae possess a linear double-stranded RNA (dsRNA) genome consisting of 10 to 12 segments and have an icosahedral virion of 60 to 80 nm in diameter. The viruses in the family Reoviridae include members of the genus *Orthoreovirus* such as Mammalian orthoreovirus, Nelson Bay reovirus and Avian reovirus; members of the genus *Orbivirus* such as African horse sickness virus and bluetongue virus; members of the genus *Rotavirus* such as rotaviruses; members of the genus *Coltivirus* such as Colorado tick fever virus; members of the genus *Aquareovirus* such as Aquareovirus A; members of the genus *Cypovirus* such as cytoplasmic polyhedrosis virus; members of the genus *Fijivirus* such as Southern rice black-streaked dwarf virus; members of the genus *Phytoreovirus* such as rice dwarf virus; and members of the genus *Oryzavirus* such as rice ragged stunt virus. The production method of the present invention is particularly preferably applied to an artificial recombinant Mammalian orthoreovirus or rotavirus.

The expression cassettes for individual RNA genome segments of a virus are not particularly limited as long as the expression cassettes are designed to allow the expression of single-stranded plus strand RNA (viral mRNA) to serve as a template of the segmented genome dsRNA of the virus. Preferably, each expression cassette is composed of, from the upstream, an RNA polymerase promoter, a DNA encoding an RNA genome segment (a cDNA of an RNA genome segment) and a DNA encoding a self-cleaving ribozyme. In the case where the RNA polymerase promoter is T7 promoter, the expression cassette contains a T7 terminator sequence. In the case where the RNA polymerase promoter is a polymerase I promoter, the expression cassette contains a terminator sequence corresponding to the promoter. In the case where the RNA polymerase promoter is a polymerase II promoter, the expression cassette contains a polyadenylation signal sequence.

Each of the expression cassettes for individual RNA genome segments of a virus may be composed only of an RNA polymerase promoter and a DNA encoding an RNA genome segment (a cDNA of an RNA genome segment). A vector containing such an expression cassette is cleaved at the 3' end of the DNA encoding an RNA genome segment with, for example, a restriction enzyme, resulting in a linear vector. The linear vector encodes the viral genome in the 3' end region, and therefore can be used without the risk of transcription of the original sequence of the vector.

The cDNA of each RNA genome segment can be obtained by RNA extraction from the virus, followed by RT-PCR using the extracted dsRNA as a template. The primer sets used for RT-PCR can be designed to be specific to the corresponding RNA genome segments based on their nucleotide sequences. Information on the nucleotide sequence of each RNA genome segment is available from known databases (GenBank etc.). Alternatively, the nucleotide sequence of each RNA genome segment may be determined by a known method using a commercial sequencer.

Preferable examples of the RNA polymerase promoter include T7 promoter, polymerase I promoter, and polymerase II promoters including CAG promoter and CMV promoter. Preferred is T7 promoter.

The self-cleaving ribozyme can be selected as appropriate from known self-cleaving ribozymes. Examples of the self-cleaving ribozyme include a hammerhead ribozyme, a hairpin ribozyme, ribonuclease P subunit M1, a hepatitis D virus (HDV) ribozyme and a Varkud satellite ribozyme. Preferred is an HDV ribozyme.

Preferable examples of the vector into which the RNA genome segment expression cassette is to be inserted include known cloning vectors, known mammalian cell expression vectors and various types of known viral vectors (a vaccinia virus vector, an adenovirus vector, an adeno-associated virus vector, a retrovirus vector, a lentivirus vector, etc.).

In the case where each vector contains a single RNA genome segment expression cassette, the vectors as many as the viral genome segments represent one set. A polycistronic vector containing two or more RNA genome segment expression cassettes may be used. The number of the RNA genome segment expression cassettes contained in a single vector is not limited, and one vector may contain all the RNA genome segment expression cassettes. In view of the efficiency of artificial recombinant virus production, the number of vectors is preferably smaller.

The single-stranded RNA (ssRNA) to be introduced into host cells is a plus strand RNA and can be obtained by in vitro transcription from the corresponding RNA genome segment expression cassette. The in vitro transcription can be performed, for example, using a commercial reagent (e.g., in vitro Transcription T7 Kit (Takara Bio) etc.). After in vitro transcription, the obtained RNA is desirably capped using a cap analog (e.g., Ribo m7G Cap Analog (Promega) etc.) before use. The set of ssRNAs include ssRNAs as many as the viral genome segments.

Examples of the FAST (fusion-associated small transmembrane) protein that can be used include FAST proteins of known fusogenic reoviruses belonging to the genus *Orthoreovirus* of the family Reoviridae and FAST proteins of yet-to-be-isolated viruses. Specific examples include Nelson Bay reovirus p10 (GenBank ACCESSION: BAJ52806), Avian reovirus p10 (GenBank ACCESSION: AG032037), Broome reovirus p13 (GenBank ACCESSION: YP 003717780), Reptilian reovirus p14 (GenBank ACCESSION: AAP03134), Baboon reovirus p15 (GenBank ACCESSION: YP 004769555), grass carp reovirus p16 (GenBank ACCESSION: ABV01045), and Atlantic salmon reovirus p22 (GenBank ACCESSION: ACN38055). Preferred are Nelson Bay reovirus p10 and Avian reovirus p10.

Figure 10:
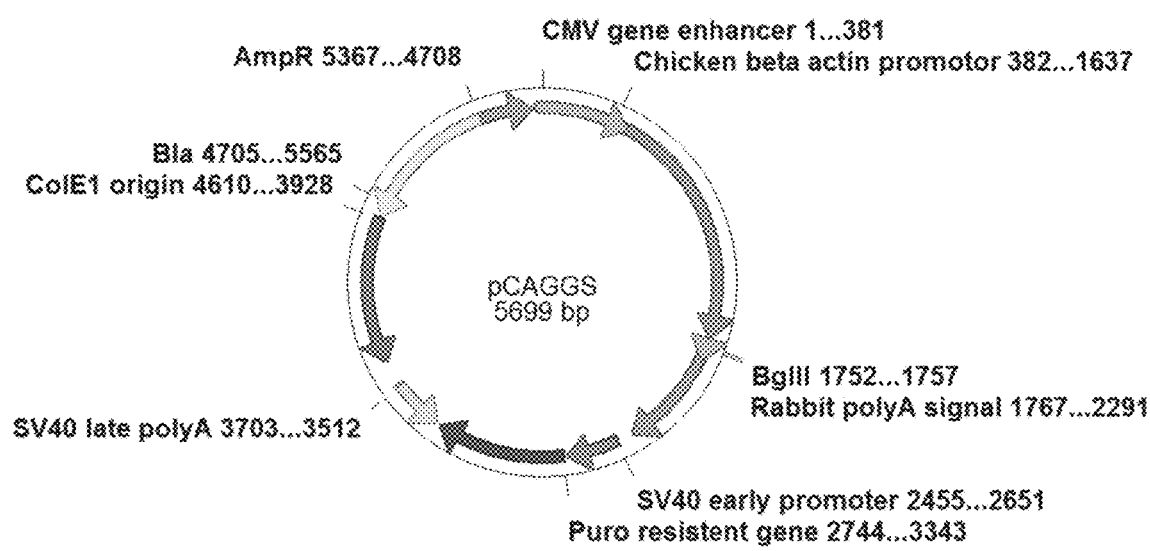
FIG. 10 shows the structure of plasmid pCAGGS.

The FAST protein expression vector can be prepared by inserting a gene encoding any of the above FAST proteins into a known mammalian cell expression vector, exemplified by plasmid pCAGGS (see FIG. 10), or a known viral vector. The nucleotide sequence data of the FAST protein-encoding gene can be obtained from the nucleotide sequence data of the viral genome of interest. The nucleotide sequence data of the viral genome may be the ones registered in known databases (GenBank etc.). The nucleotide sequence of the gene encoding Nelson Bay reovirus p10 may be, for example, the nucleotide sequence of SEQ ID NO: 26. The nucleotide sequence of the gene encoding Avian reovirus p10 may be, for example, the nucleotide sequence of SEQ ID NO: 27.

Instead of the FAST protein expression vector, a single-stranded plus strand RNA encoding the FAST protein may be used. The single-stranded plus strand RNA encoding the FAST protein can be obtained, for example, by in vitro transcription from the FAST protein expression vector. The in vitro transcription can be performed, for example, using a commercial reagent (e.g., in vitro Transcription T7 Kit (Takara Bio) etc.). After in vitro transcription, the obtained RNA is desirably capped using a cap analog (e.g., Ribo m7G Cap Analog (Promega) etc.) before use.

The capping enzyme is not particularly limited as long as the enzyme can catalyze mRNA capping in the cytoplasm. For example, capping enzymes of DNA or RNA viruses which replicate in the cytoplasm of host cells can preferably be used. The capping enzymes of DNA viruses which replicate in the cytoplasm of host cells include, for example, capping enzymes encoded by viruses in the family Poxviridae and capping enzymes encoded by viruses in the family Asfarviridae. The capping enzymes of RNA viruses which replicate in the cytoplasm of host cells include, for example, nsp1 protein of viruses in the family Togaviridae. Preferred are capping enzymes encoded by viruses in the family Poxviridae or Asfarviridae. Among the capping enzymes encoded by viruses in the family Poxviridae, vaccinia virus capping enzymes can preferably be used. Among the capping enzymes encoded by viruses in the family Asfarviridae, African swine fever virus capping enzyme NP868R can preferably be used. In the case where a vaccinia virus capping enzyme is used, expression vectors for the capping enzyme can be prepared by inserting a gene (D1R) encoding the large subunit of the capping enzyme (GenBank ACCESSION:YP_232988) and a gene (D12L) encoding the small subunit of the capping enzyme (GenBank ACCESSION: YP_232999) into separate vectors such as known mammalian cell expression vectors exemplified by plasmid pCAGGS (see FIG. 10) and known viral vectors. The nucleotide sequence of the gene encoding the large subunit of a vaccinia virus capping enzyme may be, for example, the nucleotide sequence of SEQ ID NO: 29. The nucleotide sequence of the gene encoding the small subunit of a vaccinia virus capping enzyme may be, for example, the nucleotide sequence of SEQ ID NO: 30. A polycistronic vector containing capping enzyme subunit expression cassettes together with a FAST protein expression cassette may be used.

Instead of the capping enzyme expression vectors, single-stranded plus strand RNAs encoding the subunits of the capping enzyme may be used. The single-stranded plus strand RNAs encoding the subunits of the capping enzyme can be obtained, for example, by in vitro transcription from the expression vectors for the subunits of the capping enzyme. The in vitro transcription can be performed, for example, using a commercial reagent (e.g., in vitro Transcription T7 Kit (Takara Bio) etc.). After in vitro transcription, the obtained RNAs are desirably capped using a cap analog (e.g., Ribo m7G Cap Analog (Promega) etc.) before use.

The host cells are preferably cells with high susceptibility to viruses in the family Reoviridae and high transfection efficiency. Examples of such cells include but not limited to BHK cells, MA104 cells, COST cells, CV1 cells, Vero cells, L929 cells, 293T cells and A549 cells. In addition, modified cells derived from any of the above cells (newly cloned cells, foreign gene-transfected cells, etc.) can also preferably be used as the host cells.

In the case where T7 promoter is used as the promoter of each RNA genome segment expression cassette, recombinant T7 RNA polymerase-expressing cells can be used as the host cells. The recombinant T7 RNA polymerase-expressing cells can be prepared, for example, by transfecting appropriate host cells with a mammalian cell expression vector containing a gene encoding T7 RNA polymerase (GenBank ACCESSION: ADJ00046) and selecting cells stably expressing T7 RNA polymerase by a drug-based selection technique or the like. Alternatively, cells transiently or permanently expressing a recombinant T7 RNA polymerase can be prepared, for example, by infecting appropriate host cells with a viral vector (a vaccinia virus vector, an adenovirus vector, an adeno-associated virus vector, a retrovirus vector, a lentivirus vector or the like) containing a gene encoding T7 RNA polymerase. The nucleotide sequence of the gene encoding T7 RNA polymerase may be, for example, the nucleotide sequence of positions 894 to 3545 of "T7 RNA polymerase vector pGemT7cat" (GenBank ACCESSION: HM049174). Another example of the recombinant T7 RNA polymerase-expressing cells may be known recombinant T7 RNA polymerase-expressing cells (e.g., BHK/T7-9: Ito, N et al., (2003), Microbiology and immunology 47, 613-617).

The introduction of a FAST protein expression vector and/or a capping enzyme expression vector into host cells in step (1) and the introduction of a vector containing expression cassettes for individual RNA genome segments of a virus or of a set of single-stranded RNA transcripts from the expression cassettes into host cells in step (2) can be performed using a known transfection method, such as electroporation, the calcium phosphate method, the liposome method or the DEAE dextran method. Commercial transfection reagents (e.g., TransIT-LT1 (trade name, Mirus) etc.) can also be used for the introduction.

In the production method of the present invention, step (1) and step (2) may be performed separately or concurrently. In the case where step (1) and step (2) are performed separately, step (1) may precede or follow step (2). Step (1) and step (2) are preferably performed concurrently. That is, the method of the present invention preferably comprises the steps of:
(I) introducing a FAST protein expression vector and/or a capping enzyme expression vector into host cells, concurrently with introducing a vector containing expression cassettes for individual RNA genome segments of a virus or introducing a set of single-stranded RNA transcripts from the expression cassettes into the host cells; and
(II) culturing the host cells.

The host cells into which the FAST protein expression vector and/or the capping enzyme expression vector have been introduced may transiently or permanently express the FAST protein and/or the capping enzyme. In the case where the recombinant T7 RNA polymerase-expressing cells as described above are used as the host cells, the transfected host cells may be cells permanently expressing a FAST protein and/or a capping enzyme in addition to T7 RNA polymerase. The cells permanently expressing a FAST protein and/or a capping enzyme can be prepared by introducing a FAST protein expression vector and/or a capping enzyme expression vector into cells and selecting cells stably expressing a FAST protein and/or a capping enzyme by a drug-based selection technique or the like. The permanently expressing cells may be cells which constitutively express a FAST protein and/or a capping enzyme, or cells which express a FAST protein and/or a capping enzyme in a controlled manner, for example, under a Tet on/off system etc. Alternatively, cells transiently or permanently expressing a FAST protein and/or a capping enzyme can be prepared, for example, by infecting appropriate host cells with a viral vector (a vaccinia virus vector, an adenovirus vector, an adeno-associated virus vector, a retrovirus vector, a lentivirus vector or the like) containing a gene encoding a FAST protein and/or a gene encoding a capping enzyme.

The amount of the nucleic acid used for transfection is preferably selected as appropriate for the size of the culture plate used, the type of the host cells, the seeding cell number, etc. For example, in the case where BHK cells stably expressing T7 RNA polymerase are seeded as host cells at $8\times10^5$ cells/well on a 6-well plate on the previous day of transfection, the DNA amount of each RNA genome segment expression vector is preferably 0.5 to 1.0 µg, the DNA amount of the FAST protein expression vector is preferably 0.002 to 0.02 µg, and the DNA amount of the capping enzyme expression vector is preferably 0.5 to 1.0 µg. For example, in the case where BHK cells stably expressing T7 RNA polymerase are seeded as host cells at $4\times10^5$ cells/well on a 12-well plate on the previous day of transfection, the DNA amount of each RNA genome segment expression vector is preferably 0.25 to 0.5 µg, the DNA amount of the FAST protein expression vector is preferably 0.0001 to 0.01 µg, and the DNA amount of the capping enzyme expression vector is preferably 0.25 to 0.5 µg.

For the culture of the host cells, a medium suitable for the host cells is selected and used. Cytopathic changes of the host cells indicate that the artificial recombinant virus has been produced. The medium and cells on a plate or in a well in which cytopathic changes have been observed are harvested to prepare a cell lysate, which may be used as a virus sample. Alternatively, a virus sample can be prepared by isolation of the virus from the cell lysate by plaque assay, followed by mass culture and viral particle purification. The viral particle purification can be performed by known methods (e.g., cesium chloride density gradient centrifugation etc.).

After culturing the host cells for several days, regardless of the presence or absence of cytopathic changes, a cell lysate may be prepared as described above and added to other cells for virus passage. The cells to which the cell lysate is added are preferably highly virus-susceptible cells, and more preferably cells with high susceptibility to the virus of interest. For example, for production of an artificial recombinant rotavirus, MA104 cells or CV1 cells are preferable. Cytopathic changes of the cells cultured with the cell lysate indicate that the artificial recombinant virus has been produced.

Several days after the transfection of the set of vectors etc. into host cells, highly virus-susceptible cells as described above may be additionally seeded on the culture plate or in the wells containing the host cells and co-cultured with the host cells. In the case of such co-culture, the seeding cell number of the additional cells is preferably about 1/5 to 1/20 of the cells having been subjected to the transfection. After cell addition, culture is continued in a trypsin-containing (e.g., about 0.5 µg/mL) serum-free medium for about 3 to 5 days. Then, a cell lysate is prepared and added to highly virus-susceptible cells for passage. The highly virus-susceptible cells are cultured in the same trypsin-containing serum-free culture medium as above. Cytopathic changes of the cells indicate that the artificial recombinant virus has been produced. The medium and cells on a plate or in a well in which cytopathic changes have been observed are harvested to prepare a cell lysate, which may be used as a virus sample. Alternatively, a virus sample can be prepared by isolation of the virus from the cell lysate by plaque assay, followed by mass culture and viral particle purification. The viral particle purification can be performed by known methods (e.g., cesium chloride density gradient centrifugation etc.).

According to the production method of the present invention, an artificial recombinant virus having a mutation introduced in at least one RNA genome segment, an artificial recombinant virus having a foreign gene inserted in at least one RNA genome segment, or an artificial recombinant virus having a mutation introduced in at least one RNA genome segment and a foreign gene inserted in at least one RNA genome segment can be produced. Such artificial recombinant viruses can be produced by introducing a desired mutation into an expression cassette for the RNA genome segment and/or by inserting a desired foreign gene into an expression cassette for the RNA genome segment. The mutation introduction and foreign gene insertion into an expression cassette for the RNA genome segment can be performed by known gene recombination techniques.

The present inventors have successfully produced an artificial recombinant rotavirus which has a deletion mutation in rotavirus NSP1 and is capable of autonomous proliferation, an artificial recombinant rotavirus which has a deletion mutation in rotavirus NSP3 and is capable of autonomous proliferation, and an artificial recombinant rotavirus which has a mutation resulting in amino acid substitution in rotavirus NSP4 and is capable of autonomous proliferation. According to the production method of the present invention, an artificial recombinant rotavirus incapable of autonomous proliferation can be produced by partial deletion of a viral protein gene essential for proliferation. More specifically, an artificial recombinant virus incapable of autonomous proliferation can be produced using host cells modified to express a mutant form of a viral protein essential for proliferation due to partial deletion of the corresponding gene. Such an artificial recombinant virus can proliferate only in cells expressing a normal form of the viral protein. Therefore, this type of artificial recombinant virus can be applied to the production of single-round infectious virus-like particles and is expected to be useful as a vaccine. Moreover, an artificial recombinant virus as an attenuated vaccine candidate can also be produced by introducing a mutation into a known viral protein gene associated with the degree of virulence.

In addition, the present inventors have successfully produced an artificial recombinant rotavirus expressing luciferase by inserting a luciferase gene (Nluc gene) into the rotavirus NSP1 gene. Moreover, the present inventors have successfully produced an artificial recombinant rotavirus expressing ZsGreen by inserting a green fluorescent protein gene (ZsGreen gene) into the rotavirus NSP1 gene. The foreign gene can be inserted into any genome segment of a rotavirus. The foreign gene is not limited to a gene of 500 bp or longer, such as a Nluc gene (SEQ ID NO: 31) or a ZsGreen gene (SEQ ID NO: 33). For example, a short peptide can be expressed in a fusion protein with a viral protein. In the case where the artificial recombinant rotavirus has two or more foreign genes, the two or more foreign genes may be inserted in separate genome segments or inserted in one genome segment. The combination of the mutation and the foreign gene in the genome segments is also not particularly limited and can be selected as appropriate.

An expression vector for the foreign gene preferably contains a genome segment expression cassette having a partial deletion in the rotavirus NSP1 gene and an insertion of the foreign gene in the rotavirus NSP1 gene. The insertion site of the foreign gene is not particularly limited and is preferably within a region which starts at about 30 to 200 bases downstream from the 5' end (including the untranslated region) of the NSP1 gene and ends at about 30 to 200 bases upstream from the 3' end (including the untranslated region) of the NSP1 gene. More preferably, the insertion site is in the region of about 80 to 150 bases from the 5' end (including the untranslated region) of the NSP1 gene. Still more preferably, the insertion site is in the region of about 100 to 130 bases from the 5' end (including the untranslated region) of the NSP1 gene. The deletion region in the NSP1 gene is particularly not limited, but is preferably downstream the insertion site of the foreign gene. The 3'-end region (including the untranslated region) of the NSP1 gene, however, is preferably retained. Preferably, a region of at least about 30 bases or more, about 50 bases or more, about 100 bases or more, or about 200 bases or more from the 3' end of the NSP1 gene is retained. The number of bases deleted is not particularly limited and may be 1550 bases or less, 1200 bases or less, 1000 bases or less, 800 bases or less, 700 bases or less, 600 bases or less, 500 bases or less, or 400 bases or less. In addition, the number of bases deleted may be 100 bases or more, 200 bases or more, or 300 bases or more. With such a foreign gene expression vector, an artificial recombinant rotavirus which stably retains a foreign gene over a long period of time and stably expresses the foreign gene product can be produced.

The artificial recombinant virus having a mutation and the virus expressing a foreign gene, each of which is produced by the production method of the present invention, are useful for functional analysis of viral proteins and for the development of vaccines and vaccine vectors. The artificial recombinant virus having a mutation and the virus expressing a foreign gene can be used also as vaccines.

The production method of the present invention can enhance the efficiency of artificial recombinant rotavirus production by overexpressing a rotavirus NSP2 gene product and/or a rotavirus NSP5 gene product in the host cells. Either or both of the NSP2 gene product and the NSP5 gene product may be overexpressed in the host cells. Preferably, both the NSP2 gene product and the NSP5 gene product are overexpressed in the host cells.

The overexpression of the NSP2 gene product and/or the NSP5 gene product in the host cells can be effected by preparing a vector expressing the NSP2 gene product (hereinafter referred to as an "NSP2 expression vector") and a vector expressing the NSP5 gene product (hereinafter referred to as an "NSP5 expression vector") and introducing either or both of them into the host cells. The NSP2 expression vector and the NSP5 expression vector can be prepared, for example, by inserting the NSP2 gene (GenBank ACCESSION: LC178571, SEQ ID NO: 18) and the NSP5 gene (GenBank ACCESSION: LC178574, SEQ ID NO: 21) into separate vectors such as known mammalian cell expression vectors exemplified by plasmid pCAGGS (see FIG. 10) and known viral vectors.

The NSP2 gene to be inserted into the NSP2 expression vector and the NSP5 gene to be inserted into the NSP5 expression vector may be from the strain of an artificial recombinant rotavirus to be produced, or from a rotavirus of a different genotype, a different serotype or a different animal (a human, a monkey, a horse, a bird, a dog, a pig, a cow, a mouse, a rat, a rabbit, etc.). A polycistronic vector containing the NSP2 expression cassette together with the NSP5 expression cassette may be used.

Instead of the NSP2 expression vector, a single-stranded plus strand RNA encoding NSP2 may be used. Similarly, instead of the NSP5 expression vector, a single-stranded plus strand RNA encoding NSP5 may be used. These single-stranded plus strand RNAs can be obtained, for example, by in vitro transcription from the NSP2 expression vector and the NSP5 expression vector. The in vitro transcription can be performed, for example, using a commercial reagent (e.g., in vitro Transcription T7 Kit (Takara Bio) etc.). After in vitro transcription, the obtained RNAs are desirably capped using a cap analog (e.g., Ribo m7G Cap Analog (Promega) etc.) before use.

The overexpression of the NSP2 gene product and/or the NSP5 gene product in the host cells can be effected without using the NSP2 expression vector and/or the NSP5 expression vector, more specifically, by increasing the amount(s) of an RNA genome segment expression vector for expressing segment 8 (NSP2 gene) (segment 8 expression vector) and/or an RNA genome segment expression vector for expressing segment 11 (NSP5 gene) (segment 11 expression vector) introduced into the host cells as compared with those of RNA genome segment expression vectors for expressing segments other than segment 8 or 11. The DNA amount(s) of the segment 8 expression vector and/or the segment 11 expression vector introduced into the host cells are/is not particularly limited as long as each DNA amount is larger than those of the other RNA genome segment expression vectors. Each DNA amount may be about 1.5- to 10-fold larger, or about 2- to 5-fold larger than those of the other RNA genome segment expression vectors. See Table 2 in Example 2 for each rotavirus genome segment.

Further, the present inventors have confirmed that an artificial recombinant rotavirus can be produced even without using the host cells expressing a FAST protein and/or a capping enzyme (see Example 10). That is, the present invention provides a method for producing an artificial recombinant rotavirus, the method comprising introducing a vector containing expression cassettes for 11 individual rotavirus RNA genome segments or introducing a set of 11 ssRNA transcripts from the expression cassettes into host cells expressing neither a FAST protein nor a capping enzyme, and culturing the host cells.

A first embodiment of this production method involves using host cells into which an NSP2 expression vector and/or an NSP5 expression vector have been introduced. A second embodiment thereof involves introducing only a vector containing expression cassettes for 11 individual rotavirus RNA genome segments or introducing only a set of 11 ssRNA transcripts from the expression cassettes into host cells. In the second embodiment, it is preferable that the amount(s) of a segment 8 expression vector and/or a segment 11 expression vector introduced into the host cells are/is increased as compared with those of the rest of the expression vectors for 11 rotavirus RNA genome segments. The DNA amount(s) of the segment 8 expression vector and/or the segment 11 expression vector introduced into the host cells are/is not particularly limited as long as each DNA amount is larger than those of the other RNA genome segment expression vectors. Each DNA amount may be about 1.5- to 10-fold larger, or about 2- to 5-fold larger than those of the other RNA genome segment expression vectors.

The rotavirus NSP2 and NSP5 are known to form a viral inclusion body in infected cells and function to provide a site of viral replication (Hu L, Crawford S, Hyser J, Estes M, and Prasad V (2012): *Rotavirus* non-structural proteins: Structure and Function Current Opinion in Virology 2(4): 380-388). A viral inclusion body is a structure found in common among viruses in the family Reoviridae. For example, µNS encoded by the M3 gene of the genus *Orthoreovirus* of the Family Reoviridae (Mammalian orthoreovirus, Nelson Bay reovirus, Avian reovirus, etc.), σNS encoded by the S3 or S4 gene of the same genus as above, and NS2 encoded by segment 8 of the genus *Orbivirus* of the Family Reoviridae (African horse sickness virus, bluetongue virus, etc.) are also known to form a viral inclusion body and function to provide a site of viral replication (Thomas C P, Booth T F, Roy P (1990): Synthesis of bluetongue virus-encoded phosphoprotein and formation of inclusion bodies by recombinant baculovirus in insect cells: it binds the single-stranded RNA species. Journal of General Virology, 71 (Pt 9): 2073-2083). Based on this knowledge, the present inventors used host cells into which a µNS expression vector and a σNS expression vector have been introduced in the course of the production of an artificial recombinant Mammalian orthoreovirus, and confirmed that this approach greatly improved the efficiency of artificial recombinant virus production (see Example 13).

Therefore, the present invention provides a method for producing an artificial recombinant virus of the family Reoviridae, the method comprising introducing a vector containing expression cassettes for individual RNA genome segments of a virus or introducing a set of single-stranded RNA transcripts from the expression cassettes into host cells;

overexpressing, in the host cells, a gene product involved in the formation of viral inclusion bodies in infected cells; and culturing the host cells.

The host cells may be host cells expressing a FAST protein and/or a capping enzyme or host cells expressing neither a FAST protein nor a capping enzyme. Examples of the gene product involved in the formation of viral inclusion bodies in infected cells include µNS encoded by the M3 gene of a virus in the genus *Orthoreovirus*, σNS encoded by the S3 or S4 gene of a virus in the genus *Orthoreovirus*, and NS2 encoded by segment 8 of the genus *Orbivirus*. One of these gene products may be used, and also two or more of them may be used in combination.

For the overexpression of a gene product involved in the formation of viral inclusion bodies in infected cells, an expression vector for the desired gene may be introduced into the host cells. Alternatively, a vector containing an expression cassette for an RNA genome segment encoding the desired gene may be introduced, into the host cells, in an increased DNA amount as compared with those of the other RNA genome segment expression vectors. The DNA amount of the vector containing an expression cassette for an RNA genome segment encoding the desired gene may be about 1.5- to 10-fold larger, or about 2- to 5-fold larger than those of the other RNA genome segment expression vectors.

Artificial Recombinant *Rotavirus* and Vaccine

The present invention provides an artificial recombinant rotavirus having a mutation resulting in functional suppression of at least one selected from NSP1, NSP3 and NSP4. The present inventors have successfully produced an artificial recombinant rotavirus having a C-terminal 108-amino-acid deletion in rotavirus NSP1. The C-terminal region of NSP1 is known to play an important role in the suppression of natural immunity (Barro, M., and Patton, J. T. (2005). *Rotavirus* nonstructural protein 1 subverts innate immune response by inducing degradation of IFN regulatory factor 3. Proceedings of the National Academy of Sciences of the United States of America 102, 4114-4119). Therefore, this artificial recombinant rotavirus is a replication-competent attenuated virus and is expected to be useful as a vaccine. The present inventors have also produced an artificial recombinant rotavirus having a deletion mutation in NSP3 and an artificial recombinant rotavirus having a mutation resulting in amino acid substitution in NSP3, and have confirmed that artificial recombinant rotaviruses having a mutation in NSP1, NSP3 or NSP4 are less proliferative as compared with the wild-type artificial recombinant rotavirus. Therefore, the artificial recombinant rotaviruses having a mutation in NSP3 or NSP4 are also replication-competent attenuated viruses and are expected to be useful as vaccines. The present invention also includes a vaccine comprising an artificial recombinant rotavirus having a mutation resulting in functional suppression of at least one selected from NSP1, NSP3 and NSP4.

The present invention provides an artificial recombinant rotavirus expressing a foreign gene. The foreign gene is not particularly limited, and for example, when the foreign gene encodes a vaccine antigen, the produced artificial recombinant rotavirus can be used as a vaccine. Examples of the vaccine antigen include a Norovirus antigen, which causes oral or mucosal infections, an adenovirus antigen, a hepatitis A antigen, a Sapovirus antigen, a hand-foot-and-mouth disease virus antigen, an enterovirus antigen, an HIV antigen, a *Salmonella* antigen, a *Campylobacter* antigen, a *Vibrio parahaemolyticus* antigen, an *E. coli* O-157 antigen, a cholera antigen, a typhoid antigen and a dysentery antigen.

These vaccine antigens may be epitope peptides thereof. A combination of two or more of artificial recombinant rotaviruses expressing different foreign vaccine antigens can compose a vaccine.

Figure 9:
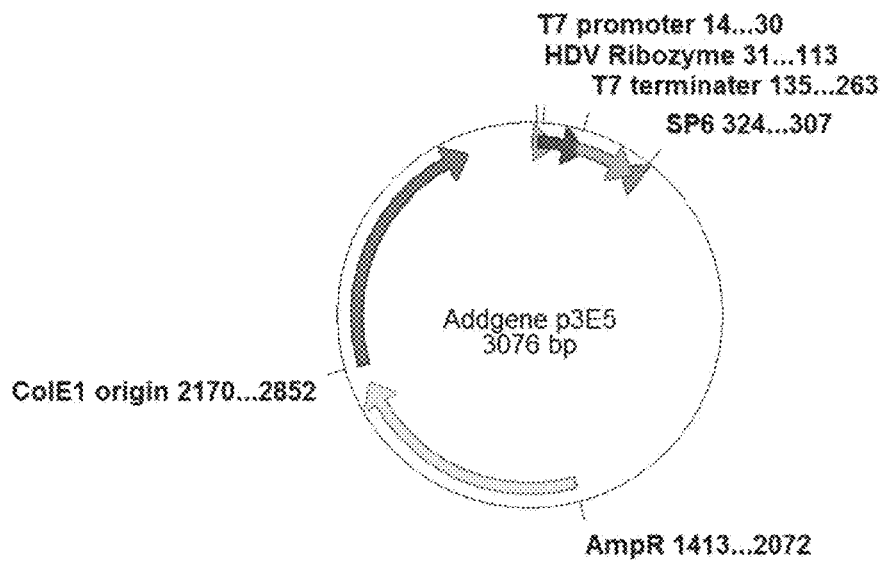
FIG. 9 shows the structure of plasmid p3E5.

An artificial recombinant rotavirus expressing, as a foreign gene, one or more genes encoding an antigen protein(s) of a different type or strain of rotavirus (e.g., VP4, VP7, etc.) can be provided as a polyvalent rotavirus vaccine. The antigen protein may be an epitope peptide thereof.

An artificial recombinant rotavirus expressing a reporter gene readily allows the visualization of the amount of virus, and therefore, can be applied to screening for new anti-rotavirus drugs. The reporter gene can be selected as appropriate from known reporter genes. Preferable examples include a luciferase gene, a GFP gene and an RFP gene.

The present invention provides an artificial recombinant reassortant rotavirus. A reassortant rotavirus refers to a rotavirus which has a novel genotypic composition resulting from recombination between the genome segments of different types or strains of rotaviruses. A reassortant is also called a genetically reassorted strain. With the production method of the present invention, an artificial recombinant reassortant rotavirus between any two types of rotaviruses can be designed and produced. Exchange of gene segments between different viral strains occurs also in natural infection and is considered as an important evolutionary strategy in viruses with a segmented genome such as rotaviruses. The artificial recombinant rotavirus reassortant between different types or strains of rotaviruses is useful for functional analysis of their genome segments and is also very useful as a vaccine candidate. For example, a reassortant containing VP4 gene segments of different serotypes of rotaviruses or VP7 gene segments of different serotypes of rotaviruses can be used as a bivalent rotavirus vaccine. A mixture of two or more of such reassortants can compose a multivalent rotavirus vaccine.

Method for Promoting Viral Replication

The present invention provides a method for promoting viral replication. The method of the present invention for promoting viral replication comprises infecting host cells expressing a FAST protein with a virus and culturing the host cells. The virus that infects host cells is not particularly limited and is preferably a virus of the family Reoviridae. In particular, preferred are Mammalian orthoreovirus and rotaviruses. The host cells expressing a FAST protein can be prepared by introducing a FAST protein expression vector into appropriate host cells. The FAST protein expression vector can be a FAST protein expression vector as described above in the production method of the present invention. The host cells and the introduction method of the vector into the host cells can also be the same as those described above in the production method of the present invention. The host cells expressing a FAST protein may transiently or permanently express the FAST protein.

The amount of the nucleic acid used for transfection is preferably selected as appropriate for the size of the culture plate used, the type of the host cells, the seeding cell number, etc. For example, in the case where Vero cells are seeded as host cells at $8\times10^5$ cells/well on a 6-well plate on the previous day of transfection, the DNA amount of the FAST protein expression vector is preferably 0.002 to 0.02 μg. The DNA amount used for transfection can be changed as appropriate such that it is proportional to the seeding cell number suitable for a plate to be used.

The infection of host cells with a virus can be performed by adding a virus sample to a culture medium of the host cells. The infectious dose is not particularly limited, and the MOI is preferably 0.1 to 0.0001. The culture period is not particularly limited and is preferably 16 to 48 hours.

With the method of the present invention for promoting viral replication, proliferation (replication) of a virus with a low proliferation (replication) capacity can be promoted. In addition, this method is useful for preparation of a high-titer viral stock.

EXAMPLES

Hereinafter, the present invention will be described in detail by examples, but the present invention is not limited thereto.

Example 1: Improvement of Reverse Genetics System for Mammalian *Orthoreovirus*

Mammalian orthoreovirus (MRV) has been extensively studied as a model virus of the family Reoviridae. An entirely plasmid-based reverse genetics (RG) system for MRV is the first system developed in the family Reoviridae (Non Patent Literature 3). For the purpose of improving RG systems for the family Reoviridae, it was examined whether the use of a FAST protein encoded by a group of fusogenic reoviruses and a capping enzyme encoded by vaccinia virus could enhance the efficiency of artificial recombinant virus production.

Materials and Methods (1) Viruses

Mammalian orthoreovirus strain type 1 Lang (hereinafter referred to as "MRV T1L") was used. MRV T1L can be purchased from ATCC (ATCC VR-230). The gene names and GenBank accession numbers of 10 individual RNA genome segments of MRV T1L are shown in Table 1.

TABLE 1

Sequences of genome segments of MRV T1L

| Gene name | GenBank ACCESSION | SEQ ID NO |
|---|---|---|
| L1 | M24734 | 1 |
| L2 | AF378003 | 2 |
| L3 | AF129820 | 3 |
| M1 | AF461682 | 4 |
| M2 | AF490617 | 5 |
| M3 | AF174382 | 6 |
| S1 | EF494445 | 7 |
| S2 | L19774 | 8 |
| S3 | M14325 | 9 |
| S4 | M13139 | 10 |

(2) Preparation of Plasmids Containing Expression Cassettes for Individual RNA Genome Segments (RNA Genome Segment Expression Vectors) of MRV T1L Plasmids containing cDNAs of the 10 individual RNA genome segments of MRV T1L (L1 to L3, M1 to M3, S1 to S4) were prepared as described in reference 1 (Kobayashi et al., Virology. 2010 Mar. 15; 398(2):194-200). The specific procedure was as follows. The individual RNA genome segments were amplified by RT-PCR from extracted viral dsRNA as a template using the respective specific primers designed based on the nucleotide sequence of each segment. The RT-PCR products (cDNAs of the individual RNA genome segments) were individually cloned into p3E5EGFP (Watanabe et al., (2004), Journal of virology, 78, 999-1005) to yield plasmids each having an expression cassette in which the cDNA of the desired single RNA genome segment was flanked by a T7 promoter sequence (SEQ ID NO: 22) at the 5' end and a hepatitis D virus (HDV) ribozyme sequence (SEQ ID NO: 23) at the 3' end, followed by a T7 terminator sequence (SEQ ID NO: 24). Each of the obtained plasmids had a structure in which the cDNA encoding the desired single RNA genome segment was inserted between the T7 promoter sequence and the HDV ribozyme sequence (between positions 30 and 31 of SEQ ID NO: 25) of plasmid p3E5 (3076 bp, SEQ ID NO: 25, shown in FIG. 9).

Next, an M2 expression cassette was inserted into a plasmid with cloned L1 (pT7-L1T1L) to yield a cistronic plasmid (pT7-L1-M2T1L). Similarly, an M2 expression cassette was inserted into a plasmid with cloned L2 (pT7-L2T1L) to yield a cistronic plasmid (pT7-L2-M3T1L), and an S3 expression cassette was inserted into a plasmid with cloned L3 (pT7-L3T1L) to yield a cistronic plasmid (pT7-L3-S3T1L). Further, expression cassettes for S3, S4 and M1 were inserted into a plasmid with cloned S2 (pT7-S2T1L) to yield a tetracistronic plasmid (pT7-51-52-S4-M1T1L).

(3) Preparation of FAST Protein Expression Vector

A FAST protein expression vector was prepared by inserting the protein-coding region DNA (SEQ ID NO: 26) of the Nelson Bay reovirus p10 gene (see GenBank ACCESSION: AB908284) or the protein-coding region DNA (SEQ ID NO: 27) of the Avian reovirus p10 gene (see GenBank ACCESSION: AF218358) into plasmid pCAGGS (5699 bp, SEQ ID NO: 28, shown in FIG. 10, Matsuo et al., 2006, Biochem Biophys Res Commun 340(1): 200-208). These coding region DNAs were synthesized by custom gene synthesis services (Eurofins Genomics) based on the nucleotide sequences of SEQ ID NOs: 27 and 28. These synthetic DNAs were individually inserted into the BglII restriction site of plasmid pCAGGS (between positions 1753 and 1754 of SEQ ID NO: 28) to yield pCAG-p10 (Nelson Bay reovirus p10 expression vector) and pCAG-ARVp10 (Avian reovirus p10 vector).

(4) Preparation of Capping Enzyme Expression Vectors

Capping enzyme expression vectors were prepared by inserting the protein-coding region DNA of the vaccinia virus D1R gene (GenBank ACCESSION: NC006998, positions 93948 to 96482, SEQ ID NO: 29) and the protein-coding region DNA of the vaccinia virus D12L gene (GenBank ACCESSION: NC006998, positions 107332 to 108195, SEQ ID NO: 30) into the same plasmid pCAGGS as above. These coding region DNAs were synthesized by custom gene synthesis services (Eurofins Genomics) based on the nucleotide sequences of SEQ ID NOs: 29 and 30. These synthetic DNAs were individually inserted into the BglII restriction site of plasmid pCAGGS (between positions 1753 and 1754 of SEQ ID NO: 28) to yield pCAG-D1R (expression vector for the vaccinia virus mRNA capping enzyme large subunit) and pCAG-D12L (expression vector for the vaccinia virus mRNA capping enzyme small subunit).

(5) Host Cells

BHK-T7/P5 cells, which stably express T7 RNA polymerase, were used. The BHK-T7/P5 cells were prepared by transfecting BHK cells (Baby Hamster Kidney Cells) with a plasmid pCAGGS having a T7 RNA polymerase-encoding DNA inserted downstream of the CAG promoter and subsequently culturing the BHK cells in a puromycin-containing medium for selection.

(6) Production of Artificial Recombinant Virus

BHK-T7/P5 cells were seeded on 24-well culture plates at $2\times10^5$ cells/well on the previous day of transfection. The BHK-T7/P5 cells were transfected with 0.4 µg each of the RNA genome segment expression vectors (pT7-L1-M2T1L, pT7-L2-M3T1L, pT7-L3-S3T1L and pT7-S1-S2-S4-M1T1L); 0.05 μg, 0.005 μg or 0.0005 μg of the FAST protein expression vector (pCAG-p10 or pCAG-ARVp10); and 0.2 μg each of the capping enzyme expression vectors (pCAG-D1R and pCAG-D12L) using a transfection reagent (TransIT-LT1 (trade name), Mirus). The transfection reagent was used in a volume of 2 μL per microgram of DNA. The BHK-T7/P5 cells were cultured in DMEM medium supplemented with 5% FBS, 100 units/mL penicillin and 100 μg/mL streptomycin in an atmosphere of 5% $CO_2$ at 37° C. The medium and the cells were harvested 48 hours after the transfection. The harvested medium and cells were repeatedly freeze-thawed 3 times and used as a virus sample for plaque assay, from which the viral titer was determined.

(7) Plaque Assay

The plaque assay was performed in the following procedure. (a) Seed mouse L929 cells on 6-well culture plates at $1.2\times10^6$ cells/well/2 mL of MEM medium and culture the cells overnight. (b) Add 110 μL of the above virus sample to 1 mL of physiological saline containing gelatin and stir the mixture to prepare a 10-fold diluted solution. Repeat this step to prepare serially diluted virus samples.

(c) Remove the medium from each well and add 100 μL/well of the serially diluted virus samples (two wells per sample). Incubate the plates at room temperature for 60 minutes with occasional agitation.

(d) Add 3 mL/well of prewarmed 2×199 medium/agar (a mixture of equal amounts of 2% agarose and 2×199 medium) and continue incubation at 37° C. for 2 days.

(e) Two days after step (d), overlay 2 mL/well of 2×199 medium/agar and continue incubation at 37° C. for 4 days.

(f) Two days after step (e), overlay 2 mL/well of 2×199 medium/agar containing neutral red and continue incubation at 37° C. overnight.

(g) Count plaques.

Results

The results are shown in FIG. 1. As compared with the viral titer from the cells transfected with only the 4 expression vectors for the RNA genome segments of MRV T1L (pT7-L1-M2T1L, pT7-L2-M3T1L, pT7-L3-S3T1L and pT7-S1-S2-S4-M1T1L), the viral titer from the cells co-transfected with the FAST protein expression vector (pCAG-p10, 0.005 μg) was about 600 times higher. The viral titer from the cells co-transfected with the capping enzyme expression vectors (pCAG-D1R and pCAG-D12L) was about 100 times higher. The viral titer from the cells co-transfected with a combination of the FAST protein expression vector and the capping enzyme expression vectors was about 1,200 times higher. These results show that co-transfection of the RNA genome segment expression vectors with the FAST protein expression vector and/or the capping enzyme expression vectors into the host cells greatly improves the efficiency of artificial recombinant virus production. However, in the case where the DNA amount of the FAST protein expression vector transfected into the host cells was 0.05 μg, the viral titer was undetectable, and in the case of 0.0005 μg, great increase in viral titer was not observed. Therefore, in the case of co-expression with the FAST protein in host cells, the DNA amount of the FAST protein expression vector transfected has to be adjusted so as to ensure an appropriate expression level of the FAST protein.

Also in the case of using pCAG-ARVp10 as the FAST protein expression vector, the results similar to those in FIG. 1 were obtained (data not shown). In addition, the present inventors performed an experiment on the production of an artificial recombinant virus of Mammalian orthoreovirus strain type 3 Dearing (MRV T3D) by co-transfection of expression vectors for the RNA genome segments of MRV T3D (see Non Patent Literature 3) with a FAST protein expression vector and/or capping enzyme expression vectors into host cells. The results confirmed that such co-transfection greatly improved the efficiency of artificial recombinant virus production as with the case of MRV T1L.

The present inventors also performed an experiment on artificial recombinant Nelson Bay reovirus production, and as a result, confirmed that co-transfection of expression vectors for the RNA genome segments of Nelson Bay reovirus with capping enzyme expression vectors into host cells greatly improved the efficiency of artificial recombinant Nelson Bay reovirus production. Nelson Bay reovirus expresses a FAST protein from its own p10 gene.

Example 2: Development of *Rotavirus* Reverse Genetics System

Materials and Methods (1) Virus

Simian rotavirus strain SA11 was used. The present inventors previously determined and registered the nucleotide sequences of all 11 RNA genome segments of this virus strain. The names and GenBank accession numbers of the 11 individual RNA genome segments of the simian rotavirus strain SA11 (hereinafter referred to as "SA11") used in the experiment below are shown in Table 2.

TABLE 2

Sequences of genome segments of simian rotavirus SA11

| Genome segment | Coding protein | GenBank ACCESSION | SEQ ID NO |
|---|---|---|---|
| Segment 1 | VP1 (RNA-dependent RNA polymerase) | LC178564 | 11 |
| Segment 2 | VP2 (RNA-binding protein) | LC178565 | 12 |
| Segment 3 | VP3 (Guanylyltransferase) | LC178566 | 13 |
| Segment 4 | VP4 (Hemagglutinin, spike protein) | LC178567 | 14 |
| Segment 5 | NSP1 (Immune suppressive factor) | LC178570 | 15 |
| Segment 6 | VP6 (Inner capsid) | LC178568 | 16 |
| Segment 7 | NSP3 (Translation enhancer) | LC178572 | 17 |
| Segment 8 | NSP2 (NTPase) | LC178571 | 18 |
| Segment 9 | VP7(Outer capsid) | LC178569 | 19 |
| Segment 10 | NSP4 (Enterotoxin) | LC178573 | 20 |
| Segment 11 | NSP5 (RNA synthesis aid) | LC178574 | 21 |

(2) Preparation of Plasmids Containing Expression Cassettes for Individual RNA Genome Segments (RNA Genome Segment Expression Vectors) of SA11

Plasmids containing cDNAs of the 11 individual RNA genome segments of SA11 were prepared. The specific procedure was as follows. The individual RNA genome segments were amplified by RT-PCR from extracted viral dsRNA as a template using the respective specific primers designed based on the nucleotide sequence of each segment. The RT-PCR products (cDNAs of the individual RNA genome segments) were individually inserted between the T7 promoter sequence and the HDV ribozyme sequence (between positions 30 and 31 of SEQ ID NO: 25) of plasmid p3E5 (3076 bp, SEQ ID NO: 25, shown in FIG. 9) to yield plasmids each containing an expression cassette for the desired RNA genome segment. Each of the expression cassettes for individual RNA genome segments had a structure in which the cDNA of the corresponding segment was flanked by a T7 promoter sequence (SEQ ID NO: 22) at the 5' end and a hepatitis D virus (HDV) ribozyme sequence (SEQ ID NO: 23) at the 3' end, followed by a T7 terminator sequence (SEQ ID NO: 24). The prepared plasmids (RNA genome segment expression vectors) are designated as pT7-VP1SA11, pT7-VP2SA11, pT7-VP3SA11, pT7-VP4SA11, pT7-VP6SA11, pT7-VP7SA11, pT7-NSP1SA11, pT7-NSP2SA11, pT7-NSP3SA11, pT7-NSP4SA11 and pT7-NSP5SA11.

(3) Preparation of Plasmids Having Marker Mutation(s)

Marker mutation was introduced into pT7-NSP1SA11, pT7-NSP2SA11, pT7-NSP3SA11 and pT7-NSP4SA11 using KOD-Plus-Mutagenesis Kit (trade name, Toyobo). More specifically, T at position 1053 of the NSP1 gene (SEQ ID NO: 15) of pT7-NSP1SA11 was mutated to C, and T at position 1059 of the same gene was mutated to C; A at position 409 of the NSP2 gene (SEQ ID NO: 18) of pT7-NSP2SA11 was mutated to T, and T at position 418 of the same gene was mutated to C; A at position 406 of the NSP3 gene (SEQ ID NO: 17) of pT7-NSP3SA11 was mutated to G, and A at position 412 of the same gene was mutated to T; and G at position 389 of the NSP4 gene (SEQ ID NO: 20) of pT7-NSP4SA11 was mutated to A, and A of position 395 of the same gene was mutated to G. These mutations yielded a plasmid having a BamHI recognition sequence at positions 1049 to 1054 of the NSP1 gene (SEQ ID NO: 15), a plasmid having an EcoRV recognition sequence at positions 413 to 418 of the NSP2 gene (SEQ ID NO: 18), a plasmid having an EcoRI recognition sequence at positions 408 to 413 of the NSP3 gene (SEQ ID NO: 17), and a plasmid having a MluI recognition sequence at positions 393 to 398 of the NSP4 gene (SEQ ID NO: 20) (designated as pT7-NSP1SA11/BamHI, pT7-NSP2SA11/EcoRV, pT7-NSP3SA11/EcoRI and pT7-NSP4SA11/MluI, respectively) (see FIG. 2).

(4) FAST Protein Expression Vector

The FAST protein expression vector used was pCAG-p10 (Nelson Bay reovirus p10 expression vector), which was prepared in Example 1.

(5) Capping Enzyme Expression Vector

The capping enzyme expression vectors used were pCAG-D1R (expression vector for the vaccinia virus mRNA capping enzyme large subunit) and pCAG-D12L (expression vector for the vaccinia virus mRNA capping enzyme small subunit), both of which were prepared in Example 1.

(6) Host Cells

The host cells used were the same as those in Example 1, namely BHK-T7/P5 cells, which stably express T7 RNA polymerase.

(7) Production of Artificial Recombinant Viruses

For production of a wild-type artificial recombinant virus, the 11 RNA genome segment expression vectors prepared in the above (2) were used. For production of an artificial recombinant virus (rsSA11) having one marker mutation, pT7-NSP4SA11/MluI was used instead of pT7-NSP4SA11. For production of an artificial recombinant virus (rsSA11-3) having 3 marker mutations, pT7-NSP1SA11/BamHI was used instead of pT7-NSP1SA11, pT7-NSP2SA11/EcoRV was used instead of pT7-NSP2SA11, and pT7-NSP3SA11/EcoRI was used instead of pT7-NSP3SA11.

BHK-T7/P5 cells were seeded on 6-well culture plates at $8 \times 10^5$ cells/well on the previous day of transfection. The BHK-T7/P5 cells were transfected with 0.8 µg each of the 11 RNA genome segment expression vectors; 0.015 µg of the FAST protein expression vector (pCAG-p10); and 0.8 µg each of the capping enzyme expression vectors (pCAG-D1R and pCAG-D12L) using a transfection reagent (TransIT-LT1 (trade name), Mirus). The transfection reagent was used in a volume of 2 µL per microgram of DNA. The BHK-T7/P5 cells were cultured in DMEM medium supplemented with 5% FBS, 100 units/mL penicillin and 100 µg/mL streptomycin in an atmosphere of 5% $CO_2$ at 37° C. The medium and the cells were harvested 48 hours after the transfection. The harvested medium and cells were repeatedly freeze-thawed 3 times to prepare a cell lysate, and the cell lysate was added to monkey MA104 cells (ATCC CRL-2378.1) for passage. More specifically, about 0.5 mL of the cell lysate was added to confluent MA104 cells on 12-well plates in the presence of 0.5 µg/mL trypsin. The MA104 cells were cultured in DMEM medium without FBS. In the case where the cells showed cytopathic changes during the 7 days of culture after the passage, artificial recombinant virus production was judged as successful. In this example, cytopathic changes were observed in the cells transfected with the expression vectors for wild-type SA11, rsSA11 or rsSA11-3 production, and therefore, the production of each type of artificial recombinant rotavirus was judged as successful.

(8) Confirmation of Marker Mutation

The medium and cells in the wells in which cytopathic changes were shown were harvested and then repeatedly freeze-thawed 3 times to prepare a cell lysate. From the cell lysate containing wild-type SA11, rsSA11 or rsSA11-3, viral genome RNA was extracted using the Trizol reagent (Thermo Scientific). Using the extracted RNA as a template, RT-PCR was performed with specific primers designed based on the nucleotide sequences of the RNA genome segments. SuperScript III Reverse Transcriptase (Thermo Scientific) was used as the reverse transcriptase. The amplified products of NSP1, NSP2 and NSP3 of wild-type SA11 were digested with BamHI, EcoRV and EcoRI, respectively. The amplified products of NSP1, NSP2 and NSP3 of rsSA11-3 were also digested in the same manner. The digestion products were subjected to 1.2% agarose gel electrophoresis. The amplified products of NSP4 of wild-type SA11 and rsSA11 were digested with MluI, and the digestion products were subjected to 1.2% agarose gel electrophoresis.

Results

Figure 3:
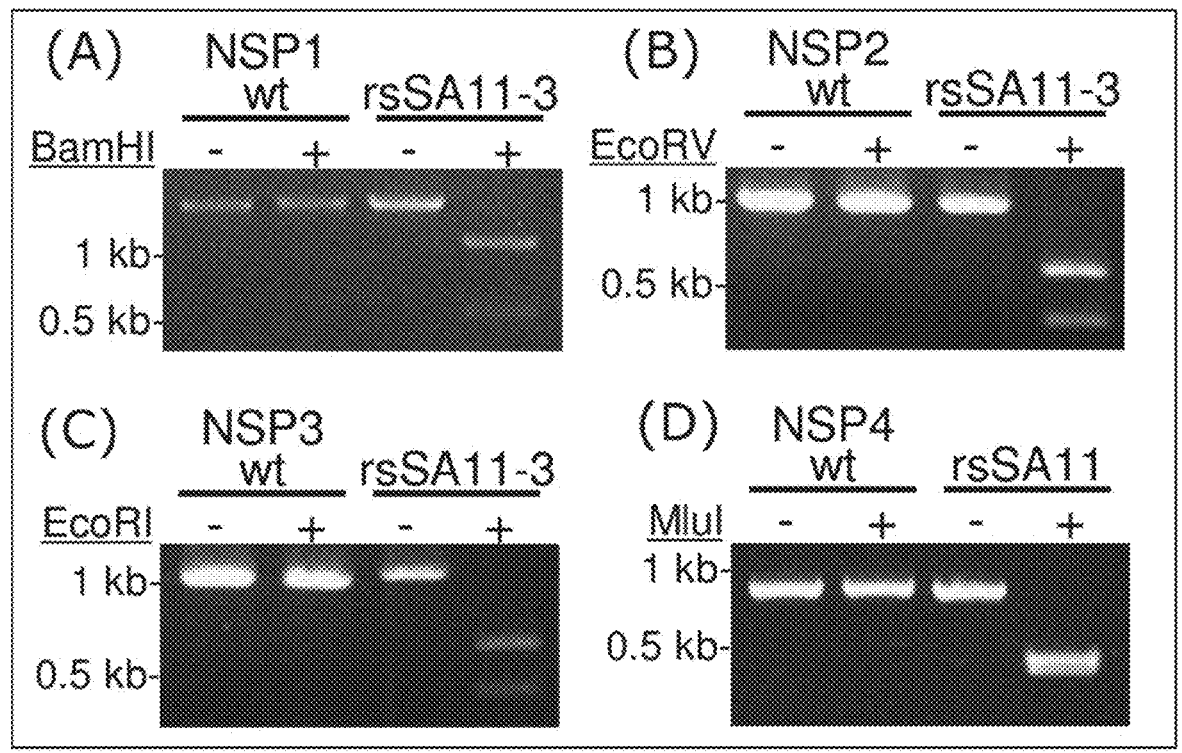
FIG. 3 shows the results confirming that the viruses produced using a rotavirus reverse genetics system have a marker mutation(s).

The results are shown in FIGS. 3A to 3D. FIG. 3A shows an electrophoretic pattern of BamHI-digested amplified products of wild-type SA11 NSP1 and rsSA11-3 NSP1. FIG. 3B shows an electrophoretic pattern of EcoRV-digested amplified products of wild-type SA11 NSP2 and rsSA11-3 NSP2. FIG. 3C shows an electrophoretic pattern of EcoRI-digested amplified products of wild-type SA11 NSP3 and rsSA11-3 NSP3. FIG. 3D shows an electrophoretic pattern of MluI-digested amplified products of wild-type SA11 NSP4 and rsSA11-3 NSP4. The results confirmed that the genome RNAs of rsSA11-3 and rsSA11 had marker mutation(s) and was digested with the corresponding restriction enzyme(s). Therefore, the viruses obtained using the rotavirus reverse genetics system of this example were proven to be artificial recombinant rotaviruses derived from the RNA genome segment expression vectors.

Example 3: Production of Artificial Recombinant *Rotavirus* Having a Deletion Mutation An experiment was performed to examine the feasibility of the production of an artificial recombinant rotavirus having a partial deletion mutation in NSP1, a suppressive factor against host innate immune responses.

Figure 4:
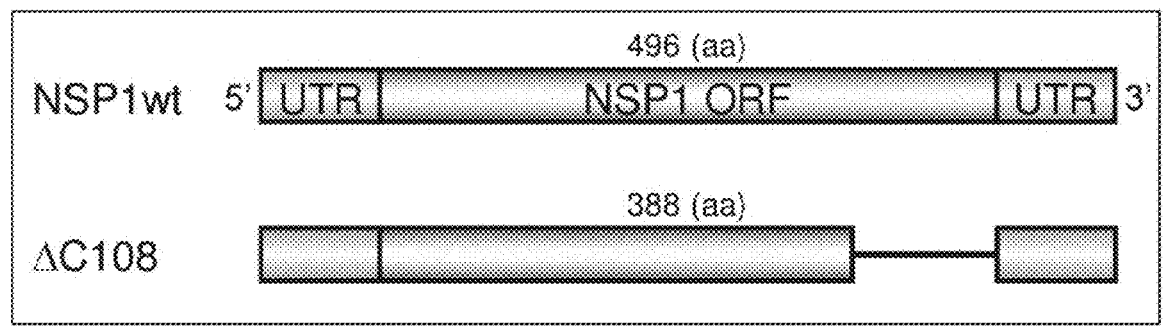
FIG. 4 shows the structures of a wild-type NSP1 gene and a deletion mutant of the NSP1 gene.

Materials and Methods (1) Preparation of Plasmid Having a Deletion Mutation in NSP1 Gene A plasmid having a mutated NSP1 gene (see FIG. 4), which had a 299-base deletion at positions 1192 to 1490 of the NSP1 gene (SEQ ID NO: 15), was prepared from pT7-NSP1SA11 as a template using KOD-Plus-Mutagenesis Kit (trade name, Toyobo) and specific primers for the gene. This plasmid (designated as pT7-NSP1SA11ΔC108) expresses an NSP1 protein having a deletion of C-terminal 108 amino acids of the native NSP1.

(2) Production of Artificial Recombinant Viruses and Confirmation of Mutation

A deletion mutant of rotavirus (rsSA11/NSP1ΔC108) was produced in the same manner as in Example 2 except that pT7-NSP1SA11ΔC108 was used instead of pT7-NSP1SA11 in the set of the 11 RNA genome segment expression vectors prepared in Example 2 (2). A wild-type artificial recombinant virus was also produced in the same manner as in Example 2. The medium and MA104 cells in the wells in which cytopathic changes were shown were harvested and then repeatedly freeze-thawed 3 times to prepare a cell lysate. From the cell lysate containing rsSA11/NSP1ΔC108 or wild-type SA11, viral genome RNA was extracted and then subjected to SDS-PAGE.

Results

Figure 5:
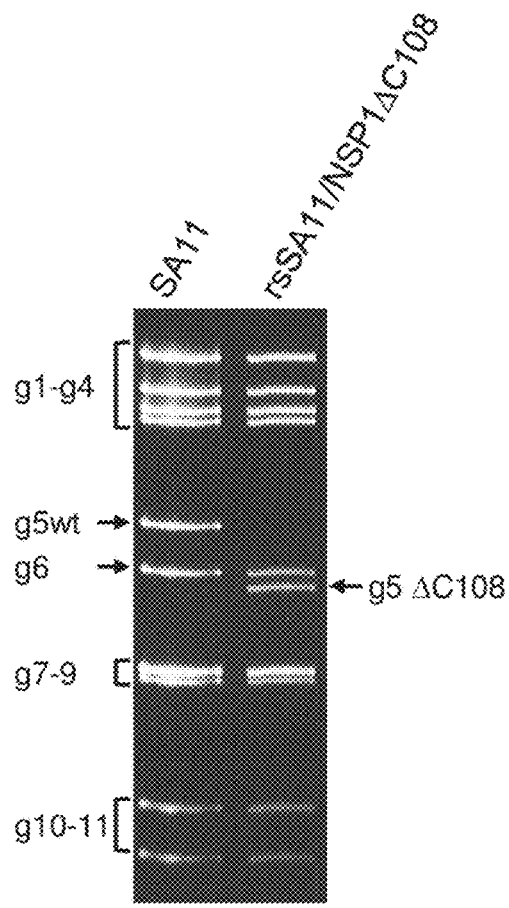
FIG. 5 shows the results of SDS-PAGE of the RNA genome segments of a wild-type artificial recombinant virus and an artificial recombinant virus having a deletion mutant of the NSP1 gene.

The results are shown in FIG. 5. As is clear from FIG. 5, the band of each RNA genome segment of rsSA11/NSP1ΔC108 was observed at the same position as the corresponding band of a wild-type artificial recombinant virus, except for NSP1. The position of the band of NSP1ΔC108 was different from that of the wild-type counterpart, showing that the NSP1ΔC108 genome RNA is shorter than the wild-type counterpart. Since the C-terminal region of NSP1 is important for suppression of innate immunity, the mutant rotavirus produced in this example is a replication-competent attenuated virus and can be a promising vaccine candidate.

Example 4: Production of Luciferase-Expressing *Rotavirus*

An experiment was performed to examine the feasibility of the production of a foreign gene-expressing rotavirus for use as a vaccine vector.

Figure 6:
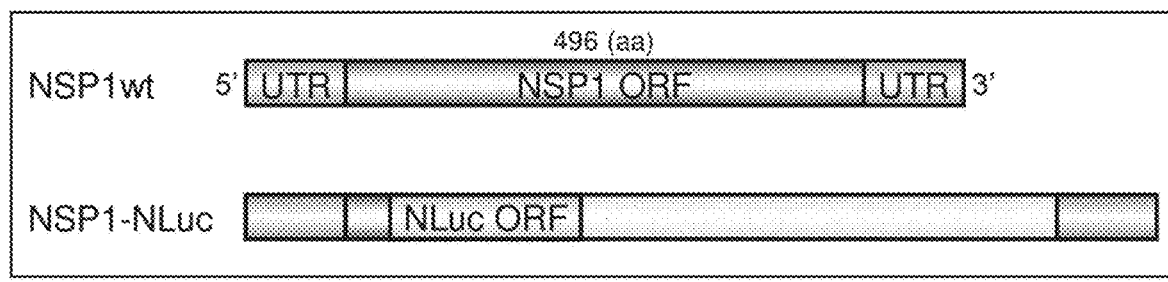
FIG. 6 shows the structures of a wild-type NSP1 gene and an NSP1 gene having a luciferase gene insertion.

Materials and Methods (1) Preparation of NSP1 Expression Plasmid Having a Luciferase Gene Insertion The Nluc gene, which is a luciferase gene of *Oplophorus gracilirostris*, was used as the luciferase gene. The Nluc protein-coding region at positions 815 to 1330 (SEQ ID NO: 31) of vector pNL1.1 (Promega, GenBank ACCESSION: KM359774, 3817 bp) was amplified by PCR. The amplified product was inserted between positions 128 and 129 of the NSP1 gene (SEQ ID NO: 15) of pT7-NSP1SA11 to prepare an NSP1 gene expression plasmid having a luciferase gene insertion (designated as pT7-NSP1SA11-Nluc) (see FIG. 6).

(2) Production of Artificial Recombinant Virus and Confirmation of Luciferase Expression A luciferase-expressing rotavirus was produced in the same manner as in Example 2 except that pT7-NSP1SA11-Nluc was used instead of pT7-NSP1SA11 in the set of the 11 RNA genome segment expression vectors prepared in Example 2 (2). After 7 days from passage in MA104 cells, the medium and the cells were harvested and then freeze-thawed 3 times to prepare a cell lysate. The cell lysate was subjected to plaque assay. For the plaque assay, CV-1 cells (ATCC CCL-70) were used. The CV-1 cells were cultured in DMEM medium without FBS. The MA104 cell lysate was serially diluted 10-fold, and each serial dilution was added to confluent CV-1 cells on 12-well plates for viral infection. After incubation for 60 minutes, the medium was removed, and DMEM medium containing 0.8% agarose gel and 0.5 μg/mL trypsin was overlaid on the cells. Four days after viral infection, luminescence from plaques was examined. More specifically, the substrate stock solution of Nano-Glo Luciferase Assay System (trade name, Promega) was diluted about 500-fold with DMEM medium without FBS and added to each well, and luminescence was detected with an in vivo imaging system (IVIS Spectrum, manufactured by Xenogen). Then, the cells were fixed with 10% formaldehyde and stained with crystal violet to visualize plaques.

Results

Figure 7:
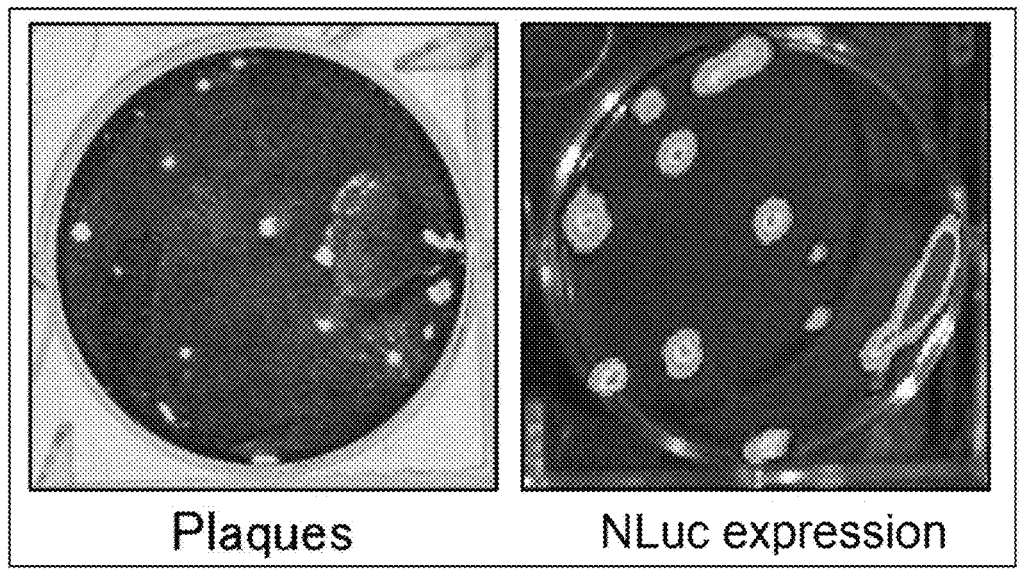
FIG. 7 shows the results of plaque assay of an artificial recombinant rotavirus expressing luciferase (left) and the results of luminescence detection in plaques (right).

The results are shown in FIG. 7. The left panel is an image of plaques visualized by crystal violet staining of cells, and the right panel is a luminescent image of the same well. The positions of plaques were the same to those of luminescent signals, showing that an artificial recombinant rotavirus expressing a luciferase gene had been produced. These results demonstrate that the insertion of a foreign gene into the rotavirus genome is feasible, and the artificial recombinant rotavirus obtained in this example can be used as a vaccine vector. In addition to the NSP1 gene, the NSP3 gene (Montero H, Arias C F, Lopez S. *Rotavirus* Nonstructural Protein NSP3 Is Not Required for Viral Protein Synthesis. Journal of Virology. 2006; 80(18):9031-9038. doi:10.1128/JVI.00437-06) can be used as the foreign gene insertion site in the production of foreign gene-expressing viruses capable of autonomous proliferation.

Example 5: Production of Artificial Recombinant Rotaviruses Using FAST Protein Expression Vector or Capping Enzyme Expression Vectors Materials and Methods The expression vectors for the 11 RNA genome segments of simian rotavirus strain SA11 produced in "Materials and methods" (2) of Example 2, the FAST protein expression vector pCAG-p10 produced in "Materials and methods" (3) of Example 1, the capping enzyme expression vectors pCAG-D1R and pCAG-D12L produced in "Materials and methods" (4) of Example 1 were variously combined as shown in Table 3 and transfected into BHK-T7/P5 cells (see Example 1) to examine whether artificial recombinant rotaviruses could be produced. The specific procedure was as follows. BHK-T7/P5 cells were seeded on 12-well culture plates at $4\times10^5$ cells/well on the previous day of transfection. The BHK-T7/P5 cells were transfected with the above vectors in the combinations and DNA amounts described in Table 3 using a transfection reagent (TransIT-LT1 (trade name), Mirus). Two days later, MA104 cells ($4\times10^4$ cells/well) were added, and culture was continued for 3 days. The medium and the cells were harvested and then repeatedly freeze-thawed 3 times to prepare a cell lysate. About 0.5 mL of the cell lysate was added to confluent MA104 cells on 12-well plates in the presence of 0.5 μg/mL trypsin, and culture was continued for 7 days.

TABLE 3

| Vector name | Group A DNA amount (μg) | Group B DNA amount (μg) | Group C DNA amount (μg) |
|---|---|---|---|
| pT7-SA11-VP1 | 0.25 | 0.25 | 0.25 |
| pT7-SA11-VP2 | 0.25 | 0.25 | 0.25 |
| pT7-SA11-VP3 | 0.25 | 0.25 | 0.25 |
| pT7-SA11-VP4 | 0.25 | 0.25 | 0.25 |
| pT7-SA11-VP5 | 0.25 | 0.25 | 0.25 |
| pT7-SA11-VP6 | 0.25 | 0.25 | 0.25 |
| pT7-SA11-VP7 | 0.25 | 0.25 | 0.25 |
| pT7-SA11-NSP1 | 0.25 | 0.25 | 0.25 |
| pT7-SA11-NSP2 | 0.25 | 0.25 | 0.25 |
| pT7-SA11-NSP3 | 0.25 | 0.25 | 0.25 |
| pT7-SA11-NSP4 | 0.25 | 0.25 | 0.25 |
| pT7-SA11-NSP5 | 0.25 | 0.25 | 0.25 |
| pCAG-D1R | 0.25 | — | 0.25 |
| pCAG-D12L | 0.25 | — | 0.25 |
| pCAG-p10 | — | 0.001 | 0.001 |

Results

Cytopathic changes were observed in all groups, namely group A, in which only the capping enzyme expression vectors were co-expressed with the 11 RNA genome segment expression vectors; group B, in which only the FAST protein expression vector was co-expressed with the 11 RNA genome segment expression vectors; and group C, in which a combination of the capping enzyme expression vectors and the FAST protein expression vector was co-expressed with the 11 RNA genome segment expression vectors. That is, co-expression of the 11 RNA genome segment expression vectors even with capping enzyme expression vectors only or a FAST protein expression vector only allows the production of artificial recombinant rotaviruses.

Example 6: Enhancement of Replication Capacity of Mammalian *Orthoreovirus* (MRV) and *Rotavirus* (RV) by FAST Protein Materials and Methods Confluent Vero cells on 24-well plates were transfected with the FAST protein expression vector (pCAG-p10) or a pCAG empty vector in an amount of 0, 0.25, 0.5, 1 or 2 μg. TransIT-LT1 (trade name, Mirus) was used as the transfection reagent. Two hours later, the medium was replaced with fresh DMEM with 5% FBS, and the Vero cells were infected with Mammalian orthoreovirus (MRV T1L) or simian rotavirus (SA11) at an MOI of 0.001. After viral adsorption at 37° C. for 1 hour, the cells were washed 6 times with PBS. The MRV-infected cells were cultured in DMEM with 5% FBS, and the RV-infected cells were cultured in FBS-free DMEM. After 16 hours of infection, the medium and the cells were harvested and then freeze-thawed 3 times to prepare a cell lysate. The cell lysate was subjected to plaque assay. The plaque assay was performed in the same manner as in Example 1.

Results

Figure 8:
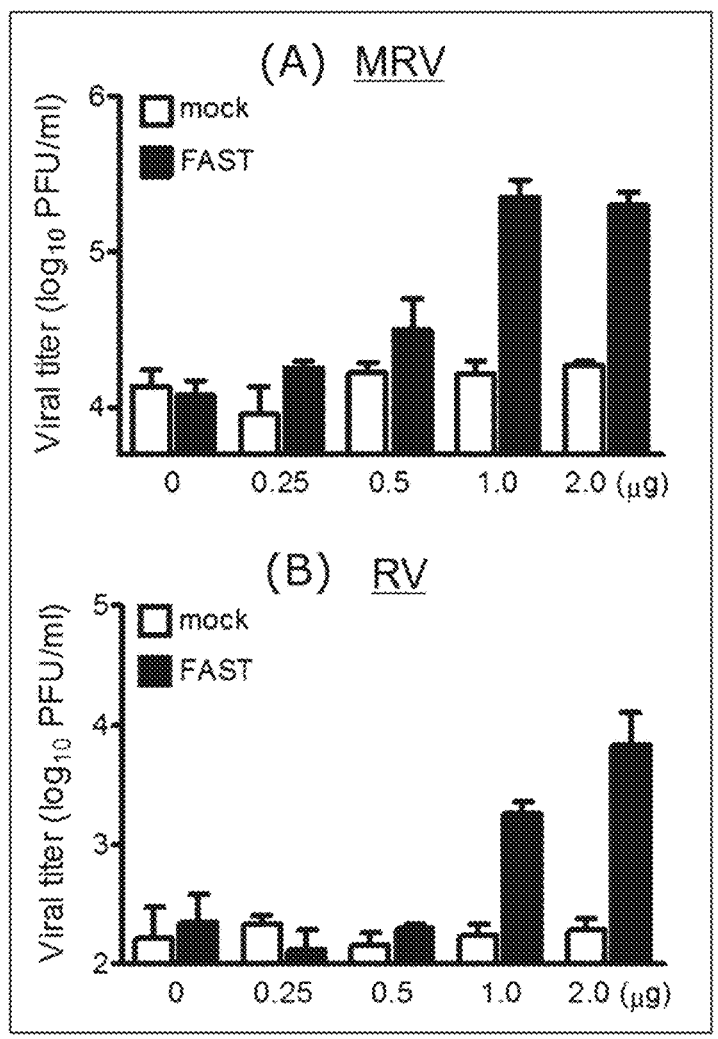
FIG. 8 shows the results confirming that the replication capability of Mammalian orthoreovirus (MRV) and rotavirus (RV) was enhanced by using host cells transfected with a FAST protein expression vector.

The results are shown in FIGS. 8A and 8B. FIG. 8A shows the results for MRV and FIG. 8B shows the results for RV. The replication capability of MRV was enhanced as result of transfection of 0.5 μg or more of pCAG-p10 as compared with the empty vector (mock). The replication capability of RV was enhanced as result of transfection of 1 μg or more of pCAG-p10 as compared with the empty vector (mock). These results show that viral replication capability is improved by using FAST protein-expressing cells as host cells.

Example 7: Production of Mono-Reassortant Rotavirus Between Simian Rotavirus and Human Rotavirus An experiment was performed to examine the feasibility of the production of an artificial recombinant rotavirus (SA11/KUNSP4) which was derived from simian rotavirus and had a human rotavirus NSP4 gene as the NSP4 gene segment.

Materials and Methods (1) Human Rotavirus
Human rotavirus strain KU (Urasawa, S., Urasawa, T., Taniguchi, K., and Chiba, S. (1984). Serotype determination of human rotavirus isolates and antibody prevalence in pediatric population in Hokkaido, Japan. Archives of virology 81, 1-12) was used.
(2) Preparation of Plasmid Having a Human Rotavirus NSP4 Gene
A plasmid containing a cDNA of the NSP4 segment of the KU RNA genome (GenBank ACCESSION: AB022772, SEQ ID NO: 32) was prepared. The specific procedure was as follows. The NSP4 segment of the human rotavirus RNA genome was amplified by RT-PCR from extracted viral dsRNA as a template using specific primers designed based on the nucleotide sequence of the segment. The RT-PCR product (cDNA of the NSP4 segment of the RNA genome) was inserted between the T7 promoter sequence and the HDV ribozyme sequence (between positions 30 and 31 of SEQ ID NO: 25) of plasmid p3E5 (3076 bp, SEQ ID NO: 25, shown in FIG. 9) to yield a plasmid containing an expression cassette for the NSP4 segment of the RNA genome. The expression cassette for the NSP4 segment of the RNA genome had a structure in which the cDNA of the NSP4 segment was flanked by a T7 promoter sequence (SEQ ID NO: 22) at the 5' end and a hepatitis D virus (HDV) ribozyme sequence (SEQ ID NO: 23) at the 3' end, followed by a T7 terminator sequence (SEQ ID NO: 24). The prepared plasmid is designated as pT7-NSP4KU.
(3) Production of Artificial Recombinant Virus and Confirmation of Mutation
An NSP4 mono-reassortant rotavirus (SA11/KUNSP4) was produced in the same manner as in Example 2 except that pT7-NSP4KU was used instead of pT7-NSP4SA11 in the set of the 11 RNA genome segment expression vectors prepared in Example 2 (2). The medium and MA104 cells in the wells in which cytopathic changes were shown were harvested and then repeatedly freeze-thawed 3 times to prepare a cell lysate. Viral genome RNA was extracted from SA11/KUNSP4 and then subjected to SDS-PAGE together with viral genome RNAs extracted from wild-type SA11 and wild-type KU.

Results

Figure 11:
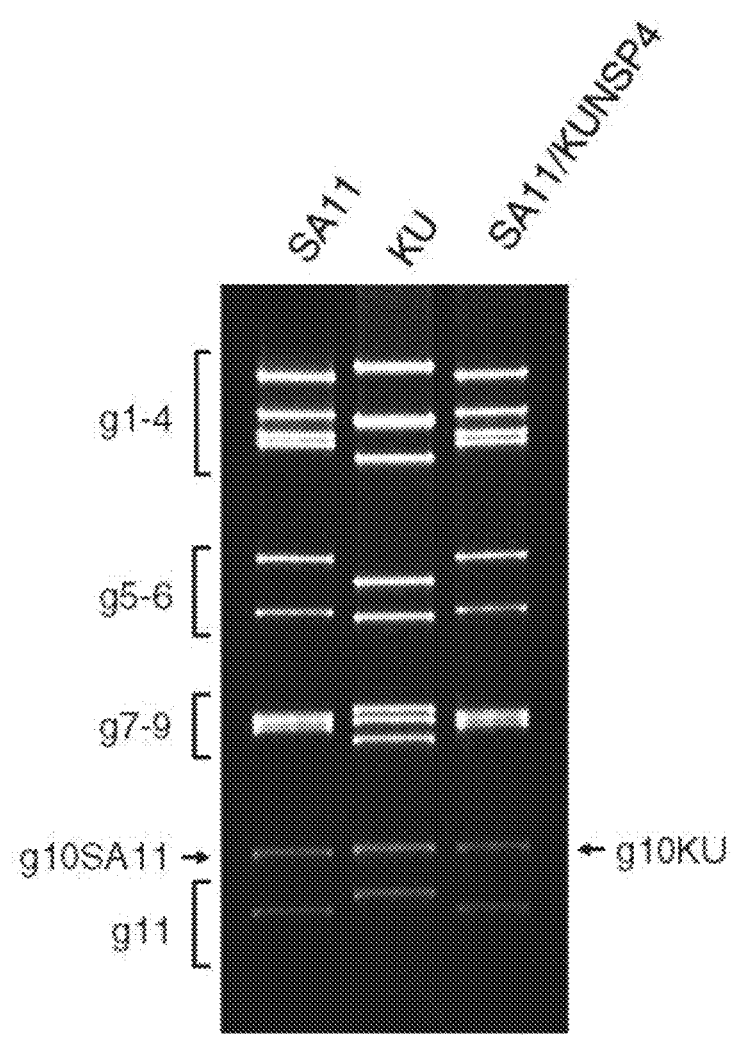
FIG. 11 shows the results of SDS-PAGE of the RNA genome segments of an artificial recombinant simian rotavirus having the NSP4 segment of the human rotavirus RNA genome, the RNA genome segments of a wild-type human rotavirus, and the RNA genome segments of a wild-type simian rotavirus.

The results are shown in FIG. 11. As is clear from FIG. 11, the band of each RNA genome segment of SA11/KUNSP4 was observed at the same position as the corresponding band of wild-type SA11, except for NSP4 ("g10KU" in the figure). The band of the NSP4 segment of SA11/KUNSP4 was observed at the same position as the band of the NSP4 segment of wild-type KU. These results show that the production method of the present invention allows the production of reassortant rotaviruses in which RNA genome segments of rotaviruses of various animal species are freely combined.

Example 8: Screening Test for Anti-Rotavirus Drug Using Luciferase-Expressing Rotavirus An experiment was performed to examine the visualization of the rotavirus proliferation inhibitory effect of a known anti-rotavirus drug, ribavirin (Smee, D. F., Sidwell, R. W., Clark, S. M., Barnett, B. B., and Spendlove, R. S. (1982). Inhibition of rotaviruses by selected antiviral substances: mechanisms of viral inhibition and in vivo activity. Antimicrobial agents and chemotherapy 21, 66-73) using the luciferase-expressing artificial recombinant rotavirus produced in Example 4.

Materials and Methods

CV-1 cells were seeded on 96-well culture plates at $1 \times 10^5$ cells/well on the previous day of infection. The CV-1 cells were infected with wild-type SA11 or the luciferase-expressing artificial recombinant rotavirus produced in Example 4 at an MOI of 0.001. After viral adsorption at 37° C. for 1 hour, the culture supernatant was removed, and DMEM (without FBS and with 0.5 μg/mL trypsin) containing 0, 1, 5, 10, 50, 100 or 200 μM ribavirin (Sigma-Aldrich) was added. Incubation was performed at 37° C. for 14 hours. After that, the substrate stock solution of Nano-Glo Luciferase Assay System (trade name, Promega) was added to the culture medium, and luminescence was detected with an in vivo imaging system (IVIS Spectrum, manufactured by Xenogen).

Results

Figure 12:
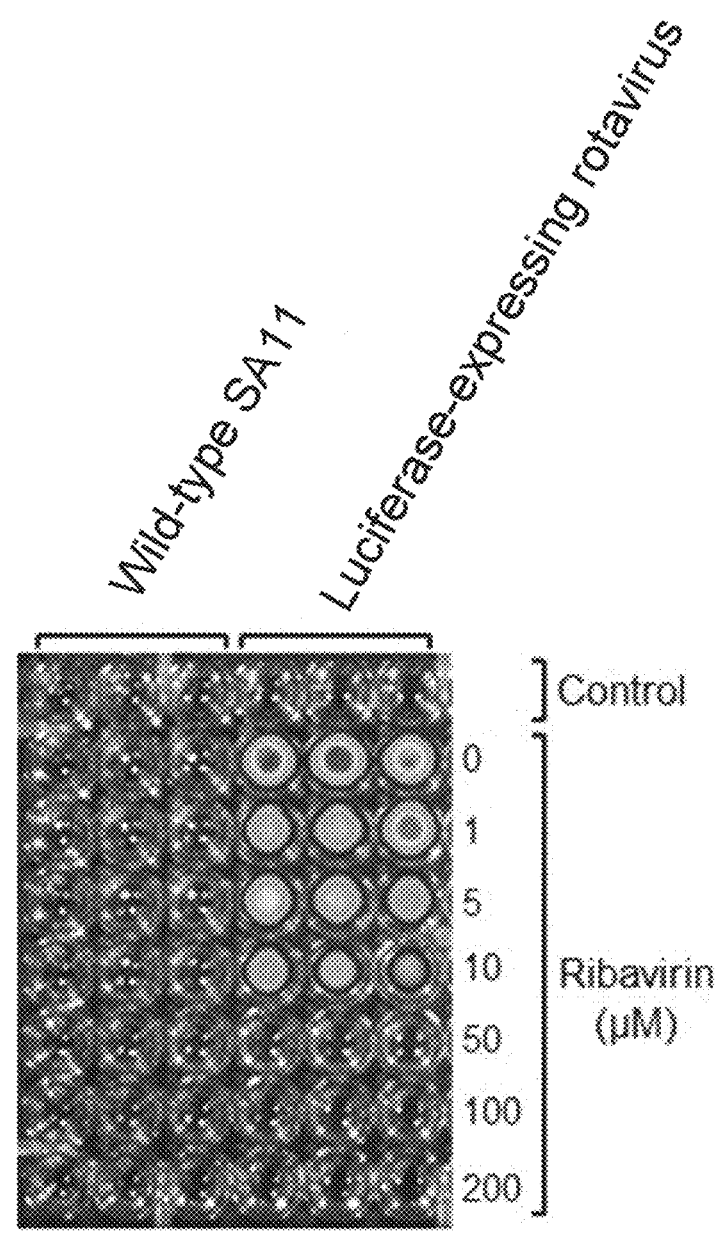
FIG. 12 shows the results of the viral proliferation inhibitory effect of an anti-rotavirus drug, ribavirin, assessed based on luminescence intensity measured in a test using a luciferase-expressing artificial recombinant rotavirus.

The results are shown in FIG. 12. As is clear from FIG. 12, the luminescence intensity in the wells with ribavirin decreased in a ribavirin concentration-dependent manner, and no luminescence was observed in the wells with ribavirin at concentrations of 50 μM or more. These results show that the extent of viral proliferation can be easily visualized using the luciferase-expressing artificial recombinant rotavirus. Therefore, the luciferase-expressing artificial recombinant rotavirus can be useful in screening for unidentified anti-rotavirus drugs.

Example 9: Improvement of Rotavirus Reverse Genetics System (1)

To improve the rotavirus RG system by which artificial recombinant rotaviruses were successfully produced in Example 2, a system using overexpression of an NSP2 gene product and an NSP5 gene product was evaluated in terms of the efficiency of artificial recombinant rotavirus production.

Materials and Methods

The RNA genome segment expression vectors, the FAST protein expression vector and the capping enzyme expression vectors used in this example were the same as those in Example 2.

For preparation of an NSP2 expression vector and an NSP5 expression vector, the protein-coding region DNA of the NSP2 gene of simian rotavirus SA11 (GenBank ACCESSION: LC178571, SEQ ID NO: 18) and the protein-coding region DNA of the NSP5 gene of the same strain (GenBank ACCESSION: LC178574, SEQ ID NO: 21) were individually inserted into the plasmid pCAGGS shown in FIG. 10. These coding region DNAs were synthesized by custom gene synthesis services (Eurofins Genomics). These synthetic DNAs were individually inserted into the EcoRI restriction site of plasmid pCAGGS to yield pCAG-NSP2 and pCAG-NSP5.

The host cells used were BHK-T7/P5 cells, which stably express T7 RNA polymerase. The BHK-T7/P5 cells were prepared by transfecting BHK cells (Baby Hamster Kidney Cells) with a plasmid pCAGGS having a T7 RNA polymerase-encoding DNA inserted downstream of the CAG promoter and subsequently culturing the BHK cells in an antibiotic-containing medium for selection.

BHK-T7/P5 cells were seeded on 24-well culture plates at $2 \times 10^5$ cells/well on the previous day of transfection. The BHK-T7/P5 cells were transfected with the RNA genome segment expression vectors (pT7-VP1SA11, pT7-VP2SA11, pT7-VP3SA11, pT7-VP4SA11, pT7-VP6SA11, pT7-VP7SA11, pT7-NSP1SA11, pT7-NSP2SA11, pT7-NSP3SA11, pT7-NSP4SA11 and pT7-NSP5SA11); the FAST protein expression vector (pCAG-FAST p10); the capping enzyme expression vectors (pCAG-D1R and pCAG-D12L); the NSP2 expression vector (pCAG-NSP2); and the NSP5 expression vector (pCAG-NSP5) in the combinations and DNA amounts described in Table 4 using a transfection reagent (TransIT-LT1 (trade name), Mirus). The transfection reagent was used in a volume of 2 µL per microgram of DNA.

TABLE 4

| Vector name | Group A DNA amount (µg) | Group B DNA amount (µg) | Group C DNA amount (µg) | Group D DNA amount (µg) |
| --- | --- | --- | --- | --- |
| pT7-VP1SA11 | 0.125 | 0.125 | 0.125 | 0.125 |
| pT7-VP2SA11 | 0.125 | 0.125 | 0.125 | 0.125 |
| pT7-VP3SA11 | 0.125 | 0.125 | 0.125 | 0.125 |
| pT7-VP4SA11 | 0.125 | 0.125 | 0.125 | 0.125 |
| pT7-VP5SA11 | 0.125 | 0.125 | 0.125 | 0.125 |
| pT7-VP6SA11 | 0.125 | 0.125 | 0.125 | 0.125 |
| pT7-VP7SA11 | 0.125 | 0.125 | 0.125 | 0.125 |
| pT7-NSP1SA11 | 0.125 | 0.125 | 0.125 | 0.125 |
| pT7-NSP2SA11 | 0.125 | 0.125 | 0.125 | 0.125 |
| pT7-NSP3SA11 | 0.125 | 0.125 | 0.125 | 0.125 |
| pT7-NSP4SA11 | 0.125 | 0.125 | 0.125 | 0.125 |
| pT7-NSP5SA11 | 0.125 | 0.125 | 0.125 | 0.125 |
| pCAG-FAST | 0.001 | 0.001 | 0.001 | 0.001 |
| pCAG-D1R | 0.125 | 0.125 | 0.125 | 0.125 |
| pCAG-D12L | 0.125 | 0.125 | 0.125 | 0.125 |
| PCAG-NSP2 | — | 0.125 | — | 0.125 |
| pCAG-NSP5 | — | — | 0.125 | 0.125 |

The BHK-T7/P5 cells were cultured in DMEM medium supplemented with 5% FBS, 100 units/mL penicillin and 100 µg/mL streptomycin in an atmosphere of 5% $CO_2$ at 37° C. The medium and the cells were harvested 48 hours after the transfection. The harvested medium and cells were repeatedly freeze-thawed 3 times to prepare a cell lysate, and the cell lysate was added to monkey MA104 cells (ATCC CRL-2378.1) for passage. More specifically, about 0.5 mL of the cell lysate was added to confluent MA104 cells on 12-well plates in the presence of 0.5 µg/mL trypsin. The MA104 cells were cultured in DMEM medium without FBS. In the case where the cells showed cytopathic changes during the 7 days of culture after the passage, artificial recombinant rotavirus production was judged as successful.

Results

The results are shown in Table 5.

TABLE 5

| | Group A | Group B | Group C | Group D |
| --- | --- | --- | --- | --- |
| Wells with cytopathic changes/total wells | 2/24 | 6/24 | 2/24 | 16/24 |

Cytopathic changes were observed in all groups, namely group A, in which the capping enzyme expression vectors and the FAST protein expression vector were co-expressed with the 11 rotavirus genome segment expression plasmids, group B, in which the capping enzyme expression vectors, the FAST protein expression vector and the NSP2 expression vector were co-expressed with the 11 rotavirus genome segment expression plasmids, group C, in which the capping enzyme expression vectors, the FAST protein expression vector and the NSP5 expression vector were co-expressed with the 11 rotavirus genome segment expression plasmids, and group D, in which the capping enzyme expression vectors, the FAST protein expression vector, the NSP2 expression vector and the NSP5 expression vector were co-expressed with the 11 rotavirus genome segment expression plasmids. These results confirmed successful production of artificial recombinant rotaviruses. The production efficiency was 3 times higher in group B than in group A, equal between group C and group A, and 8 times higher in group D than in group A. These results show that the overexpression of an NSP2 gene product and/or an NSP5 gene product improves production efficiency.

Example 10: Improvement of *Rotavirus* Reverse Genetics System (2)

An experiment was performed to examine the feasibility of rotavirus production without using a FAST protein expression vector or capping enzyme expression vectors.

Materials and Methods

The RNA genome segment expression vectors, the NSP2 expression vector, the NSP5 expression vector, the transfection reagent and the host cells used in this example were the same as those in Example 9. BHK-T7/P5 cells were seeded on 12-well culture plates at $4 \times 10^5$ cells/well on the previous day of transfection. The BHK-T7/P5 cells were transfected with the above vectors in the combinations and DNA amounts described in Table 6. The transfection reagent was used in a volume of 2 µL per microgram of DNA. The culture of the BHK-T7/P5 cells and the passage in monkey MA104 cells were performed in the same manner as in Example 9. In the case where the cells showed cytopathic changes during the 7 days of culture after the passage, artificial recombinant rotavirus production was judged as successful.

TABLE 6

| Vector name | Group X<br>DNA amount<br>(μg) | Group Y<br>DNA amount<br>(μg) |
|---|---|---|
| pT7-VP1SA11 | 0.25 | 0.25 |
| pT7-VP2SA11 | 0.25 | 0.25 |
| pT7-VP3SA11 | 0.25 | 0.25 |
| pT7-VP4SA11 | 0.25 | 0.25 |
| pT7-VP5SA11 | 0.25 | 0.25 |
| pT7-VP6SA11 | 0.25 | 0.25 |
| pT7-VP7SA11 | 0.25 | 0.25 |
| pT7-NSP1SA11 | 0.25 | 0.25 |
| PT7-NSP2SA11 | 0.25 | 0.75 |
| PT7-NSP3SA11 | 0.25 | 0.25 |
| PT7-NSP4SA11 | 0.25 | 0.25 |
| PT7-NSP5SA11 | 0.25 | 0.75 |
| pCAG-NSP2 | 0.25 | — |
| pCAG-NSP5 | 0.25 | — |

Results

In the case of overexpression of the NSP2 gene product and the NSP5 gene product, an artificial recombinant rotavirus was successfully produced even without transfection of the capping enzyme expression vectors or the FAST protein expression vector into the host cells. As a means for the overexpression of the NSP2 gene product and the NSP5 gene product, transfection of the NSP2 expression vector and the NSP5 expression vector in addition to the RNA genome segment expression vectors as shown in group X was proven to be useful, and also transfection of increased DNA amounts of the expression vectors for RNA genome segments encoding NSP2 and NSP5 as shown in group Y was proven to be useful. In particular, the results of group Y demonstrate that an artificial recombinant rotavirus can be produced by transfecting only the 11 rotavirus RNA genome segment expression vectors into host cells and subsequently culturing the cells.

Example 11: Production of Artificial Recombinant Attenuated Virus Utilizing Mutation in NSP4 Protein An experiment was performed to examine the feasibility of the production of an artificial recombinant attenuated rotavirus by introducing an artificial amino acid mutation into NSP4.

Materials and Methods (1) Preparation of Plasmid Having an Amino Acid Mutation in NSP4 Gene A plasmid having a mutated NSP4 gene, in which the cytosine (C) at position 55 of the NSP4 gene (SEQ ID NO: 20) was substituted with glycine (G), was prepared from pT7-NSP4SA11 (see Example 2) as a template using KOD-Plus-Mutagenesis Kit (trade name, Toyobo) and specific primers for the gene. This plasmid (designated as pT7-NSP4SA11-L5S) expresses a mutant NSP4 protein having serine (S) in place of the leucine (L) at residue 5 of the native NSP4 protein.

(2) Production of Artificial Recombinant Virus Having a Mutation in NSP4

An artificial recombinant rotavirus having a mutation in NSP4 (rsSA11/NSP4-L5S) was produced in the same manner as in Example 2 except that pT7-NSP4SA11-L5S was used instead of pT7-NSP1SA11 in the set of the 11 RNA genome segment expression vectors prepared in Example 2 (2). A wild-type artificial recombinant rotavirus (wild-type SA11) was also produced in the same manner as in Example 2.

(3) Confirmation of Replication Capability of Artificial Recombinant *Rotavirus* Having a Mutation in NSP4

Confluent MA104 cells on 12-well plates were infected with rsSA11/NSP4-L5S or wild-type SA11 at an MCI of 0.01. After viral adsorption at 37° C. for 1 hour, the cells were washed once with PBS and then cultured in FBS-free DMEM supplemented with 0.5 μg/mL trypsin. After 48 hours of infection, the medium and the cells were harvested and then freeze-thawed 3 times to prepare a cell lysate. The cell lysate was subjected to plaque assay. The plaque assay was performed in the same manner as in Example 1.

Results

Figure 13:
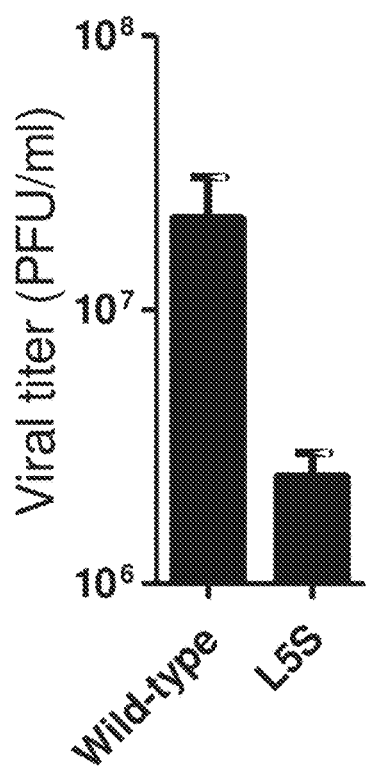
FIG. 13 shows the comparison of the replication capabilities of an artificial recombinant rotavirus having a mutation in NSP4 and a wild-type artificial recombinant rotavirus.

The results are shown in FIG. 13. The proliferation capacity of rsSA11/NSP4-L5S was 8.7 times lower than that of wild-type SA11 (21500000 vs 2450000). There has been no report on the production of attenuated rotaviruses utilizing artificial mutation in NSP4. The NSP4 mutant rotavirus produced in this example is a replication-competent attenuated virus and can be a promising vaccine candidate.

In addition, the present inventors confirmed that the rotavirus having a deletion mutation in NSP1 (rsSA11/NSP1ΔC108) produced in Example 3 and a separately-produced rotavirus having a deletion mutation in NSP3 also had a lower proliferation capacity as compared with the wild-type rotavirus (data not shown). Therefore, artificial recombinant rotaviruses having an artificial mutation in NSP1 or NSP3 also are replication-competent attenuated viruses and can be promising vaccine candidates.

Example 12: Production of Artificial Recombinant *Rotavirus* Stably Expressing a Green Fluorescent Protein An experiment was performed to examine the feasibility of the production of a recombinant rotavirus expressing a green fluorescent protein, ZsGreen.

Figure 14:
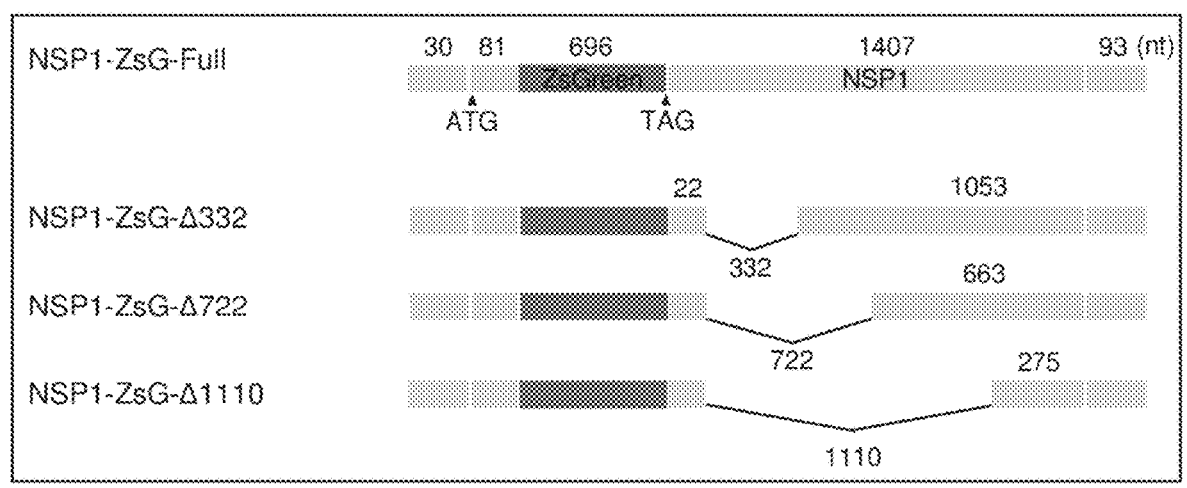
FIG. 14 shows the structures of various forms of NSP1 genes having a ZsGreen gene insertion. The 1st row shows an NSP1 gene having no base deletion, and the 2nd to 4th rows show NSP1 genes having partial base deletions.

Materials and Methods (1) Preparation of NSP1 Expression Plasmids Having a Green Fluorescent Protein Gene Insertion The ZsGreen (hereinafter referred to as ZsG) gene was used as the green fluorescent protein gene. The ZsG protein-coding region (SEQ ID NO: 33) of the pZsGreen vector (Clontech) was amplified by PCR, and the amplified product was inserted between positions 111 and 112 of the NSP1 gene (SEQ ID NO: 15) of pT7-NSP1SA11 to yield an NSP1 gene expression plasmid having a ZsG gene insertion (designated as pT7-NSP1SA11-ZsG-Full). In addition, variants of plasmid pT7-NSP1SA11-ZsG-Full, namely a plasmid having a deletion of positions 134 to 465 of the NSP1 gene, a plasmid having a deletion of positions 134 to 855 of the same gene, and a plasmid having a deletion of positions 134 to 1243 of the same gene (designated as pT7-NSP1SA11-ZsG-Δ332, pT7-NSP1SA11-ZsG-Δ722 and pT7-NSP1SA11-ZsG-Δ1110, respectively), were produced (see FIG. 14).

(2) Production of Artificial Recombinant Viruses and Confirmation of ZsG Expression ZsG-expressing rotaviruses were produced in the same manner as in Example 2 except that pT7-NSP1SA11-ZsG-Full, pT7-NSP1SA11-ZsG-Δ332, pT7-NSP1SA11-ZsG-Δ722 or pT7-NSP1SA11-ZsG-Δ1110 was used instead of pT7-NSP1SA11 in the set of the 11 RNA genome segment expression vectors prepared in Example 2 (2). The viruses produced using the different ZsG-expressing plasmids are designated as rsSA11/ZsG-Full, rsSA11/ZsG-Δ332, rsSA11/ZsG-Δ722 and rsSA11/ZsG-Δ1110. The produced viruses were separately added to infect MA104 cells, and green fluorescence (ZsG expression) was examined under a fluorescence microscope.

(3) Confirmation of Retention Rate of ZsG Gene in Serial-Passaged ZsG-Expressing Rotaviruses Confluent MA104 cells on 24-well plates were infected with rsSA11/ZsG-Full, rsSA11/ZsG-Δ332, rsSA11/ZsG-Δ722 or rsSA11/ZsG-Δ1110 at an MOI of 0.0001 and cultured in FBS-free DMEM supplemented with 0.5 μg/mL trypsin. Each virus strain was recovered from the culture supernatant harvested at 72 hours postinfection and was used as stock P1. 1 μL of virus stock P1 of each strain was separately added to infect confluent MA104 cells on 24-well plates and cultured in FBS-free DMEM supplemented with 0.5 μg/mL trypsin for 72 hours. Then, stock P2 was prepared. The same viral infection procedure was repeated to prepare virus stocks up to P10. Confluent MA104 cells on 12-well plates were infected with virus stock P1, P5 or P10 of each strain at an MOI of 0.01 and cultured in DMEM without 5% FBS. After 16 hours of infection, the cells were fixed with 10% formalin for 24 hours and then subjected to immunostaining for a viral antigen. The fixed cells were washed twice with PBS, treated with 0.1% Triton X-100 for cell permeabilization, and reacted with a rabbit anti-rotavirus NSP4 antibody and an anti-rabbit IgG antibody-Alexa 594 conjugate for viral antigen detection. The immunostained cells were observed with a fluorescence microscope, and the ZsG expression level in viral antigen-positive cells was determined.

Results

Figure 15:
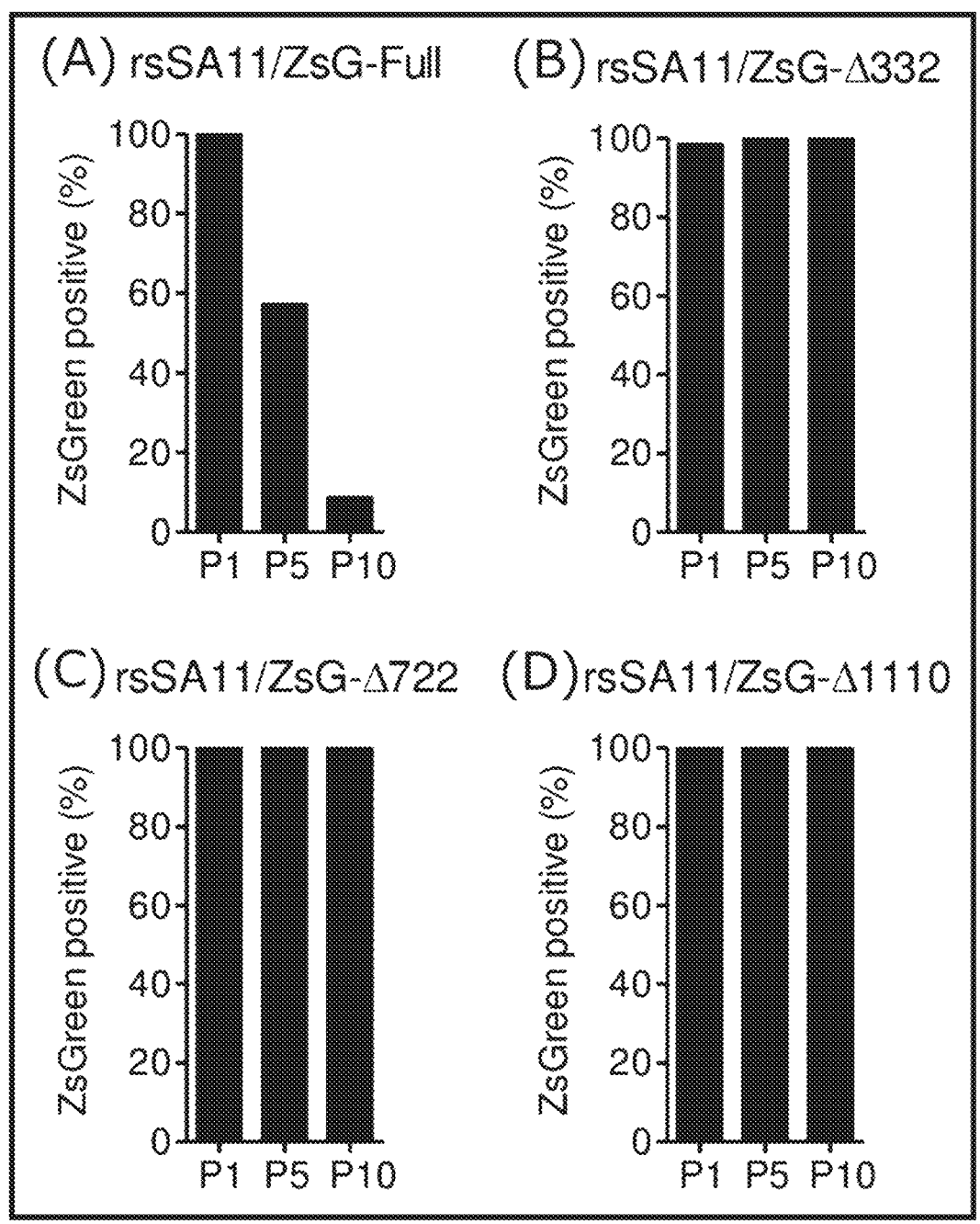
FIG. 15 shows the retention rate (ZsGreen expression level) of the ZsGreen gene after serial passage of four different ZsGreen-expressing artificial recombinant rotaviruses each produced using a genome segment expression vector containing the corresponding NSP1 gene having a ZsGreen gene insertion shown in FIG. 14.

The results are shown in FIG. 15. The ZsG expression level after infection with rsSA11/ZsG-Full was 100% for P1, 57.1% for P5 and 8.6% for P10, showing that ZsG expression decreased with repeated passage. In contrast, the ZsG expression level after infection with rsSA11/ZsG-A332, rsSA11/ZsG-A722 or rsSA11/ZsG-A1110 ranged 99 to 100% for P1, P5 and P10, showing that the 332- to 1110-base deletion of the NSP1 gene led to stable retention of the ZsG gene.

Example 13: Improvement of Mammalian *Orthoreovirus* Reverse Genetics System

An experiment was performed to examine whether co-expression with Mammalian orthoreovirus μNS and σNS, which are functionally the same as rotavirus NSP2 and NSP5, would improve the efficiency of artificial recombinant Mammalian orthoreovirus production.

Materials and Methods (1) Preparation of μNS Expression Vector and σNS Expression Vector For preparation of a μNS expression vector and a σNS expression vector, the protein-coding region DNA of the μNS gene (M3 gene in Table 1, GenBank ACCESSION: AF174382, SEQ ID NO: 6) of Mammalian orthoreovirus strain T1L and the protein-coding region DNA of the σNS gene (S3 gene in Table 1, GenBank ACCESSION: M14325, SEQ ID NO: 9) of the same strain were individually inserted into the plasmid pCAGGS shown in FIG. 10. These coding region DNAs were synthesized by custom gene synthesis services (Eurofins Genomics). These synthetic DNAs were individually inserted into the BglII restriction site of plasmid pCAGGS (between positions 1753 and 1754 of SEQ ID NO: 28) to yield pCAG-μNST1L (Mammalian orthoreovirus μNS expression vector) and pCAG-σNST1L (Mammalian orthoreovirus σNS expression vector).

(2) Production of Artificial Recombinant Virus

BHK-T7/P5 cells were seeded on 24-well culture plates at $2 \times 10^5$ cells/well on the previous day of transfection. The BHK-T7/P5 cells were transfected with 0.4 μg each of the RNA genome segment expression vectors produced in Example 1 (pT7-L1-M2T1L, pT7-L2-M3T1L, pT7-L3-S3T1L and pT7-S1-52-54-M1T1L); and 0.4 μg of the μNS expression vector (pCAG-μNST1L) and/or 0.4 μg of the σNS expression vector (pCAG-σNST1L) using a transfection reagent (TransIT-LT1 (trade name), Mirus). The transfection reagent was used in a volume of 2 μL per microgram of DNA. The BHK-T7/P5 cells were cultured in DMEM medium supplemented with 5% FBS, 100 units/mL penicillin and 100 μg/mL streptomycin in an atmosphere of 5% $CO_2$ at 37° C. The medium and the cells were harvested 48 hours after the transfection. The harvested medium and cells were repeatedly freeze-thawed 3 times and used as a virus sample for plaque assay (see Example 1), from which the viral titer was determined.

Results

As compared with the viral titer from the cells transfected with only the 4 expression vectors for the RNA genome segments of MRV T1L (pT7-L1-M2T1L, pT7-L2-M3T1L, pT7-L3-S3T1L and pT7-S1-S2-S4-M1T1L), the viral titer from the cells co-transfected with the μNS expression vector and the σNS expression vector was about 8.2 times higher. The viral titer from the cells co-transfected with only the μNS expression vector was about 6.4 times higher. These results show that co-transfection of the RNA genome segment expression vectors with the μNS expression vector only or with both the μNS expression vector and the σNS expression vector into the host cells greatly improves the efficiency of artificial recombinant virus production.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for producing an artificial recombinant virus of the family Reoviridae, the method comprising:
   (1) introducing a FAST protein expression vector into host cells;
   (2) introducing a vector containing a set of expression cassettes for individual RNA genome segments of a virus or introducing a set of single-stranded RNA transcripts of the RNA genome segments from the expression cassettes into host cells; and
   (3) culturing the host cells.

2. The method according to claim 1, wherein step (1) further comprises introducing a capping enzyme expression vector into the host cells.

3. The method according to claim 1, wherein the artificial recombinant virus has a mutation introduced in at least one of the RNA genome segments and/or a foreign gene inserted in at least one of the RNA genome segments.

4. The method according to claim 1, wherein the FAST protein is Nelson Bay reovirus p10, Avian reovirus p10, Broome reovirus p13, Reptilian reovirus p14, Baboon reovirus p15, grass carp reovirus p16 or Atlantic salmon reovirus p22.

5. The method according to claim 2, wherein the capping enzyme expression vector encodes a capping enzyme of a DNA or RNA virus which replicates in the cytoplasm of host cells.

6. The method according to claim 1, wherein the expression cassette for an RNA genome segment comprises an RNA polymerase promoter, a DNA encoding the RNA genome segment and a DNA encoding a self-cleaving ribozyme.

7. The method according to claim 6, wherein the RNA polymerase promoter is a T7 promoter, and the host cells are recombinant T7 RNA polymerase-expressing cells.

8. The method according to claim 6, wherein the ribozyme is a hepatitis D virus ribozyme.

9. The method according to claim 1, wherein the host cells are co-cultured with highly virus-susceptible cells, wherein the highly virus-susceptible cells are cells selected from the group consisting of BHK cells, MA104 cells, COS7 cells, CV1 cells, Vero cells, L929 cells, 293T cells, and A549 cells.

10. The method according to claim 1, wherein the artificial recombinant virus of the family Reoviridae is an artificial recombinant rotavirus.

11. The method according to claim 10, comprising overexpressing a rotavirus NSP2 gene product and/or a rotavirus NSP5 gene product in the host cells.

12. The method according to claim 10, wherein the artificial recombinant rotavirus expresses a foreign gene, and wherein a vector containing an expression cassette for an RNA genome segment encoding NSP1 which cassette has an insertion of the foreign gene in an NSP1 gene and a 100- to 1550-base deletion in the NSP1 gene is used instead of a vector containing an expression cassette for an RNA genome segment encoding NSP1.

13. A method for promoting viral replication, comprising infecting host cells expressing a FAST protein with a virus of the family Reoviridae and culturing the host cells.

14. The method according to claim 13, wherein the virus of the family Reoviridae is a virus of the genus *Orthoreovirus* or *Rotavirus*.

15. The method according to claim 13, wherein the FAST protein is selected from Nelson Bay reovirus p10, Avian reovirus p10, Broome reovirus p13, Reptilian reovirus p14, Baboon reovirus p15, grass carp reovirus p16 or Atlantic salmon reovirus p22.

* * * * *

SEQUENCE LISTING

<160> NUMBER OF SEQ ID NOS: 33

<210> SEQ ID NO 1
<211> LENGTH: 3854
<212> TYPE: DNA
<213> ORGANISM: Mammalian orthoreovirus

<400> SEQUENCE: 1

```
gctacacgtt ccacgacaat gtcatccatg atactgactc agtttggacc gttcattgag      60
agcatttcag gtatcactga tcaatcgaat gacgtgtttg aagatgcagc aaaagcattc     120
tctatgttta ctcgcagcga tgtctacaag gcgctggatg aaataccttt ctctgatgat     180
gcgatgcttc caatccctcc aactatatat acgaaaccat ctcacgattc atattattac     240
attgatgctc taaaccgtgt gcgtcgcaaa acatatcagg gccctgatga cgtgtacgta     300
cctaattgtt ctattgttga attgctggag ccacatgaga ctctgacatc ttatgggcgg     360
ttgtccgagg ccatcgagaa tcgtgccaag gatgggaca gccaagccag aatcgccaca      420
acgtatggta aatcgctga atctcaagct cgacagatta aggctccatt ggagaagttt      480
gtgttggcac tattagtggc cgaagcaggg gggtctttat atgatccagt tttgcagaag     540
tatgatgaga ttccagatct atcgcataat tgcccttat ggtgttttag agagatctgt      600
cgtcacatat ctggtccatt accagatcgg gcacttatc tttacttatc tgcaggggta      660
ttctggttaa tgtcaccacg aatgacgtct gcaatccctc cgctactatc cgatcttgtt     720
aatttagcta ttttgcaaca aactgcgggt ttagatccat cattagtgaa attgggagta     780
cagatatgcc ttcatgcagc agctagctca agttattcat ggtttatctt aaagactaag     840 tctattttc ctcaaaacac gttgcacagt atgtatgaat ctctagaagg gggatactgt      900
cctaatcttg aatggttaga gcctagatca gactataagt tcatgtacat gggagtcatg     960
ccattgtccg ctaagtatgc taggtcggcg ccgtccaatg ataagaaagc gcgggaactt    1020
ggcgagaaat atggactgag ctcagtcgtc ggtgagcttc gtaaacggac aaagacgtat    1080
gttaaacatg actttgcttc agtgaggtac attcgtgacg ctatggcatg tactagcggt    1140
attttcttgg taagaacacc caccgaaacg gtattgcaag aatatacgca gagtccggag    1200
attaaggttc ccattcccca gaaagactgg acaggcccaa taggtgaaat cagaattcta    1260
aaagatacaa caagttccat cgcgcgttac ttatatagaa catggtactt ggcagcggcg    1320
agaatggcgg ctcaaccacg tacgtgggat ccattgtttc aagcgattat gagatctcaa    1380
tacgtgacag ctaggggtgg atctggcgca gcactccgcg aatctttgta tgcaatcaat    1440
gtgtcgttac ctgatttcaa gggcttacca gtgaaggcag caactaagat attccaggcg    1500
gcacaattag cgaacttgcc gttctcccac acatcagtgg ctatactagc tgacacttca    1560
atgggattgc gaaatcaggt gcagaggcgg ccacgatcca ttatgccatt aaatgtgccc    1620
cagcagcagg tttcggcgcc ccatacattg acagcggatt acattaacta ccacatgaat    1680
ctatcaccca cgtctggtag tgcggtcatt gagaaggtga ttcctttagg tgtatacgct    1740
tcgagccctc ctaaccagtc gatcaacatt gacatatctg cgtgtgacgc tagtattact    1800
tgggatttct ttctgtcagt gattatggcg gctatacacg aaggtgtcgc tagtagctcc    1860
attggaaaac catttatggg ggttcctgca tccattgtaa atgatgagtc tgtcgttgga    1920
gtgagagctg ctaggccgat atcgggaatg cagaacatga ttcagcatct atcgaaacta    1980
tataaacgtg gattttcata tagagtaaac gattcttttt ctccaggtaa cgattttact    2040
catatgacta ccactttccc gtcaggttca acagccacct ctactgagca tactgctaat    2100
```

```
aatagtacga tgatggaaac tttcctgaca gtatggggac ccgaacatac tgacgaccct    2160
gacgtcttac gtttaatgaa gtctttaact attcaaagga attacgtatg tcaaggtgat    2220
gatggattaa tgattatcga tgggactact gctggtaagg tgaacagtga aactattcag    2280
aacgatctag aattaatctc aaaatatggt gaggaattcg gatggaaata tgacatagcg    2340
tacgatggga ctgccgaata cttaaagcta tacttcatat ttggctgtcg aattccaaat    2400
cttagtcgcc atccaatcgt ggggaaagaa cgggcgaatt cttcagcaga ggagccatgg    2460
ccagcaattc tagatcagat tatgggtgtc ttctttaatg gtgttcatga tgggttacag    2520
tggcagcggt ggatacgtta ttcatgggct ctatgctgtg ctttctcacg tcaaagaaca    2580
atgattggtg agagcgtggg ttaccttcaa tatcctatgt ggtcttttgt ctactgggga    2640
ttaccactgg ttaaagcgtt tgggtcagac ccatggatat tttcttggta catgcctact    2700
ggagatctgg gaatgtatag ttggattagc ttgatacgcc ctctgatgac aagatggatg    2760
gtggctaatg gttacgtaac tgacagatgc tcaaccgtat tcgggaacgc agattatcgc    2820
aggtgtttca atgaacttaa actatatcaa ggttattata tggcacaatt gcccaggaat    2880
cctaagaagt ctggacgagc ggcctctcgg gaggtaagag aacaattcac tcaggcatta    2940
tccgactatc taatgcaaaa tccagagctg aagtcacgtg tgctacgtgg tcgtagtgag    3000
tgggagaaat atggagcggg gataattcac aatcctccgt cattattcga tgtgccccat    3060
aaatggtatc agggtgcgca agaggcagca atcgctacga gagaagagct ggcagaaatg    3120
gatgagacat taatgcgcgc tcgaaggcac agctattcga gcttttcaaa gttattagag    3180
gcgtatctgc tcgtgaaatg gcgaatgtgc gaggcccgcg aaccgtcggt tgatttgcga    3240
ttaccattat gtgcgggtat tgacccatta aactcagatc cttttctcaa gatggtaagc    3300
gttggaccaa tgctccagag tacgagaaag tactttgctc agacactatt catggcaaag    3360
acggtgtcgg gtcttgacgt taacgcgatt gatagcgcgt tattacgact gcgaacatta    3420
ggtgctgata agaaagcatt aacggcgcag ttattaatgg tggggcttca ggagtcagaa    3480
gcggacgcat tggccgggaa gataatgcta caggatgtga atactgtgca attagccaga    3540
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg gaatggtaat gactgcgact    3720
ggagttgctg tcgacatcta tctggaggat atacatggcg gtggtcggtc acttggacag    3780
agattcatga cttggatgcg acaggaagga cggtcagcgt gagtctacca tgggtcgtgg    3840
tgcgtcaact catc                                                     3854
```

<210> SEQ ID NO 2
<211> LENGTH: 3915
<212> TYPE: DNA
<213> ORGANISM: Mammalian orthoreovirus

<400> SEQUENCE: 2

```
gctattggcg caatggcgaa cgtttgggga gtgagacttg cagactcttt atcatcaccc      60
actattgaga caagaactcg tcattacaca ctacgcgatt tctgttccga cctggatgct     120
gtggctggca aggaaccctg gagacctttg cgcaatcaga gaacgaatga cattgtcgcc     180
gttcaattgt ttaggccact gcagggattg gtgcttgaca cgcagttcta tggattccct     240 ggcatttttct cagaatggga gcagtttata aaggaaaaac tccgcgtatt aaaatatgag     300
```

```
gttttgcgga tctacccaat cagtaattat aatcatgaac gtgtcaatgt cttcgtagca      360
aatgctcttg tcggtgcgtt cctatccaac caagccttct atgacctgtt gcctctatta      420
gtaataaatg ataccatgat aaatgactta cttgggacag gtgccgccct ttctcaattt      480
tttcaatccc atggtgaggt tttagaagtt gccgcaggaa ggaagtacct gcaaatgaag      540
aactactcga acgatgacga tgatccacct ttgttcgcta aagatctgtc ggactatgcg      600
aaggcgtttt acagtgacac gtttgagact ctagaccgat ttttctggac acatgactca      660
tctgcgggcg tcctagtgca ctatgataag cccactaacg ggaatcatta catcttgggt      720
actctgacgc agatggttag tgcgcctccg catatcatta cgctactga cgcattgttg      780 ctcgaatcgt gcttagaaca atttgcggcg aatgtgagag ccaggccagc gcagcctgtt      840
gcgagattgg atcaatgtta tcatttacgg tggggtgctc aatatgttgg cgaggactca      900
ttgacgtacc gtttgggggt actttcgctg ctggctacca acggatatca attagctaga      960
ccgatcccta agcaattgac gaatcgatgg ctctctagtt ttgtcagtca ggtaatgtcg     1020
gatggtgtaa atgagacgcc attatggcct caagagagat atgtccaaat agcctacgat     1080
tcaccatctg tagtcgatgg agccacgcac tatggctatg ttaggcgaaa tcagttgcgg     1140
ttgggcatga gggtgtccgc tcttcagtca ttgagtgata ctccggctcc gatacagtgg     1200
ttaccgcagt atactattga acaggcagct gttgatgagg gagatctaat ggtttctcgc     1260
ttgactcaac taccattacg tcctgactat ggcagcatat gggttggtga tgccctatcg     1320
tattatgttg attacaatcg cagccataga gttgtactat catccgaact accacagcta     1380
ccagatacat actttgacgg agatgagcaa tacggtcgta gcttgttctc tctagcacga     1440
aaaattggtg atcgatctct catcaaagat acagcagtgc ttaagcatgc gtaccaggcc     1500
attgatccaa acactggaaa ggaatacctt cgcgcaggac agtccgttgc atactttggg     1560
gcatcagctg gtcattcagg ggcggatcag cctctagtaa ttgagccatg gacgcagggt     1620
aagattagtg gtgtgcctcc gccctcctca gttagacagt ttgggtatga tgttgctaaa     1680
ggtgcgatcg tagacttagc aagaccgttc ccgtcgggcg actaccaatt tgtatattct     1740
gacgtcgatc aggtcgttga tggccacgat gatctcagca tatcctcagg actggtggag     1800
agtctattag actcatgcat gcatgccaca tccccaggtg ggtcattcgt gatgaagatc     1860
aacttcccga cacgcactgt ctggcactat atagagcaga agattctccc aaatattacc     1920
tcgtacatgt tgattaaacc attcgtgact aataatgtag agttattctt tgtggctttt     1980
ggtgtgcatc aacaatcagc attgacatgg acgtctgggg tgtatttctt cctggtcgat     2040
cacttctatc gatacgagac attgtctacg atttcacgtc agttgccatc gttcggatac     2100
gttgatgatg ggtcgtctgt gacaggcatt gagatgatca gtcttgaaaa tccaggcttt     2160
tcaaacatga cccaagctgc acgtgttggg atatcagggt tgtgtgcgaa tgtcggtaat     2220
gcgcgtaaat taatatctat tcatgaatcc catggggcac gcgtgctcac catcacatca     2280
agaagatctc cagcttcggc caggcggaaa gctcgcttac gctatttgcc actcgtagac     2340
ccacgatctt tggaagtgca ggcacgtacg atactgccat ctaacccagt gttgtttgat     2400
aacgtaaacg gagcatcgcc tcactgtatgt ttgacgatga tgtataactt tgaagtgtct     2460
agtgcggtgt atgatggtga tgtagtactt gatcttggta ccggtcctga agcgaagatt     2520
ctggagctga ttcctccaac atccccggta acatgcgtag acattaggcc aacggcacag     2580
ccgagtggct gttggaacgt acgtacgact ttttctagagc ttgattactt aagtgacggt     2640
tggataacgg gtatacgtgg cgacatcgtc acttgcatgc tgtctctggg tgctgctgct     2700
```

```
gctggaaaat ccatgacgtt cgacgcggca ttccaacagc tagtgaaagt tcttactaaa    2760
agtacagcta acgtgttgtt gattcaagtc aactgcccaa cggatgtgat ccgaacaatt    2820
aagggatatt tggagataga tcaaactaat aagcggtaca gatttccaaa gtttggccgc    2880
gatgaaccgt actctgacat ggattcatta gagcgcatat gtcgggctgc atggccaaat    2940
tgttccatca cgtgggtgcc cttgtcctat gacctgcgtt ggactaagct tgctctactt    3000
gaatcgacta cactgagcag tgcatcagtg agaattgctg aattgatgta caagtacatg    3060
cccgttatga ggatagatat tcatgggtta cccatggaaa agcaaggcaa tttcatagtg    3120
ggtcagaact gctcttttgac tataccgggc ttcaacgcac aggacgtatt caattgttac    3180
ttcaactccg cgctcgcctt ctctactgag gatgttaatt ctgcaatgat accacaggtg    3240
acggctcagt tgatgctaa caaaggagag tggtcattgg acatggtgtt ctcagacgct    3300
ggtatctaca caatgcaggc attggtcggt tccaacgcaa atcctgtgtc tctgggttcg    3360
tttgtagtgg actctccgga tgtggacata acagatgcat ggcctgctca gctggacttt    3420
accatagctg gcactgacgt cgacattaca gttaatcctt attaccgctt gatggccttt    3480
gtgaggatta tggacaatg gcagattgcg aatcctgata aattccaatt tttctcatca    3540
agtacaggaa cgttagtgat gaatgtaaag ttagatatag ctgataggta cttgttatac    3600
tacattcgtg acgttcaatc tagggatgtg ggattttaca tacagcaccc attacagtta    3660
ttaaatacta ttacgctgcc tacaaatgag gacttattct tgagcgctcc tgacatgcgc    3720
gagtgggcag taaggagag tggtaatacc atatgcatac ttaatagtca aggttttgtg    3780
ccacctcagg attgggatgt tcttaccgat actattagct ggtctccttc gctcccaact    3840
tatgtggtgc ctccgggtga ttatactctg cacctctgt aactcattac ccctcgtgag    3900
cgtgcctaat tcatc                                                      3915
```

<210> SEQ ID NO 3
<211> LENGTH: 3901
<212> TYPE: DNA
<213> ORGANISM: Mammalian orthoreovirus
<400> SEQUENCE: 3

```
gctaatcgtc aggatgaagc ggattccaag gaagacaaag gcaaatcca gcggaaaggg     60 caatgactca acagaaagat cggacgatgg ctcgagccaa ttacgagaca agcaaaacaa   120
taaggctggc cctgccacta cggagcctgg cacatctaac cgagagcaat acagagcccg   180
accaggtatt gcatctgtgc agagggccac tgaaagtgca gaactgccca tgaagaataa   240
tgacgaaggg acgccagata agaaaggaaa tactaggggc gacttagtta atgagcatag   300
tgaggctaaa gacgaggcgg atgaagcgac gcagaagcag gcaaagaca cagacaaaag   360 taaagcgcaa gtcacatatt cagacactgg tatcaataat gctaatgaac tgtcaagatc   420
tgggaatgtg gataatgagg gtggaagtaa tcagaagccg atgtccacca gaatagctga   480
agcaacgtct gctatagtgt cgaaacatcc tgcgcgtgtt gggttaccac ctaccgctag   540
cagtggtcat gggtatcagt gccacgtctg ttctgcagtc ctgtttagtc ctttagacct   600
agatgcccac gtcgcctcac atggtttgca tggtaacatg acattaacat cgagtgagat   660
tcagcgacat ataactgagt tcatcagctc atggcaaaat catcctattg ttcaagtttc   720
ggctgatgtc gaaataaga agactgctca actgcttcac gctgacactc ctcgactcgt   780
cacttgggat gctggtttgt gtacttcgtt caaaatcgtc ccgattgtgc cagctcaggt   840
```

```
gccgcaggat gtactggcct atacgttttt cacctcttca tatgccatcc aatcaccgtt      900
tccagaggcg gcagtgtcta ggattgtggt gcatacgaga tgggcatcta atgttgactt      960
tgaccgagat tcgtctgtca tcatggcgcc acctacagaa acaatatcc  atttgtttaa     1020 gcagttacta aatactgaaa ccctgtctgt aagggggct  aatccgctaa tgtttagagc     1080
gaacgtgttg catatgttgc tggagttcgt attagataac ttgtatctga acagacatac     1140
gggattctct caagaccaca caccatttac tgagggtgct aatctgcgct cacttcctgg     1200
ccccgatgct gagaaatggt actcgattat gtatccaacg cgcatgggaa cgccgaatgt     1260
atcaaaaata tgtaatttcg tcgcctcttg tgtgcgaaat cggttggac  gatttgatcg     1320 agcacagatg atgaacggag ctatgtcaga gtgggtggat gtcttcgaga cttcagacgc     1380
gcttaccgtc tccattcgag gtcgatggat ggctagacta gctcgcatga acataaatcc     1440
aacagagatc gaatgggcgt tgactgaatg tgcacaagga tatgtgactg tcacaagtcc     1500
ttacgctcct agcgtaaata gattgatgcc ctatcgtatc tccaacgctg agcggcaaat     1560
atcacagata atcaggatca tgaacattgg caataacgcg acggtgatac aacctgttct     1620
gcaagatatt tcagtactcc ttcaacgcat atcaccactc caaatagatc caactattat     1680
ttccaacact atgtcaacag tctcggagtc tactactcag accctcagcc ccgcgtcctc     1740
aattttgggt aaactacgac cgagtaactc agatttctct agttttagag tcgcgttggc     1800
tggatggctt tataatggag ttgtgacgac ggtgattgat gatagttcat atccaaaaga     1860
cggtggcagc gtgacctcac ttgaaaatct gtgggatttc ttcatccttg cgcttgctct     1920
accactgaca actgaccct  gtgcacctgt gaaagcattc atgaccttag ctaacatgat     1980
ggttggtttc gagacaatcc ctatggataa tcagatctat actcaatcga gacgcgcgag     2040
tgctttctca acgcctcaca cgtggccacg atgcttcatg aatatccagt taatttctcc     2100
aatcgatgct cctatcttgc gacagtgggc tgaaattatt catagatact ggcctaaccc     2160
ttcacagatt cgttatggtg caccgaacgt tttcggctcg gcaaatttgt tcactccacc     2220
tgaggtgctg ttattgccaa tcgatcatca accagctaat gtaacaacgc caacgctgga     2280
cttcaccaat gagttgacta attggcgcgc tcgtgtctgt gagcttatga agaatcttgt     2340
tgataatcaa agatatcaac ctggatggac acaaagtcta gtctcgtcaa tgcgcggaac     2400
gctagacaaa ttgaagttga ttaaatcgat gacacccatg tatctgcaac agctggctcc     2460
ggtagagtta gcagtgatag ctcccatgtt gcctttccca cctttccagg tgccctacgt     2520
ccgtctcgat cgtgatagag ttccaacaat ggtcggagta acacgacagt cacgagatac     2580
tattactcag ccagcgctat cgctgtcgac gaccaatact actgttggcg tgccactagc     2640
tctagacgcg agggctatca ccgttgcgct gttgtcaggg aaatatccgc cggatttagt     2700
gacaaatgta tggtacgctg atgccattta tccaatgtat gcagacactg aggtgttctc     2760
taatcttcag agagacatga ttacctgcga ggccgtgcag acattagtga ctctggtggc     2820
gcaaatatca gagacccagt atcctgtaga taggtatctt gattggatcc catcactgag     2880
agcatcggcg gcgacggcgg cgacatttgc tgagtgggtt aatacttcaa tgaagacggc     2940
gtttgatttg tctgacatgc tgttagagcc tctcctaagc ggtgatccga ggatgactca     3000
actagcgatt cagtatcagc aatacaatgg cagaacgttt aatgtcatac ctgaaatgcc     3060
aggttcagtt attgctgact gcgttcaact aacagcagaa gtcttcaatc acgaatataa     3120
cctgtttggg attgcgcggg gtgatatcat cattggccgt gttcagtcga cacatttgtg     3180
gtcaccgctg gctcctccac ctgacctggt gtttgatcgt gacactcctg gtgttcacat     3240
```

| | |
|---|---:|
| cttcggacga gattgccgca tatcgtttgg aatgaatggc gccgcgccaa tgattagaga | 3300 |
| tgagactgga atgatggtgc cttttgaagg aaattggatc ttcccactgg cgctttggca | 3360 |
| aatgaataca cgatatttta atcaacaatt cgacgcgtgg attaagacag gagagttgcg | 3420 |
| aatccgtatt gagatgggcg cgtatccata tatgttgcat tactatgatc cacgtcagta | 3480 |
| cgctaatgca tggaatttaa catccgcctg gcttgaagaa attacaccga cgagcatccc | 3540 |
| atccgtgcct ttcatggtgc ccatttcaag tgatcatgac atttcctctg ccccagctgt | 3600 |
| ccaatacatc atctcgactg aatataatga tcggtcttta ttctgcacta actcatcatc | 3660 |
| tccccaaact atcgctggac cagacaaaca cattccagtt gaaagatata acattctgac | 3720 |
| caaccccgac gctccaccca cgcagataca actgcctgaa gttgttgact tgtataacgt | 3780 |
| cgtcacacgc tatgcgtatg agactccgcc tattaccgct gtcgttatgg gtgttccttg | 3840 |
| atcctcatcc tcccaacagg tgctagagca tcgcgctcga tgctagttgg gccgattcat | 3900 |
| c | 3901 |

<210> SEQ ID NO 4
<211> LENGTH: 2304
<212> TYPE: DNA
<213> ORGANISM: Mammalian orthoreovirus

<400> SEQUENCE: 4

| | |
|---|---:|
| gctattcgcg gtcatggctt acatcgcagt tcctgcggtg gtggattcac gttcaagtga | 60 |
| ggctattgga ctgctagaat cgtttggagt agacgctggg gctgatgcga atgacgtttc | 120 |
| atatcaagat catgactatg tgttggatca gttacagtat atgttagatg gatatgaggc | 180 |
| tggcgacgtt atcgatgcac tcgtccacaa gaattggtta catcactctg tctattgctt | 240 |
| gttgccaccc aaaagtcaac tactagagta ttggaaaagt aatccttcag tgataccgga | 300 |
| caacgttgat cgtcggcttc gtaaacgact aatgctaaag aaagatctca gaaaagatga | 360 |
| tgaatacaat caactagcgc gtgctttcaa gatatcggat gtctacgcac ctctcatctc | 420 |
| atccacgacg tcaccgatga caatgatcca gaacttgaat caaggcgaga tcgtgtacac | 480 |
| cacgacggac agggtaattg gggctagaat cttgttatat gctcctagaa agtactatgc | 540 |
| gtcaactcta tcatttacta tgactaagtg catcattccg tttggcaaag aggtgggtcg | 600 |
| tgttcctcac tctagattta atgttggcac atttccatca attgctaccc cgaaatgttt | 660 |
| tgtcatgagt ggggttgata ttgagtccat cccaaatgaa ttcatcaagt tgttttacca | 720 |
| gcgcgtcaag agtgttcacg ccaatatact aaatgacata tcacctcaga tcgtctctga | 780 |
| catgataaac agaaagcgtt tgcgcgttca tactccatca gatcgtcgag ccgcgcagtt | 840 |
| gatgcatttg ccctaccatg ttaaacgagg agcgtctcac gtcgacgttt acaaggtgga | 900 |
| tgttgtagac gtgttgttcg aggtagtgga tgtggccgat gggttgcgca acgtatctag | 960 |
| gaaactaact atgcataccg ttccggtatg tattcttgaa atgttgggta ttgagattgc | 1020 |
| ggactattgc attcgtcaag aggatggaat gttcacagat tggttcctac tttttaaccat | 1080 |
| gctatctgat ggcttaactg atagaaggac gcattgtcaa tacttgatta atccgtcaag | 1140 |
| tgtgcctcct gatgtgatac ttaacatctc aattactgga tttataaata ggcatacaat | 1200 |
| cgatgtcatg cctgatatat atgacttcgt taaacccatt ggcgctgtgc tgcctaaggg | 1260 |
| atcatttaaa tcaacaatta tgagagttct tgattcaata tcaatattag gagtccagat | 1320 |
| catgccgcgc gcgcatgtag ttgactcgga tgaggtgggc gagcaaatgg agcctacgtt | 1380 |

-continued

| | |
|---|---|
| tgagcatgcg gttatggaga tatacaaagg gattgctggc gttgactcgc tggatgatct | 1440 |
| catcaagtgg gtgctgaact cggatctcat tccgcatgat gacaggcttg gccaattatt | 1500 |
| tcaagcgttt ctgcctctcg caaaggactt gttagctcca atggccagaa agttttatga | 1560 |
| taactcaatg agtgagggta gattgctgac attcgctcat gccgacagtg agttgctgaa | 1620 |
| cgcaaattac tttggtcatt tattgcgact aaaaatacca tatattacag aggttaatct | 1680 |
| gatgattcgc aagaatcgtg agggtggaga gctatttcag cttgtgttat cgtatctata | 1740 |
| taaaatgtat gctactagcg cgcagcctaa atggtttgga tcattattgc gattgttaat | 1800 |
| atgtccctgg ttacatatgg agaaattaat aggagaagca gacccggcat ctacgtcggc | 1860 |
| tgaaattgga tggcatatcc ctcgtgaaca gctgatgcaa gatggatggt gtggatgtga | 1920 |
| agatggattc attccctatg ttagcatacg tgcgccaaga ctggttatgg aggagttgat | 1980 |
| ggagaagaac tggggccaat atcatgccca agttattgtc actgatcagc ttgtcgtagg | 2040 |
| cgaaccgcgg agggtatctg ccaaggctgt gatcaagggt aatcacttac cagttaagtt | 2100 |
| agtttcacga tttgcatgtt tcacattgac ggcgaagtat gagatgaggc tctcgtgcgg | 2160 |
| ccatagcact ggacgggggg ctgcatacaa tgcgagacta gctttccgat ctgacttggc | 2220 |
| gtgatccgtg acatgcgtag tgtgacacct gcccctaggt caatgggggt aggggcggg | 2280 |
| ctaagactac gtacgcgctt catc | 2304 |

<210> SEQ ID NO 5
<211> LENGTH: 2203
<212> TYPE: DNA
<213> ORGANISM: Mammalian orthoreovirus

<400> SEQUENCE: 5

| | |
|---|---|
| gctaatctgc tgaccgtcac tctgcaaaga tggggaacgc ttcctctatc gttcagacga | 60 |
| tcaacgttac tggagatggc aatgtattca aaccctcagc tgagacttca tccaccgctg | 120 |
| taccgtcact gagtctatca cctggaatgt taaatcctgg aggagtacca tggattgcga | 180 |
| ttggagatga acatccgtt acttcaccgg gtgcattgcg gcgaatgact tcgaaggata | 240 |
| tcccagagac agcaataatc aatacggata attcatcagg cgcggtgcca agtgaatcag | 300 |
| cattagtgcc ctataatgat gagccattgg tagtggtgac ggagcacgct atcgcaaact | 360 |
| tcaccaaagc cgagatggca cttgagttca atcgtgagtt cctcgataaa ttgcgcgtgc | 420 |
| tgtcagtgtc accaaaatat tccgaccttc tgacgtatgt tgattgttac gttggtgtgt | 480 |
| cggcccgtca ggccctaaat aatttccaga agcaggtgcc tgtgattaca cctactagac | 540 |
| aaacaatgta tgttgactcc atacaggcgg ccttgaaagc cttagagaaa tgggaaattg | 600 |
| atttgagagt ggctcagaca ctgttgccta caaatgtccc aattggggag gtctcttgtc | 660 |
| caatgcagtc agtagtgaaa ctattagacg atcagctgcc ggacgatagc cttatacgga | 720 |
| ggtatcctaa ggaggccgct gttgctttgg ctaaaaggaa tggagggata cagtggatgg | 780 |
| acgtatcaga aggaactgtg atgaatgagg ccgtgaatgc tgtcgcagca agtgccctgg | 840 |
| caccttccgc atcagcccca cccttagaag agaaatcgaa attgactgag caagcgatgg | 900 |
| atcttgtaac tgcagctgaa cctgagataa tcgcatctct cgtaccagtt ccagcgcccg | 960 |
| tgtttgccat tccacctaag ccagccgact ataatgtgcg tactttgaag atcgatgagg | 1020 |
| ccacatggtt acgaatgatc ccaaaaacta tgggtacgcc ttttcaaatc caagtgactg | 1080 |
| acaacacagg aactaactgg caccttaact tgagaggagg gacacgcgta gtgaacttgg | 1140 |
| atcagattgc tccgatgaga ttcgttctgg atctgggggg aaaaagctat aaggagacaa | 1200 |

```
gttgggatcc aaatggtaag aaggttgggt ttatcgtatt tcaatctaag attccttttg    1260
agctttggac cgccgcctca cagattggcc aagctacagt ggttaactat gttcagctat    1320
atgctgaaga cagctcattt accgcccagt ccatcatcgc cactacatcg ttggcttata    1380
attatgaacc tgagcaattg aataagactg accctgagat gaactattac cttttagcga    1440 cttttcataga ctcagctgct ataacaccga caaacatgac acagcctgat gtttgggatg    1500
ctctgttgac gatgtctcca ctgtccgctg agaggtgac tgtgaagggt gcggtagtaa    1560
gcgaggtggt cccagcggag ttgataggga gctatactcc agagtcacta aatgcctcac    1620
ttccgaatga cgctgctaga tgtatgatcg atagagcttc gaagatagcc gaggctataa    1680
aaattgatga tgacgccggg ccagacgaat actctcccaa ctctgtaccg atccaaggtc    1740
agcttgctat ttctcaactt gagactgggt atggtgtacg atattcaat cccaaaggaa    1800 ttctctcaaa aatcgcatct agagctatgc aggcttttat tggtgatcca agtacaatta    1860
ttacgcaggc agcaccggtg ctgtcagata agaataattg gattgcattg gcacaaggag    1920
ttaagactag tttgcgtact aaaagtttat cggcgggggt gaagacggcg gtgagtaagc    1980
tgagctcatc cgagtctatt caaaattgga ctcaaggatt cttggataag gtatcgacgc    2040
actttccagc gcctaagccc gactgtccga ccaacggaga tggcagtgaa ccgtctgctc    2100
ggcgagtgaa gcgcgactca tacgcaggag tggttaagcg tgggtataca cgctaagctg    2160
ctcgccctgg tgacacgggg ttaagggatg caggcacatc atc                      2203

<210> SEQ ID NO 6
<211> LENGTH: 2241
<212> TYPE: DNA
<213> ORGANISM: Mammalian orthoreovirus

<400> SEQUENCE: 6
gctaaagtga ccgtggtcat ggcttcattc aagggattct ccgtcaacac tgttccagtt      60
tccaaggcca aacgtgatat atcatctctt gccgctactc ctggaattcg ctcacaaccc     120
ttcactccgt ctgtagacat gtctcaatcg cgtgaattcc ttacaaaggc aattgagcaa     180
gggtctatgt ctataccgtta tcagcatgtg aatgttccaa aagttgatcg taaggttgtt     240
agtttggtag tgcgaccgtt ttcttcaggt gcttttttcta tctctggagt gatttcaccg     300
gcgcacgctt atctattgga ttgtctacct cagcttgaac aggcgatggc gtttgttgct     360
tcacctgaat cttttccaggc ttctgatgtc gcaaaacgct tgctataaa gccgggcatg     420 agccttcagg atgccatcac tgccttcatc aactttgtgt ccgcgatgct gaaaatgacg     480
gtgactcgtc aaaattttga tgtcatcgtg gctgagatcg agaggcttgc ttcaaccagc     540
gtatctgtcc gaactgaaga ggcaaaggtt gccgatgaag agctgatgct gttcgggcta     600
gatcatagag ggccacagca gcttgatatt tctaatgcta aagggataat gaaagctgca     660
gatattcagg caactcatga cgttcatttg gcaccaggcg tcgtaatat cgatcctgag     720 atctacaatg agggacggtt catgtttatg cagcacaaac cactcgcggc agatcagtcg     780
tatttcacgt tggagactgc ggattatttc aagatctacc caacatatga tgagcatgat     840
agcagaatgg ctgatcagaa gcagtcaggg ttgatattgt gcactaaaga tgaggtgttg     900
gctgagcaaa ctatttttaa gctagatgcc cctgatgata aaaccgttca tctattggat     960
cgcgacgacg atcacgttgt tgctagattt actaaggtgt ttatagaaga tgtggccccc    1020
gggcatcatg ctgcgcaaag gtctggccaa cgctctgtgc ttgatgacct atatgccaac    1080
```

-continued

| | |
|---|---|
| acccaagtgg tttcaatcac ttctgctgct ctgaagtggg tagttaaaca cggtgtgtcc | 1140 |
| gacgggattg tgaatagaaa gaatgtcaaa gtgtgtgttg gttttgaccc tttgtacact | 1200 |
| ctatctacgc ataatggagt gtctttgtgc gccctgctga tggatgaaaa actttccgtg | 1260 |
| ctgaacagcg catgtcgtat gacgctgcgt tcactaatga aaactggacg tgatgctgat | 1320 |
| gcacataggg cttttcagcg agtgctctct cagggatacg catcattaat gtgctattat | 1380 |
| caccccttcac ggaagttagc atatggtgag gtgcttttttc tagagcgatc cagtgacatg | 1440 |
| gtagacggga ttaaactaca gttggacgca tctagacagt gtcatgagtg tcccgtgttg | 1500 |
| cagcagaaag tagttgagtt ggaaaaacag attatcatgc agaagtccat tcagtcagat | 1560 |
| cctaccccaa tggcgctgca accactgtta tctcagttgc gtgaactgtc tagtgaggtc | 1620 |
| acccgactcc agatggagtt aagtcggact cagtccctga atgctcagtt ggaagcggat | 1680 |
| gctaagtcag ctcaagcatg tagtctggat atgtatttga caccacac ctgcattaat | 1740 |
| ggtcatacaa agaagatga actgcttgat gctgtacgtg tcgctccaga tgtgaggaaa | 1800 |
| gaaatcatgg aaaagagggg cgaagtgaga aggggctggt gcgaacgtat ctctaaggaa | 1860 |
| gcggctgcca aatgccaaac tgttattgat gacttgactc agatgaatgg aaagcaggca | 1920 |
| cgagagataa cagaattacg cgagtcagcc gagaattatg agaagcagat tgcggaattg | 1980 |
| gtgggcacta ttactcaaaa ccagatgacg tatcagcaag agctacaagc tttggtagcg | 2040 |
| aagaatgtgg aactggatac gatgaaccaa cgtcaggcta atcattgcg tattactccc | 2100 |
| tcccttctat cagccactcc tatcgattca gtcgacggcg ctgctgacct gattgatttc | 2160 |
| tccgttccaa ctgatgagct gtaaatgagc tgtgacgcag tgttgcccta atcccttaag | 2220 |
| ccttcccgac ccctattcat c | 2241 |

<210> SEQ ID NO 7
<211> LENGTH: 1463
<212> TYPE: DNA
<213> ORGANISM: Mammalian orthoreovirus

<400> SEQUENCE: 7

| | |
|---|---|
| gctattcgcg cctatggatg catctctcat tacagagata cggaaaatag tactccaact | 60 |
| atctgtatca agcaatggct cccagtcaaa agaaatcgag gaaatcaaga aacaagtcca | 120 |
| ggtcaacgtt gatgatatca gggctgccaa tattaaactc gacggacttg gaagacagat | 180 |
| tgctgacatc agcaatagca tctcaaccat tgagtcaaga ttgggtgaga tggataatcg | 240 |
| acttgtgggt atctcgagtc aggtcacgca attatctaac tcagttagcc agaacactca | 300 |
| gagcatatcc tcattgggtg acagaatcaa tgctgtcgaa ccacgagttg acagtctgga | 360 |
| tacggtcacg tctaatctca ctggacgaac atccactttg gaggcagatg ttggaagctt | 420 |
| acggacagaa ctagcagcgc taacaacacg ggtgacaact gaggttacaa ggttagatgg | 480 |
| tctaatcaat agtggccaga attcgattgg tgagctatcc acaagactat ccaatgtgga | 540 |
| gacgtctatg gtgacgacgg ctggacgggg actgcagaaa acggaaaca ccttgaacgt | 600 |
| cattgtaggt aatggaatgt ggtttaatag ttctaatcaa ttgcagctcg accttttcggg | 660 |
| gcaatcaaaa ggggtgggat tgtcggcac aggaatggtg gttaagattg atactaatta | 720 |
| ttttgcttac aatagtaatg gagagattac attggtgagt caaatcaatg aattgccatc | 780 |
| gcgcgtatca acactggaat cagcgaaaat cgattcagtt ttacctccat taaccgtacg | 840 |
| cgaagcgagc ggcgtacgta ccctgagctt tggttatgat acgagcgatt ttacaatcat | 900 |
| caactccgta ctgtcgttac ggtcacgttt gactcttccg acatacaggt accctctgga | 960 |

```
gctcgacaca gcaaataata gagtgcaggt ggcagatcgt tttggcatgc gcacgggtac   1020
ttggacggga caattgcaat atcagcaccc acaattgagt tggagagcaa atgtcacttt   1080
gaatttgatg aaggtggatg attggttggt gttgagcttt tctcagatga cgactaactc   1140
aataatggca gatgggaaat ttgtgattaa ttttgtgtct gggttatctt ctggatggca   1200
gacgggggat actgaaccat cgtcaactat tgatccattg tctacgacat ttgccgcggt   1260
ccaatttcta ataacggtc aacgcattga tgcgtttagg atcatgggag tatcggaatg   1320
gacggatgga gaattagaga ttaagaatta tggtggcaca tacaccggtc atactcaagt   1380
atattgggct ccgtggacga tcatgtatcc atgcaatgtg aggtgaatct agcgcgaacc   1440
ctcggcacaa ggggtcaatc atc                                           1463

<210> SEQ ID NO 8
<211> LENGTH: 1331
<212> TYPE: DNA
<213> ORGANISM: Mammalian orthoreovirus

<400> SEQUENCE: 8
gctattcgct ggtcagttat ggctcgcgct gcgttcctat tcaagactgt tggatttggt     60
ggtctgcaaa atgtgccaat taatgatgag ttatcgtcac atctacttcg agccggtaat    120
tcgccatggc agctgactca gttcttagat tggataagtc ttggaagagg attagctaca    180
tcagctcttg ttccaaccgc tggttcaaga tattatcaga tgagttgttt attgagtggt    240
accctccaga ttccatttcg tcctaatcat cgatggggag atattaggtt tctgcgtcta    300
gtgtggtcag ctcctacgct tgacggggttg gttgttgccc caccgcaggt cttagctcag    360
ccagcgttac aggcgcaggc agatcgagtg tatgattgtg atgattaccc attcttagca    420
cgtgacccga gatttaagca tcgagtgtat caacaattga gcgccgtaac tctgcttaac    480
ttgacggggt ttggtccaat ttcctatgtt cgagtagacg aggatatgtg gagtggggat    540
gtgaaccagc ttctcatgaa ctacttcggg catacgtttg cggaaattgc gtatacatta    600
tgtcaagctt cagccaatag accttgggag catgatggta cgtatgcgag atgactcaa    660 attatactgt ccttattttg gttatcatat gtcggtgtaa ttcatcagca gaacacgtac    720
cggacgttct atttccaatg caatcggcgc ggtgatgctg ctgaagtatg gattcttcc    780 tgctcattaa accactccgc ccagattaga ccgggtaatc gcagtctatt cgtcatgcca    840
acaagtccag attggaatat ggacgtcaat ttgattttaa gttcgacgtt gacagggtgc    900
ttgtgttcgg gctctcagtt accgcttatt gacaataact cagtgcctgc ggtttcgcgt    960
aacatccatg gttggactgg cagagctggc aaccagctgc atggtttcca agtgcgacga   1020
atggtgactg aattctgtga cagattaaga cgcgatggga ttatgactca agctcagcaa   1080
aatcaaattg aagcgttggc agatcaaact caacagttta agagggataa acttgaggcg   1140
tgggctaggg aagatgatca gtataatcag gctaatccga attctacgat gttccgtacg   1200
aagccattta cgaatgcgca atggggacga ggaaataccg gagcgactag tgccgcaatt   1260
gcagccctta tctaatcgtc ttggagtgag gggatccccc cacaccctc acgactgacc    1320 acacattcat c                                                         1331

<210> SEQ ID NO 9
<211> LENGTH: 1198
<212> TYPE: DNA
<213> ORGANISM: Mammalian orthoreovirus
```

<400> SEQUENCE: 9

```
gctaaagtca cgcctgttgt cgtcactatg gcttcctcac tcagggctgc gatctctaag      60
atcaagagag atgatgttgg tcagcaagtt tgtccaaatt atgtcatgct tagatcatcg     120
gtcacaacga aggtggtacg aaacgttgtt gagtatcaaa tccgtacagg tggattcttt     180
tcgtgcctag ctatgttgag accgctccag tatgctaaac gtgagcgtct gcttggacaa     240
aggaatctgg aacgcatatc gactagggac attcttcaga cacgcgattt gcactcattg     300
tgcatgccaa ctcctgacgc gccaatgtcc aatcatcagg cagccaccat gagagagctg     360
atctgcagct acttcaaggt cgaccacact gatgggttga aatatatacc catggatgag     420
agatattctc catcatcgct tgccagattg ttcactatgg gtatggctgg actacacatt     480
accactgagc cttcctacaa acgtgtgccc atcatgcact ggcagcaga tttggactgc      540
atgacgttag ctttacccta catgattaca cttgatggtg acacagtggt acctgtcgcc     600
ccaacgcttt ctgcagaaca gcttttggat gatggactta agggattagc atgcatggat     660
atctcatacg gatgtgaggt ggacgctagc aaccgatcag ctggtgatca gagcatggat     720
tcttcacgat gcatcaatga gttatattgc gaggaaacgg cagaagctat ctgtgtactc     780
aaaacatgtc ttgtgctgaa ctgtatgcaa ttcaaacttg agatggatga tttagcacac     840
aacgctactg agctggacaa gatacagatg atgataccct ttagtgaacg tgttttcaga     900
atggcttctt catttgctac cattgatgcc cagtgtttca ggttttgtgt gatgatgaag     960
gataagaatt tgaagataga catgcgtgaa acgatgagac tttggactcg atcggcgttg    1020
gacgattcag tggttacgtc atctttgagt atttcgctgg atcgaggtcg atgggtagca    1080
gctgatgcta ctgatgctag attgctggtg tttccaattc gcgtgtaatg ggtgagtgag    1140
ccgatgtggt cgccaagaca tgtgccggtg tcttggtggt gggtggcgcc taatcatc     1198
```

<210> SEQ ID NO 10
<211> LENGTH: 1196
<212> TYPE: DNA
<213> ORGANISM: Mammalian orthoreovirus

<400> SEQUENCE: 10

```
gctattttg cctcttccca acgttgtcg caatggaggt gtgcttgccc aacggtcatc       60
agatcgtgga cttgattaac aacgcttttg aaggtcgtgt atcaatctac agcgcgcaag    120
agggatggga caaaacaatc tcagcacagc cagatatgat ggtatgtggt ggtgccgtcg    180
tttgcatgca ttgtctaggt gttgttggat ctctgcaacg caagctgaag catttgcctc    240
accatagatg taatcaacag attcgtcatc aggattacgt cgatgtacag ttcgcagatc    300
gtgttactgc tcactggaag cggggtatgc tgtcctttgt tgcgcagatg cacgcgatga    360
tgaatgacgt atcaccagag gatctagacc gtgtgcgtac tgagggaggt tcactagtgg    420
agttaaactg gcttcaggtt gatccaaatt caatgtttag atcaatacac tcaagttgga    480
cagatcctct gcaggtagtg gatgatcttg acactaagct ggatcaatac tggacggccc    540
tgaatctgat gattgattca tccgacttgg tgcccaactt catgatgaga gacccatcac    600
atgcattcaa tggtgtgaga ctggagggag acgcccgcca aactcaattc tctaggactt    660
tcgattcgag atcgagttta gaatgggggtg tgatggttta cgattactct gagttagagc    720
atgatccatc gaagggccgt gcttacagga aggaattggt gacgccagca cgagacttcg    780
gtcattttgg attatcccac tactctaggg cgactacccc aatccttgga agatgccag     840
ctgtattctc gggaatgttg actgggaatt gtaaaatgta tccattcatc aaaggaacgg    900
```

-continued

| | |
|---|---|
| ctaagttaaa gacagtgcgc aagctagtgg attcagtcaa tcatgcgtgg ggcgtcgaga | 960 |
| agatcagata tgcgcttgga ccaggtggca tgacgggatg gtacgacagg actatgcagc | 1020 |
| aggcccccat tgtactaact cccgctgctc tcacaatgtt ctcagacacc accaagttcg | 1080 |
| gggatttgga ttatccggtg atgattggcg atccgtgat tcttggctaa acacccccat | 1140 |
| cttcacagcg ccgggcctga ccaacctggt gtgacgtggg acaggctcca ttcatc | 1196 |

<210> SEQ ID NO 11
<211> LENGTH: 3302
<212> TYPE: DNA
<213> ORGANISM: Rotavirus

<400> SEQUENCE: 11

| | |
|---|---|
| ggctattaaa gctgtacaat ggggaagtac aatctaatct tgtcagaata tctatcattt | 60 |
| atatataatt cacaatctgc agttcaaatt ccaatatatt actcttccaa cagtgaatta | 120 |
| gaaaatagat gtattgaatt tcattccaag tgtttagaga actcaaagaa tgggttatcg | 180 |
| ttaagaaagt tgtttgttga atataatgat gtcatagaaa atgccacatt actgtcaata | 240 |
| ctatcatatt cttacgacaa gtataacgct gttgaaagaa aattggtgaa gtatgcgaaa | 300 |
| ggcaaaccat tggaggcaga cttaacagtg aatgaattgg attatgagaa caataaaata | 360 |
| acatctgaat tatttccaac agcggaggaa tatacggact cactaatgga tccagcaatt | 420 |
| ttaacttcgc tatcatcaaa tttaaatgca gtcatgttct ggttggaaaa acatgaaaat | 480 |
| gatgtcgctg aaaaacttaa agtttataaa aggagattag acctattcac catagtagcc | 540 |
| tcaacgataa ataaatatgg cgtaccaagg cataacgcaa agtacagata tgaatacgac | 600 |
| gtaatgaaag ataaaccgta ctacttagtg acatgggcaa attcttcaat tgaaatgtta | 660 |
| atgtcagttt tctctcatga cgactatttg atagcaaaag agttaatagt gttatcatat | 720 |
| tctaatagat ctactctagc aaagttagtg tcatcaccaa tgtcgatttt ggtagccttg | 780 |
| gtggatatta atggaacatt tattacaaat gaagaattag aattggaatt ttcaaataaa | 840 |
| tatgtacgag caatagttcc ggatcaaaca tttgacgaat taaatcaaat gcttgacaat | 900 |
| atgaggaaag ctggattagt tgacatacct aagatgatac aggactggtt agttgatcgt | 960 |
| tctatcgaaa aatttccatt aatggctaag atatattcat ggtcgtttca tgttggattt | 1020 |
| agaaagcaaa aaatgctaga tgctgcgctg atcaattga aaactgagta tacagaaaat | 1080 |
| gtggacgatg aaatgtatcg ggaatataca atgttaataa gagatgaagt agttaaaatg | 1140 |
| cttgaagaac cagttaaaca tgatgatcac ttgctacgag attctgagtt agctggttta | 1200 |
| ctatcaatgt cgtcagcatc gaatggtgag tcaaggcagc taaagtttgg taggaaaaca | 1260 |
| atttttcaa ctaaaaagaa tatgcatgtc atggatgata tggctaacga agatacacg | 1320 |
| cctggtataa taccaccagt gaatgttgat aaaccaatac cattaggaag aagagatgtt | 1380 |
| ccaggaagaa ggactagaat aatattcatt ctgccatacg aatatttcat agcacagcac | 1440 |
| gctgtagttg aaaaaatgtt gatttacgca aaacatacga gagaatacgc tgaattttat | 1500 |
| tcacaatcaa accaattatt gtcatacggc gatgtaacgc gttttttgtc taataacaca | 1560 |
| atggtcttgt atacggatgt atctcagtgg gattcgtctc agcataatac acagccattt | 1620 |
| aggaaaggaa taataatggg actggacata ttagctaaca tgactaatga tgctaaagtt | 1680 |
| cttcagacat taaacttata caacaaaca caatcaatc tcatggattc atacgttcaa | 1740 |
| ataccagatg gcaacgtcat taagaaaata caatacgggg cagtagcatc aggagagaaa | 1800 |

```
caaacgaaag cagcaaattc aatagcaaat ttggcactga ttaaaacggt tttgtcacgt    1860
atttctaaca acattcatt cgcaacaaaa ataataagag ttgatggaga tgataactat    1920
gcggtgctac aatttaatac agaggtgact aagcagatga tccaagacgt atcgaacgat    1980
gtaagagaaa cttatgcacg catgaatgct aaagttaaag ctctggtatc cacagtagga    2040
atagaaattg ctaaaaggta cattgcaggt ggaaaaatat ttttcgagc tggaataaat     2100 ctacttaata tgaaaagag agggcagagt acgcagtggg atcaagcagc aattttatat    2160
tcaaattata ttgtaaatag acttagagga tttgaaactg atagggagtt tattttaact    2220
aagataatgc agatgacgtc agtcgcaatt actggatcat aagactatt tccttctgaa     2280 cgcgtattaa ctacgaattc aacatttaaa gtatttgact cggaggattt tattatagag    2340
tacggaacga ctgatgacga agtatatata caaagagcgt tcatgtcttt atcaagtcag    2400
aaatcaggaa tagccgatga gatagcggca tcatcaacat ttaaaaatta cgtcacgaga    2460
ctatctgaac agttattatt ttcaaagaat aatatagtgt ccagaggaat agctttgact    2520
gaaaaagcga aattgaattc atacgctcca atatcgcttg agaaaagacg tgcacagata    2580
tcagctttat tgactatgtt gcagaaaccg gtcaccttca aatcaagtaa aataacaata    2640
aatgacatac tcagagatat aaaaccattt tttacagtaa gtgatgcaca cttacctata    2700
caataccaaa aatttatgcc aactttgcca gataacgtac agtatataat tcaatgtata    2760
ggatccagaa cttatcaaat tgaagatgac ggttcgaagt cagccatatc tagactaata    2820
tcaaagtatt cagtttataa gccatcaatt gaagaattgt ataaagtgat ttcattgcat    2880
gaaaacgaaa tacaattata tctgatttca ttaggaatac cgaaaataga cgctgacacg    2940
tatgttggat caaagattta ttctcaagat aagtatagaa tactagaatc atacgtgtac    3000
aatttattgt ccattaatta tggatgctat caattatttg atttcaattc accggacttg    3060
gagaagctga taagaatacc atttaaggga aaaataccag ctgttacatt catattacac    3120
ttatatgcaa agctagaagt tataaactac gctataaaaa atggttcatg gataagccta    3180
ttttgcaatt acccctaaatc agaaatgata aaattatgga agaagatgtg aacatcacg    3240 tcattacgtt cgccgtacac taacgcgaac ttctttcaag attagaacgc ttagatgtga    3300
cc                                                                   3302
```

<210> SEQ ID NO 12
<211> LENGTH: 2693
<212> TYPE: DNA
<213> ORGANISM: Rotavirus

<400> SEQUENCE: 12

```
ggctattaaa ggctcaatgg cgtatcgaaa acgtggagcg cgtcgtgaga cgaatctaaa      60
acaagatgaa cgaatgcaag aaaaagaaga tagcaagaac attaataatg acagtcctaa    120
atcacaatta tcagaaaaag tattatctaa gaaagaagag ataattacag ataatcaaga    180
agaagttaag atatctgatg aggtaaaaaa atctaataaa gaagaatcga acagttgtt      240 agaagtactt aaaacaaaag aggaacatca aaagaagtt cagtatgaaa tattacaaaa     300
agtactccct acatttgaac caaaagagtc aatactcaaa aaattagaag acataaaacc    360
agaacaagca aagaaacaaa ctaaactgtt tcgaatattt gaaccgaaac aattgcctat    420
ttatagagct aatggagaaa gagagcttcg taatagatgg tattggaaat tgaaacgaga    480
tactcttcct gatggagatt atgatgttag agagtatttt ttaaatttat atgatcaagt    540
attaatggaa atgccggatt atctattact taaagatatg gctgtagaga ataaaaattc    600
```

```
aagggatgct ggcaaagtag ttgattctga acagccgca atatgcgatg ctattttca      660 agatgaagaa accgaaggtg cagtaagaag attcatagct gagatgagac aacgagttca     720
agctgatcga aatgtagtca attatccatc tatattgcat ccaattgacc atgcgtttaa     780
cgaatacttc ttacaacatc agttggtaga accattaaat aatgatatca ttttcaatta    840
cataccagag agaataagaa atgatgtcaa ctatatatta aatatggaca ggaatttacc     900
gtctactgct agatatatca gaccaaactt gctacaagat aggttaaatt tacatgataa     960
ttttgagtca ctctgggata ctataactac atctaattat attttagcaa gatctgtggt    1020
gccagaccta aaagaattag tatctactga ggcacaaatc cagaaaatgt cacaagattt    1080
gcaattggaa gctttgacaa tacaatcaga gactcagttt ttaacaggta taaactcaca    1140
agccgctaat gattgtttta aaactttgat tgctgctatg ttgagtcaga gaaccatgtc    1200
attagatttc gtaacgacaa attacatgtc acttatttca ggcatgtggt tactcactgt    1260
gattccaaat gatatgttta taagagaatc attagtagca tgtcaactag ccataataaa    1320
taccattgtt tatccggcat tcggaatgca agaatgcat tataggaatg gtgatccaca     1380
gactcccttt caaattgcag agcaacagat tcaaaatttt caggtagcta attggttaca    1440
ttttgttaat tataatcagt ttagacaagt agtgattgat ggagtgttaa atcaagtctt    1500
gaatgataat ataagaaatg gtcatgtagt caaccaatta atggaagctc tgatgcaatt    1560
atctagacaa cagtttccca caatgccagt tgattataaa agatctatac agagaggaat    1620
tttgctgctt tctaacagac ttggtcagct tgtcgattta acaagattgt tatcatacaa    1680
ttatgagaca ttaatggcat gcataacaat gaatatgcag catgttcaaa cattaacaac    1740
tgaaaaattg caattaacat cagtaacatc attatgtatg ctaattggaa atgctacggt    1800
tataccgagt ccgcaaacat tgttccatta ctataatgtg aatgtcaatt ttcattcaaa    1860
ttataatgaa agaattaatg acgcagttgc aattataact gcggcaaata gattaaattt    1920
atatcaaaag aaaatgaaat caatagttga ggactttctg aaaagattac agatatttga    1980
tgttgcgaga gtaccagatg accaaatgta tagattgaga gatagattaa gactattacc    2040
agttgaaata agaagattag atatttttaa tttgatagca atgaatatgg aacagattga    2100
acgtgcatca gataaaattg cacaaggagt tataatagca taccgagata tgcagttaga    2160
acgagatgag atgtatggtt acgtcaatat tgccagaaac ttggacggat ttcaacaaat    2220
aaatcttgaa gaattgatga gatcaggaga ttatgctcaa attactaaca tgctacttaa    2280
taatcaacca gtagctttag ttggagcgct accatttata acggattcat cagtgatttc    2340
gttaatagct aaactagatg caaccgtttt tgcacagatt gtcaaactta gaaaggtcga    2400
cacgttaaaa cccatcctat ataagataaa ttcagattct aatgactttt atttggtggc    2460
taattatgat tggattccta catctactac aaaagtgtat aaacaagttc cacaacaatt    2520
tgattttaga gcgtcaatgc atatgttaac gtctaaccta acatttaccg tatattcaga    2580
tttgcttgcg ttcgtttcag ctgatactgt tgaaccaatt aatgctgttg cttttgataa    2640
tatgcgcatc atgaacgaat tgtaaacgcc aaccccattg tggagatatg acc           2693
```

<210> SEQ ID NO 13
<211> LENGTH: 2591
<212> TYPE: DNA
<213> ORGANISM: Rotavirus

<400> SEQUENCE: 13

-continued

```
ggctattaaa gcagtaccag tagtgtgttt tacctctgat ggtgtaaaca tgaaagtact      60
agctttaaga cacagtgtgg ctcaagtgta tgcagacact caagtctacg ttcatgatga     120
tacaaaagat agttatgaaa acgcttttt aatctctaat cttacgaccc ataatatttt     180
atacttaaat tatagcatta aaacattaga aatattaaat aagtcaggaa tagctgcaat    240
tgctttacaa tcacttgaag aattattcac attaataagg tgtaatttca cttatgatta   300
tgaacttgat ataatatatt tacatgatta ttcatatttat accaataatg aaattagaac   360
agaccaacat tggataacaa aaacaaatat tgaagaatat ttactacctg gatggaaatt    420
aacatatgtt ggttataatg gaagtgaaac tagaggacta tataactttt catttaaatg    480
tcaaaacgct gcaacagatg atgatctaat aattgaatac atttattcag aagcgttgga   540
cttccaaaat tttatgttaa aaagataaa ggaaagaatg actacatcgt tgcctatagc    600
tagattatct aacagagtat ttagggataa gttattccca tcattattga agaacataa    660 gaatgtagtg aacgttggtc cgcgtaatga atctatgttt acatttttaa attatccaac   720
tataaaacaa ttttcaaatg gtgcgtattt agtaaaagat actataaaat aaaacaaga    780 acgatggtta ggtaaaagga tatctcagtt tgatattggt cagtataaaa atatgctgaa    840
tgttcttaca gcaatttatt attactataa tttatataaa agtaaaccaa ttatatatat    900
gatcggatct gctccatctt attggatata tgacgttagg cattattccg attttttctt    960 tgaacttgg gatccattgg acacaccata ttcatcaatc catcacaaag aattatttt    1020 tataaatgat gtgaagaaac tgaaggataa ctcaatattg tatattgata taagaaccga   1080
taggggcaat gctgattgga aaaaatggag aaagacagta gaagaacaaa ctattaataa    1140
tttggacata gcttatgaat atttacgaac gggtaaagcg aaggtgtgtt gtgttaagat   1200
gacagctatg gatttggaac tgccaatttc agctaaatta ctgcaccacc caactacgga   1260
aataagatca gaatttatt tattactaga tacttgggat ttaactaaca ttaggaggtt   1320
cattcctaaa ggcgtgttat attcatttat aaacaatata ataactgaaa atgtgtttat   1380
tcaacaacca tttaaagtaa aagtactgaa tgatagttat attgtagcgt tatatgcatt   1440
atcaaatgat tttaataata gatcagaagt aattaaatta attaataatc agaaacaatc   1500
tctaataact gttagaataa ataatacgtt taaggatgaa ccaaaagttg ggttcaaaaa   1560
tatctatgat tggaccttc ttccaaccga ctttgatacc aaagaagcta taattacttc    1620
atacgacggt tgtttaggac tctttggttt gtctatatcg ttagcatcaa aaccaacagg   1680
gaataatcat ttattcattt taagtggtac agataagtat tataaattgg atcaatttgc   1740
taatcacacc agtatatcga gaagatcaca ccaaattagg ttttcggaat ctgctacttc    1800
atattcaggt tatatattta gagatttgtc caataataat tttaatctaa ttggtactaa    1860
tatagagaat tcagtatcag gtcatgtata taatgcttta atttattata gatataatta    1920
ttcatttgat cttaaacgct ggatttattt acattctata gataaagttg atatagaagg    1980
aggaaagtat tatgaacacg caccaataga attaattat gcatgtagat cagcaaaaga    2040
atttgctaca ttgcaggatg acttaactgt attgagatat caaacgaaa tagagaatta    2100 tattaataca gtatatagta taacatacgc tgatgatccg aattacttta tcggaataca    2160
atttagaaat ataccatata aatatgatgt taaaataccg catttaacct tcggagtatt   2220
acatatttct gataacatgg tgccagacgt gattgcacata ctaaagataa tgaagaatga    2280
attatttaaa atggatatta cgaccagtta tacatatatg ttatcagatg gaatctacgt   2340
agcaaatgtt agtggagtat tatctacata ctttaaaatc tataacgtat tttataaaaa    2400
```

```
tcaaataact tttggccaat ccagaatgtt tattccgcac ataacattaa gcttcaataa   2460
catgagaaca gtaaggatag agactactaa attacaaatt aaatccattt atttaagaaa   2520
gattaagggt gatacagtgt ttgatatggt tgagtgagct aaaaacttaa cacactagtc   2580
atgatgtgac c                                                        2591

<210> SEQ ID NO 14
<211> LENGTH: 2362
<212> TYPE: DNA
<213> ORGANISM: Rotavirus

<400> SEQUENCE: 14
ggctataaaa tggcttcgct catttataga caattgctca cgaattctta tacagtagat     60
ttatccgatg agatacaaga gattggatca actaaatcac aaaatgtcac aattaatcct    120
ggaccatttg cgcaaacagg ttatgctcca gttaactggg gacctggaga aattaatgat    180
tctacgacag ttggaccatt gctggatggg ccttatcaac aacgacatt caatccacca     240 gtcgattatt ggatgttact ggctccaacg acacctggcg taattgttga aggtacaaat    300
aatacagata gatggttagc cacaatttta atcgagccaa atgttcagtc tgaaaataga    360
acttacacta tatttggtat tcaagaacaa ttaacggtat ccaatacttc acaagaccag    420
tggaaattta ttgatgtcgt aaaaacaact gcaaatggaa gtataggaca atatggacca    480
ttactatcca gtccgaaatt atatgcagtt atgaagcata tgaaaaatt atatacatat    540 gaaggacaga cacctaacgc taggacagca cattattcaa caacgaatta tgattctgtt    600
aacatgactg cttttttgtga cttttatata attcctagat ctgaagagtc taaatgtacg    660
gaatacatta taatggatt accaccaata caaaatacta gaaatgttgt accattatcg    720
ttgactgcta gagatgtaat acactataga gctcaagcta atgaagatat tgtgatatcc    780 aagcatcat tatggaaaga aatgcaatat aatagagata taactattag atttaaattt    840
gcaaatacaa ttataaaatc aggagggctg ggatataagt ggtcagaaat atcatttaag    900
ccagcgaatt atcaatacac atatactcgt gatggtgaag aagttaccgc acatactact    960
tgttcagtga atggcgttaa tgacttcagt tttaatggag gatatttacc aactgatttt   1020
gttgtatcta aatttgaagt aattaaagag aattcatacg tctatatcga ttactgggat   1080
gattcacaag catttcgtaa cgtggtgtat gtccgatcgt tagcagcaaa cttgaattca   1140
gttatgtgta ctggaggcag ctataatttt agtctaccag ttggacaatg gcctgtttta   1200
actgggggag cagtttcttt acattcagct ggtgtaacac tatctactca atttacagat   1260
ttcgtatcat taaattcatt aagatttaga tttagactag ctgtcgaaga accacacttt   1320
aaactgacta gaactagatt agatagattg tatggtctgc ctgctgcaga tccaaataat   1380
ggtaaagaat attatgaaat tgctggacga ttttcactta tcattagt gccatcaaat   1440 gatgactatc agactcctat agcaaactca gttactgtac gacaagattt agaaaggcag   1500
ttaggagaac taagagaaga gtttaacgct ttgtctcaag aaattgcaat gtcgcagtta   1560
atcgatttag cgcttctacc attagatatg ttctcaatgt tttctggcat taaaagtact   1620
attgatgcta caaatcaat ggctactaat gttatgaaaa aattcaaaaa gtcaggatta   1680
gcgaattcag tttcaacact gacagattct ttatcagacg cagcatcatc aatatcaaga   1740
ggttcatcta tacgttcgat tggatcttca gcatcagcat ggacggatgt atcaacacaa   1800
ataactgata tatcgtcatc agtaagttca gtttcgacac aaacgtcaac tatcagtaga   1860
```
agattgagac taaaggaaat ggcaacacaa actgagggta tgaattttga tgatatatca 1920
gcggctgttt tgaagactaa gatagataaa tcgactcaaa tatcaccaaa cacaatacct 1980
gacattgtta ctgaagcatc ggaaaaattc ataccaaata gggcttaccg cgttataaac 2040
aacgatgatg tgtttgaagc tggaattgat gggaaatttt ttgcttataa agtggataca 2100
tttgaggaaa taccatttga tgtacaaaaa ttcgctgact tagttacaga ttctccagta 2160
atatccgcta taattgattt taaaacactt aaaaatttga acgataatta cggcattact 2220
aagcaacaag catttaatct tttaagatct gacccaagag ttttacgtga attcattaat 2280
caggacaatc ctataattag aaatagaatt gaacaactga ttatgcaatg caggttgtga 2340
gtaatttcta gaggatgtga cc 2362

<210> SEQ ID NO 15
<211> LENGTH: 1610
<212> TYPE: DNA
<213> ORGANISM: Rotavirus

<400> SEQUENCE: 15
ggcttttttt tgaaaagtct tgtgttagcc atggctactt ttaaagatgc atgctttcat 60
tatcgtagat taactgcttt aaatcggaga ttatgcaaca ttggtgcaaa ttctatttgg 120
atgccagttc ctgatgcgaa aattaagggg tggtgtttag aatgttgtca aatagctgat 180
ttaacccatt gttatggttg ctcattgccg catgtttgca aatggtgtgt tcagaacaga 240
agatgcttcc ttgacaatga acctcatttg cttaagctta gaactgtgaa acatccaatt 300
accaaagaca aattacagtg tatcatagac ttgtacaata taatatttcc aattaatgat 360
aaagtaatta gaaaatttga aagaatgata aagcaaagag aatgtaggaa tcaatataaa 420
attgaatggt ataatcattt gctgctccca attacattaa atgctgctgc atttaagttt 480
gatgaaaata atctttatta tgtttttggg ttatatgaga aatcagtcag tgatatatat 540
gctccatata gaattgttaa ctttataaat gaatttgata aattattgct tgatcatatt 600
aactttacaa gaatgtccaa tctaccaata gagttgagaa accattacgc aaagaaatac 660
ttccaattat caagactgcc atcatcaaaa ctaaagcaaa tttacttttc agattttact 720
aaagaaactg tgatttttaa tacttataca aaaacgccag gaagatcaat atacagaaat 780
gtaactgaat ttaattggag agatgaattg gagctttatt ctgatttaaa aaatgataag 840
aataaattaa ttgctgcaat gatgacgagt aagtatactc ggttctatgc tcatgataat 900
aattttggaa ggttgaaaat gacaatattt gagttgggac atcattgtca gcctaactac 960
gtggcatcta atcacccagg caatgcttcc gatatccagt actgtaaatg gtgtaatata 1020
aaatattttc ttagtaaaat tgattggcgg attcgtgata tgtataattt attgatggaa 1080
tttattaagg attgttataa aagtaatgtt aacgttggac attgtagttc tgttgaaaac 1140
atatatcctt taattaaaag attaatttgg agtttgttta ctaatcacat ggatcaaaca 1200
attgaagaag tgtttaatca catgtcgcca gtgtcagttg aaggtacgaa tgtcatcatg 1260
ttgattcttg gattgaatat tagtttgtat aatgaaatta agcgcacttt gaatgtagat 1320
agcataccaa tggtacttaa tttaaatgaa ttcagtagta tagttaaatc aattagcagt 1380
aaatggtata atgttgatga attggataaa ttgccaatgt caataaaatc aacggaggaa 1440
ctgattgaaa tgaagaattc tggaacttta actgaagaat ttgagctact gatctccaac 1500
tcagaagatg acaatgagtg aaattatgtc actatctaat tatacagtat ttagccatca 1560
caagaccgtc cagactagag tagcgcctag ctggcaaaat actgtgaacc 1610

<210> SEQ ID NO 16
<211> LENGTH: 1356
<212> TYPE: DNA
<213> ORGANISM: Rotavirus

<400> SEQUENCE: 16
ggcttttaaa cgaagtcttc aacatggatg tcctatactc tttgtcaaag actcttaaag 60
acgctagaga caaaattgtc gaaggcacat tgtattctaa cgtgagtgat ctaattcaac 120
aatttaatca aatgataatt actatgaatg gaaatgaatt tcaaactgga ggaatcggta 180
atttgccaat tagaaactgg aattttaatt tcgggttact tggaacaact ttgctgaact 240
tagacgctaa ttatgttgaa acggcaagaa atacaattga ttatttcgtg gattttgtag 300
acaatgtatg catggatgag atggttagag aatcacaaag gaacggaatt gcacctcaat 360
cagactcgct aagaaagctg tcagccatta aattcaaaag aataaatttt gataattcgt 420
cggaatacat agaaaactgg aatttgcaaa atagaagaca gaggacaggt ttcacttttc 480
ataaaccaaa catttttcct tattcagcat catttacact aaatagatca caacccgctc 540
atgataattt gatgggcaca atgtggttaa acgcaggatc ggaaattcaa gtcgctggat 600
ttgactactc atgtgctatt aacgcaccag ccaatataca acaatttgag catattgtgc 660
cactccgaag agtgttaact acagctacga taactcttct accagacgcg gaaaggttta 720
gttttccaag agtgatcaat tcagctgacg gggcaactac atggtttttc aacccagtga 780
ttctcaggcc gaataacgtt gaagtggagt ttctattgaa tggacagata ataaacactt 840
atcaagcaag atttggaact atcgtagcta gaaattttga tactattaga ctatcattcc 900
agttaatgag accaccaaac atgacaccag cagtagcagt actattcccg aatgcacagc 960
cattcgaaca tcatgcaaca gtgggattga cacttagaat tgagtctgca gtttgtgagt 1020
ctgtactcgc cgatgcaagt gaaactctat tagcaaatgt aacatccgtt aggcaagagt 1080
acgcaatacc agttggacca gtctttccac caggtatgaa ctggactgat ttaatcacca 1140
attattcacc gtctagggag gacaatttgc aacgcgtatt tacagtggct tccattagaa 1200
gcatgctcat taaatgagga ccaagctaac aacttggtat ccaactttgg tgagtatgta 1260
gctatatcaa gctgtttgaa ctctgtaagt aaggatgcgt atacgcattc gctacacaga 1320
gtaatcactc agatggtata gtgagaggat gtgacc 1356

<210> SEQ ID NO 17
<211> LENGTH: 1105
<212> TYPE: DNA
<213> ORGANISM: Rotavirus

<400> SEQUENCE: 17
ggcatttaat gcttttcagt ggttgatgct caagatggag tctacgcaac agatggccgt 60
ctcaattatt aactcttctt ttgaagctgc agttgtagct gcaacctcag ctcttgagaa 120
tatgggaata gaatatgatt atcaggatat atattctaga gtaaagaata aatttgattt 180
tgtgatggac gattctggtg ttaaaaataa tctgattggt aaagcaataa ctattgatca 240
agctttgaat aataaatttg gatctgctat aagaaataga aactggcttg ctgatacttc 300
tagagcagct aaattagatg aggatgtaaa caaactaaga atgatgttat catcaaaagg 360
aattgatcaa aaaatgagag ttttaaacgc atgcttcagt gtaaaaagaa tacctggaaa 420
atcatcatct attattaaat gcacaaaatt gatgcgtgat aaattggaac gtggtgaagt 480

```
tgaagtggat gattcatttg tggatgaaaa aatggaagtg gataccattg actggaaatc    540
gcgctatgag caattggagc aaaggtttga atcattgaaa tccagggtaa atgaaaaata    600
taataattgg gtgttgaaag caagaaaaat gaatgaaaat atgcattctc ttcaaaatgt    660
catctctcaa cagcaagcac atatagctga gcttcaagtg tacaataata aactagaacg    720
tgatttgcaa aataaaattg gatcccttac ttcttcgatt gaatggtatt taagatcaat    780
ggaattagac cctgaaataa aggcagacat tgaacagcaa attaactcaa ttgatgcgat    840
aaatccattg cacgcttttg atgacttaga atcagtaata cgtaatttga tatctgatta    900
tgacaaatta ttccttatgt tcaaggatt aatacagaga tgtaattatc aatattcatt    960
tggttgcgaa taaccatttt gatacatgtt gaacaatcaa atacagtgtt agtatgttgt   1020
catctatgca taaccctcta tgagcacaat agttaaaagc taacactgtc aaaaacctaa   1080
atggctatag gggcgttatg tggcc                                        1105

<210> SEQ ID NO 18
<211> LENGTH: 1059
<212> TYPE: DNA
<213> ORGANISM: Rotavirus

<400> SEQUENCE: 18
ggcttttaaa gcgtctcagt cgccgtttga gccttgcggt gtagccatgg ctgagctagc    60
ttgcttttgc tatcctcatt tggagaatga tagctataaa tttattcctt ttaataattt   120
agctattaaa gctatgctga cagctaaagt agacaaaaag gacatggata agttttatga   180
ttcaattatt tatggaatag caccgcctcc tcaatttaag aaacggtata atactaatga   240
taattcaaga ggcatgaatt ttgaaacaat tatgtttact aaggtggcta tgttgatatg   300
tgaagctcta aattcattga aagtgacgca agcaaacgtc tctaatgtat tatcacgagt   360
agtatcaata aggcatttag aaaatttggt gatacgtaaa gaaaatccac aggatattct   420
atttcattca aaagatttac ttttgaaatc aacactgatt gctattggac agtctaaaga   480
aattgaaact acaataactg cagaaggagg agaaattgta tttcaaaacg ctgccttcac   540
catgtggaaa ctaacttatt tagaacatca attgatgcca attctggatc agaattttat   600
tgaatataaa gttacattga acgaagataa accatttca gatgttcatg ttaaagaatt   660
agtcgctgaa cttcgatggc aatataacaa gtttgctgta atcacacatg gtaagggtca   720
ttatagaatt gtaaagtatt catcagttgc taatcacgct gacagagtat atgcaacttt   780
caagagtaat gttaaaactg gagttaataa tgattttaac ctacttgatc aaagaattat   840
ttggcaaaac tggtatgcat ttacatcatc aatgaaacag ggtaatacac ttgacgtgtg    900
taaaaggttg cttttccaaa aaatgaaacc agaaaaaaat ccatttaaag ggctgtcaac    960
ggatagaaaa atggacgaag tttctcaagt tggcgtttaa ttcgctatca atttgaggat   1020
gatgatggct tagcaagaat agaaagcgct tatgtgacc                         1059

<210> SEQ ID NO 19
<211> LENGTH: 1063
<212> TYPE: DNA
<213> ORGANISM: Rotavirus

<400> SEQUENCE: 19
ggctttaaaa agagagaatt tccgtttggc tagcggttag ctccttttaa tgtatggtat    60
tgaatatacc acagttctaa cctttctgat atcgattatt ctactaaatt acatacttaa   120
atcattaact agaataatgg acttataat ttatagattt ctttttataa ttgtgatatt   180
```

```
gtcaccattt ctcagagcac aaaattatgg tattaatctt ccaatcacag gctccatgga    240
cattgcatac gctaattcaa cgcaagaaga accattcctc acttctacac tttgcctata    300
ttatccgact gaggctgcga ctgaaataaa cgataattca tggaaagaca cactgtcaca    360
actatttctt acgaaagggt ggccaactgg atccgtatat tttaaagaat atactaacat    420
tgcatcgttt tctgttgatc cgcagttgta ttgtgattat aacgtagtac taatgaaata    480
tgacgcgacg ttgcaattgg atatgtcaga acttgcggat ctaatattaa acgaatggtt    540
gtgtaatcca atggatatta ctctgtatta ttatcagcaa actgacgaag cgaataaatg    600
gatatcaatg ggctcatcat gtacaattaa agtatgtcca cttaatacac aaactcttgg    660
aattggatgc ttgacaactg atgctacaac ttttgaagaa gttgcgacag ctgaaaagtt    720
ggtaattact gacgtggttg atggcgttaa tcataagctg gatgtcacaa cagcaacgtg    780
tactattaga aactgtaaga aattgggacc aagagaaaac gtagccgtta tacaagttgg    840
tggttctgac atcctcgata taactgctga tccaactact gcaccacaga cagaacggat    900
gatgcgaatt aactggaaaa aatggtggca agttttttat actgtagtag actatgtaga    960
tcagataata caagttatgt ccaaaagatc aagatcacta aattcagcag cattttatta   1020
cagagtgtag gtataactta ggttagaatt gtatgatgtg acc                     1063
```

<210> SEQ ID NO 20
<211> LENGTH: 751
<212> TYPE: DNA
<213> ORGANISM: Rotavirus

<400> SEQUENCE: 20

```
ggcttttaaa agttctgttc cgagagagcg cgtgcggaaa gatggaaaag cttaccgacc     60
tcaattatac attgagtgta atcactctaa tgaacaatac attgcacaca atacttgagg    120
atccaggaat ggcgtatttt ccttatatag catctgtctt aacagttttg tttgcgctac    180
ataaagcatc cattccaaca atgaaaattg cattgaaaac gtcaaaatgt tcatataaag    240
tggtgaaata ttgtattgta acaattttta atacgttgtt aaaattggca ggttataaag    300
agcagataac tactaaagat gagatagaaa agcaaatgga cagagtagtc aaagaaatga    360
gacgccagct agaaatgatt gacaaattga ctacacgtga aattgaacaa gtagagttgc    420
ttaaacgcat ttacgataaa ttgacggtgc aaacgacagg tgaaatagat atgacaaaag    480
agatcaatca aaaaaacgtg agaacgctag aagaatggga aagtggaaaa aatccttatg    540
aaccaagaga agtgactgca gcaatgtaag aggttgagct gccgtcgact gtcctcggaa    600
gcggcggagt tctttacagt aagcaccatc ggacctgatg gctgactgag aagccacagt    660
cagccatatc gcgtgtggct caagccttaa tcccgtttaa ccaatccggt cagcaccgga    720
cgttaatgga aggaacggtc ttaatgtgac c                                   751
```

<210> SEQ ID NO 21
<211> LENGTH: 667
<212> TYPE: DNA
<213> ORGANISM: Rotavirus

<400> SEQUENCE: 21

```
ggcttttaaa gcgctacagt gatgtctctc agtattgacg tgacgagtct tccttctatt     60
ccttcaacta tatataagaa tgaatcgtct tcaacaacgt caactctttc tggaaaatct    120
attggtagga gtgaacagta catttcacca gatgcagaag cattcaataa atacatgctg    180
```

```
tcgaagtctc cagaggatat tggaccatct gattctgctt caaacgatcc actcaccagt    240
ttttcgatta gatcgaatgc agttaagaca aacgcagacg ctggcgtgtc tatggattca    300
tcagcacaat cacgaccttc aagtaatgtc ggatgcgatc aagtggattt ctccttaaat    360
aaaggcttaa aagtaaaagc taatttggac tcatcaatat caatatctac ggatactaaa    420
aaggagaaat caaaacaaaa ccataaaagt aggaagcact acccaagaat tgaagcagag    480
tctgattcag atgattatgt actggatgat tcagatagtg atgatggtaa atgtaagaac    540
tgtaaatata agaagaaata cttcgcatta agaatgagaa tgaaacaagt cgcaatgcaa    600
ttgattgaag atttgtaagt ctgacctggg aacacactag ggagctcccc actcccgttt    660
tgtgacc                                                             667

<210> SEQ ID NO 22
<211> LENGTH: 17
<212> TYPE: DNA
<213> ORGANISM: T7 phage

<400> SEQUENCE: 22
taatacgact cactata                                                  17

<210> SEQ ID NO 23
<211> LENGTH: 83
<212> TYPE: DNA
<213> ORGANISM: Hepatitis D virus

<400> SEQUENCE: 23
gggtcggcat ggcatctcca cctcctcgcg gtccgacctg ggcatccgaa ggaggacgtc    60
gtccactcgg atggctaagg gag                                           83

<210> SEQ ID NO 24
<211> LENGTH: 151
<212> TYPE: DNA
<213> ORGANISM: T7 phage

<400> SEQUENCE: 24
agctcaaaaa aaaggatccg gctgctaaca aagcccgaaa ggaagctgag ttggctgctg    60
ccaccgctga gcaataacta gcataacccc ttggggcctc taaacgggtc ttgaggggtt    120
ttttgctgaa aggaggaact atatccggat c                                  151

<210> SEQ ID NO 25
<211> LENGTH: 3076
<212> TYPE: DNA
<213> ORGANISM: Artificial sequence
<220> FEATURE:
<223> OTHER INFORMATION: p3E5 plasmid

<400> SEQUENCE: 25
atcgatcccg ggttaatacg actcactata gggtcggcat ggcatctcca cctcctcgcg    60
gtccgacctg ggcatccgaa ggaggacgtc gtccactcgg atggctaagg gagagctcaa    120 aaaaaggat ccggctgcta acaaagcccg aaggaagct gagttggctg ctgccaccgc    180
tgagcaataa ctagcataac cccttggggc ctctaaacgg tcttgaggg gttttttgct    240 gaaaggagga actatatccg gatcgagatc tctagagtc gacctgcagg catgcaagct    300
tgtattctat agtgtcacct aaatcgtatg tgtatgatac ataaggttat gtattaattg    360
tagccgcgtt ctaacgacaa tatgtacaag cctaattgtg tagcatctgg cttactgaag    420
cagaccctat catctctctc gtaaactgcc gtcagagtcg gtttggttgg acgaaccttc    480
```

```
tgagtttctg gtaacgccgt tccgcacccc ggaaatggtc agcgaaccaa tcagcagggt    540
catcgctagc cagatcctct acgccggacg catcgtggcc ggcatcaccg gcgccacagg    600
tgcggttgct ggcgcctata tcgccgacat caccgatggg gaagatcggg ctcgccactt    660
cgggctcatg agcgcttgtt tcggcgtggg tatggtggca ggccccgtgg ccggggggact   720 gttgggcgcc atctccttgc accattcctt gcggcggcgg tgctcaacgg cctcaaccta    780
ctactgggct gcttcctaat gcaggagtcg cataagggag agcgtcgata tggtgcactc    840
tcagtacaat ctgctctgat gccgcatagt taagccagcc ccgacacccg ccaacacccg    900
ctgacgcgcc ctgacgggct tgtctgctcc cggcatccgc ttacagacaa gctgtgaccg    960
tctccgggag ctgcatgtgt cagaggtttt caccgtcatc accgaaacgc gcgagacgaa   1020
agggcctcgt gatacgccta ttttataggt taatgtcat gataataatg gtttcttaga    1080
cgtcaggtgg cacttttcgg ggaaatgtgc gcggaacccc tatttgttta ttttctaaa    1140 tacattcaaa tatgtatccg ctcatgagac aataaccctg ataaatgctt caataatatt   1200 gaaaaggaa gagtatgagt attcaacatt tccgtgtcgc ccttattccc ttttttgcgg    1260
cattttgcct tcctgttttt gctcacccag aaacgctggt gaaagtaaaa gatgctgaag   1320
atcagttggg tgcacgagtg ggttacatcg aactggatct caacagcggt aagatccttg    1380
agagttttcg ccccgaagaa cgttttccaa tgatgagcac ttttaaagtt ctgctatgtg    1440
gcgcggtatt atcccgtatt gacgccgggc aagagcaact cggtcgccgc atacactatt    1500
ctcagaatga cttggttgag tactcaccag tcacagaaaa gcatcttacg gatggcatga    1560
cagtaagaga attatgcagt gctgccataa ccatgagtga taacactgcg ccaacttac    1620 ttctgacaac gatcggagga ccgaaggagc taaccgcttt tttgcacaac atggggggatc   1680 atgtaactcg ccttgatcgt tgggaaccgg agctgaatga agccatacca aacgacgagc   1740
gtgacaccac gatgcctgta gcaatggcaa caacgttgcg caaactatta actggcgaac    1800
tacttactct agcttcccgg caacaattaa tagactggat ggaggcggat aaagttgcag   1860
gaccacttct gcgctcggcc cttccggctg gctggtttat tgctgataaa tctggagccg   1920
gtgagcgtgg gtctcgcggt atcattgcag cactggggcc agatggtaag ccctcccgta   1980
tcgtagttat ctacacgacg gggagtcagg caactatgga tgaacgaaat agacagatcg   2040
ctgagatagg tgcctcactg attaagcatt ggtaactgtc agaccaagtt tactcatata    2100
tactttagat tgatttaaaa cttcattttt aatttaaaag gatctaggtg aagatccttt   2160
ttgataatct catgaccaaa atcccttaac gtgagttttc gttccactga gcgtcagacc   2220
ccgtagaaaa gatcaaagga tcttcttgag atccttttttt tctgcgcgta atctgctgct   2280
tgcaaacaaa aaaaccaccg ctaccagcgg tggtttgttt gccggatcaa gagctaccaa   2340
ctctttttcc gaaggtaact ggcttcagca gagcgcagat accaaatact gtccttctag   2400
tgtagccgta gttaggccac cacttcaaga actctgtagc accgcctaca tacctcgctc   2460
tgctaatcct gttaccagtg gctgctgcca gtggcgataa gtcgtgtctt accgggttgg   2520
actcaagacg atagttaccg gataaggcgc agcggtcggg ctgaacgggg gttcgtgca    2580 cacagcccag cttggagcga acgacctaca ccgaactgag atacctacag cgtgagctat   2640
gagaaagcgc cacgcttccc gaagggagaa aggcggacag gtatccggta agcggcaggg   2700
tcggaacagg agagcgcacg agggagcttc caggggggaaa cgcctggtat ctttatagtc   2760
ctgtcgggtt tcgccacctc tgacttgagc gtcgattttt gtgatgctcg tcaggggggc   2820
```

```
ggagcctatg gaaaaacgcc agcaacgcgg ccttttttacg gttcctggcc ttttgctggc    2880
cttttgctca catgttcttt cctgcgttat cccctgattc tgtggataac cgtattaccg    2940
cctttgagtg agctgatacc gctcgccgca gccgaacgac cgagcgcagc gagtcagtga    3000
gcgaggaagc ggaagagcgc ccaatacgca aaccgcctct ccccgcgcgt tggccgattc    3060
attaatgcag ggggat                                                   3076

<210> SEQ ID NO 26
<211> LENGTH: 288
<212> TYPE: DNA
<213> ORGANISM: Nelson bay reovirus

<400> SEQUENCE: 26
atgagcggtg attgcgctgg tctggtttca gtgtttggga gtgttcactg tcagtcgtct     60
aagaataaag ccggtgggga tctgcaagcg acttctgttc taaccacata ttggccgcat    120
cttgcgattg gtggcagtat catcttgatc atcctcctgc tgggtctatt ttactgttgt    180
tatctcaagt ggaagacgtc acatattcgt cgtacttatc acaaggagtt ggtggcgcta    240
actcgcggct atgtcaggcc gatcccggcg acgttacca gtgtctga                 288

<210> SEQ ID NO 27
<211> LENGTH: 297
<212> TYPE: DNA
<213> ORGANISM: Avian reovirus

<400> SEQUENCE: 27
atgctgcgta tgcctcccgg ttcgtgtaac ggtgcgactg ctgtatttgg taacgttcat     60
tgtcaggcag ctcaaaacac ggcaggtggt gatttgcaag ctacgtcatc cataattgca    120
tattggcctt atctagcggc gggtggtggt ttcttattaa ttgttatcat tttcgctctt    180
ctatactgtt gtaaggctaa ggtcaaggcg acgctgcac gtagtgtctt ccatcgtgag    240
ctggtagcgt tgagttctgg taagcacaat gcaatggctc cgccatacga cgtttga     297

<210> SEQ ID NO 28
<211> LENGTH: 5699
<212> TYPE: DNA
<213> ORGANISM: Artificial sequence
<220> FEATURE:
<223> OTHER INFORMATION: pCAGPM plasmid

<400> SEQUENCE: 28
gtcgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420 atctccccc cctccccacc cccaattttg tatttattta ttttttaatt attttgtgca    480
gcgatggggg cggggggggg ggggcgcgc gccaggcggg gcggggcggg gcgaggggcg    540
gggcggggcg aggcggagag gtgcggcgg agccaatcag agcggcgcgc tccgaaagtt    600
tccttttatg gcgaggcggc ggcggcggcg ccctataaaa agcgaagcg cggcggcggc    660 gggagtcgct gcgttgcctt cgccccgtgc cccgctccgc gccgcctcgc gccgcccgcc    720
```

```
ccggctctga ctgaccgcgt tactcccaca ggtgagcggg cgggacggcc cttctcctcc      780
gggctgtaat tagcgcttgg tttaatgacg gctcgtttct tttctgtggc tgcgtgaaag      840
ccttaaaggg ctccgggagg gcccttgtg cggggggag cggctcgggg ggtgcgtgcg        900
tgtgtgtgtg cgtggggagc gccgcgtgcg gcccgcgctg cccggcggct gtgagcgctg      960
cgggcgcggc gcgggctttt gtgcgctccg cgtgtgcgcg aggggagcgc ggccgggggc     1020
ggtgccccgc ggtgcggggg ggctgcgagg ggaacaaagg ctgcgtgcgg ggtgtgtgcg     1080
tgggggggtg agcaggggt gtgggcgcgg cggtcgggct gtaaccccc cctgcacccc      1140 cctccccgag ttgctgagca cggcccggct tcgggtgcgg ggctccgtgc ggggcgtggc     1200
gcggggctcg ccgtgccggg cggggggtgg cggcaggtgg gggtgccggg cggggcgggg     1260
ccgcctcggg ccgggaggg ctcggggag gggcgcggcg gccccggagc gccggcggct     1320
gtcgaggcgc ggcgagccgc agccattgcc tttttatggta atcgtgcgag agggcgcagg   1380
gacttccttt gtcccaaatc tggcggagcc gaaatctggg aggcgccgcc gcacccctc     1440 tagcgggcgc gggcgaagcg gtgcggcgcc ggcaggaagg aaatgggcgg ggagggcctt    1500
cgtgcgtcgc cgcgccgccg tccccttctc catctccagc ctcggggctg ccgcaggggg   1560
acggctgcct tcgggggga cggggcaggg cggggttcgg cttctggcgt gtgaccggcg    1620
gctctagagc ctctgctaac catgttcatg ccttcttctt tttcctacag ctcctgggca   1680
acgtgctggt tgttgtgctg tctcatcatt ttggcaaaga attcgaagat cttaagatat   1740
cggcgcgccg tttaaactta attaattcac tcctcaggtg caggctgcct atcagaaggt   1800
ggtggctggt gtggccaatg ccctggctca caaataccac tgagatcgat cttttttccct  1860 ctgccaaaaa ttatgggac atcatgaagc cccttgagca tctgacttct ggctaataaa    1920
ggaaatttat tttcattgca atagtgtgtt ggaattttt gtgtctctca ctcggaagga    1980
catatgggag gcaaatcat ttaaaacatc agaatgagta tttggtttag agtttggcaa    2040
catatgccat atgctggctg ccatgaacaa aggtggctat aaagaggtca tcagtatatg    2100
aaacagcccc ctgctgtcca ttccttattc catagaaaag ccttgacttg aggttagatt     2160 tttttatat tttgttttgt gttattttttt tctttaacat ccctaaaatt ttccttacat    2220
gttttactag ccagattttt cctcctctcc tgactactcc cagtcatagc tgtccctctt    2280
ctcttatgaa gatccctcga cctgcagccc aagctctgtg gaatgtgtgt cagttaggggt  2340 gtggaaagtc cccaggctcc ccagcaggca gaagtatgca aagcatgcat ctcaattagt    2400
cagcaaccag gtgtggaaag tccccaggct ccccagcagg cagaagtatg caaagcatgc    2460
atctcaatta gtcagcaacc atagtcccgc ccctaactcc gcccatcccg ccctaactc    2520 cgcccagttc cgcccattct ccgccccatg gctgactaat ttttttttatt tatgcagagg    2580 ccgaggccgc ctcggcctct gagctattcc agaagtagtg aggaggcttt tttggaggcc    2640
taggcttttg caaaaagctt gcatgcctgc aggtcggccg ccacgaccgg tgccgccacc   2700
atcccctgac ccacgcccct gaccctcac aaggagacga ccttccatga ccgagtacaa    2760
gcccacggtg cgcctcgcca cccgcgacga cgtccccgg gccgtacgca ccctcgccgc    2820
cgcgttcgcc gactaccccg ccacgcgcca ccgtcgac ccggaccgcc acatcgagcg     2880
ggtcaccgag ctgcaagaac tcttcctcac gcgcgtcggg ctcgacatcg caaggtgtg    2940 ggtcgcggac gacggcgccg cggtggcggt ctggaccacg ccgagagcg tcgaagcggg   3000 ggcggtgttc gccgagatcg gcccgcgcat ggccgagttg agcggttccc ggctggccgc   3060
```

-continued

```
gcagcaacag atggaaggcc tcctggcgcc gcaccggccc aaggagcccg cgtggttcct    3120
ggccaccgtc ggcgtctcgc ccgaccacca gggcaagggt ctgggcagcg ccgtcgtgct    3180
ccccggagtg gaggcggccg agcgcgccgg ggtgcccgcc ttcctggaga cctccgcgcc    3240
ccgcaacctc cccttctacg agcggctcgg cttcaccgtc accgccgacg tcgaggtgcc    3300
cgaaggaccg cgcacctggt gcatgacccg caagcccggt gcctgacgcc cgccccacga    3360
cccgcagcgc ccgaccgaaa ggagcgcacg accccatggc tccgaccgaa gccgacccgg    3420
gcggccccgc cgaccccgca cccgccccg aggcccaccg actctagagg atcataatca     3480
gccataccac atttgtagag gttttacttg ctttaaaaaa cctcccacac ctcccctga    3540 acctgaaaca taaaatgaat gcaattgttg ttgttaactt gtttattgca gcttataatg    3600
gttacaaata aagcaatagc atcacaaatt tcacaaataa agcatttttt tcactgcatt    3660
ctagttgtgg tttgtccaaa ctcatcaatg tatcttatca tgtctggatc cgctgcatta    3720
atgaatcggc caacgcgcgg ggagaggcgg tttgcgtatt gggcgctctt ccgcttcctc    3780
gctcactgac tcgctgcgct cggtcgttcg gctgcggcga gcggtatcag ctcactcaaa    3840
ggcggtaata cggttatcca cagaatcagg ggataacgca ggaaagaaca tgtgagcaaa    3900
aggccagcaa aaggccagga accgtaaaaa ggccgcgttg ctggcgtttt tccataggct    3960
ccgcccccct gacgagcatc acaaaaatcg acgctcaagt cagaggtggc gaaacccgac    4020
aggactataa agataccagg cgtttccccc tggaagctcc ctcgtgcgct ctcctgttcc    4080
gaccctgccg cttaccggat acctgtccgc ctttctccct tcgggaagcg tggcgctttc    4140
tcaatgctca cgctgtaggt atctcagttc ggtgtaggtc gttcgctcca agctgggctg    4200
tgtgcacgaa ccccccgttc agcccgaccg ctgcgcctta tccggtaact atcgtcttga    4260
gtccaacccg gtaagacacg acttatcgcc actggcagca gccactggta acaggattag    4320
cagagcgagg tatgtaggcg gtgctacaga gttcttgaag tggtggccta actacggcta    4380
cactagaagg acagtatttg gtatctgcgc tctgctgaag ccagttacct tcggaaaaag    4440
agttggtagc tcttgatccg gcaaacaaac caccgctggt agcggtggtt ttttgtttg    4500 caagcagcag attacgcgca gaaaaaaagg atcctttga tcttttctac                4560 ggggtctgac gctcagtgga acgaaaactc acgttaaggg attttggtca tgagattatc    4620
aaaaaggatc ttcacctaga tccttttaaa ttaaaaatga gttttaaat caatctaaag     4680 tatatatgag taaacttggt ctgacagtta ccaatgctta atcagtgagg cacctatctc    4740
agcgatctgt ctatttcgtt catccatagt tgcctgactc cccgtcgtgt agataactac    4800
gatacgggag ggcttaccat ctggccccag tgctgcaatg ataccgcgag acccacgctc    4860
accggctcca gatttatcag caataaacca gccagccgga agggccgagc gcagaagtgg    4920
tcctgcaact ttatccgcct ccatccagtc tattaattgt tgccgggaag ctagagtaag    4980
tagttcgcca gttaatagtt tgcgcaacgt tgttgccatt gctacaggca tcgtggtgtc    5040
acgctcgtcg tttggtatgg cttcattcag ctccggttcc caacgatcaa ggcgagttac    5100
atgatccccc atgttgtgca aaaaagcggt tagctccttc ggtcctccga tcgttgtcag    5160
aagtaagttg gccgcagtgt tatcactcat ggttatggca gcactgcata attctcttac    5220
tgtcatgcca tccgtaagat gcttttctgt gactggtgag tactcaacca agtcattctg    5280
agaatagtgt atgcggcgac cgagttgctc ttgcccggcg tcaatacggg ataataccgc    5340
gccacatagc agaactttaa aagtgctcat cattggaaaa cgttcttcgg ggcgaaaact    5400
ctcaaggatc ttaccgctgt tgagatccag ttcgatgtaa cccactcgtg cacccaactg    5460
```

-continued

| | |
|---|---|
| atcttcagca tcttttactt tcaccagcgt ttctgggtga gcaaaaacag gaaggcaaaa | 5520 |
| tgccgcaaaa aagggaataa gggcgacacg gaaatgttga atactcatac tcttcctttt | 5580 |
| tcaatattat tgaagcattt atcagggtta ttgtctcatg agcggataca tatttgaatg | 5640 |
| tatttagaaa aataaacaaa tagggttcc gcgcacattt ccccgaaaag tgccacctg | 5699 |

<210> SEQ ID NO 29
<211> LENGTH: 2535
<212> TYPE: DNA
<213> ORGANISM: Vaccinia virus

<400> SEQUENCE: 29

| | |
|---|---|
| atggatgcca acgtagtatc atcttctact attgcgacgt atatagacgc tttagcgaag | 60 |
| aatgcttcgg aattagaaca gaggtctacc gcatacgaaa taataatga attggaacta | 120 |
| gtatttatta agccgccatt gattactttg acaaatgtag tgaatatctc tacgattcag | 180 |
| gaatcgttta ttcgatttac cgttactaat aaggaaggtg ttaaaattag aactaagatt | 240 |
| ccattatcta aggtacatgg tctagatgta aaaaatgtac agttagtaga tgctatagat | 300 |
| aacatagttt gggaaaagaa atcattagtg acggaaaatc gtcttcacaa agaatgcttg | 360 |
| ttgagactat cgacagagga acgtcatata tttttggatt acaagaaata tggatcctct | 420 |
| atccgactag aattagtcaa tcttattcaa gcaaaaacaa aaaactttac gatagacttt | 480 |
| aagctaaaat attttctagg atccggtgcc cagtctaaaa gttctttatt acacgctatt | 540 |
| aatcatccaa agtcaaggcc taatacatct ctggaaatag aatttacacc tagagacaat | 600 |
| gaaacagttc catatgatga actaataaag gaattgacga ctctctcgcg tcatatattt | 660 |
| atggcttctc cagagaatgt aattctttct ccgcctatta acgcgcctat aaaaaccttt | 720 |
| atgttgccta acaagatat agtaggtttg gatctggaaa atctatatgc cgtaactaag | 780 |
| actgacggca ttcctataac tatcagagtt acatcaaacg ggttgtattg ttatttaca | 840 |
| catcttggtt atattattag atatcctgtt aagagaataa tagattccga agtagtagtc | 900 |
| tttggtgagg cagttaagga taagaactgg accgtatatc tcattaagct aatagagcct | 960 |
| gtgaatgcaa tcaatgatag actagaagaa agtaagtatg ttgaatctaa actagtggat | 1020 |
| atttgtgatc ggatagtatt caagtcaaag aaatacgaag gtccgtttac tacaactagt | 1080 |
| gaagtcgtcg atatgttatc tacatatta ccaaagcaac cagaaggtgt tattctgttc | 1140 |
| tattcaaagg gacctaaatc taacattgat tttaaaatta aaaggaaaa tactatagac | 1200 |
| caaactgcaa atgtagtatt taggtacatg tccagtgaac caattatctt tggagagtcg | 1260 |
| tctatctttg tagagtataa gaaatttagc aacgataaag gctttcctaa agaatatggt | 1320 |
| tctggtaaga ttgtgttata taacggcgtt aattatctaa ataatatcta ttgtttggaa | 1380 |
| tatattaata cacataatga agtgggtatt aagtccgtgg ttgtacctat taagtttata | 1440 |
| gcagaattct tagttaatgg agaaatactt aaacctagaa ttgataaaac catgaaatat | 1500 |
| attaactcag aagattatta tggaaatcaa cataatatca tagtcgaaca tttaagagat | 1560 |
| caaagcatca aaataggaga tatctttaac gaggataaac tatcggatgt gggacatcaa | 1620 |
| tacgccaata tgataaatt tagattaaat ccagaagtta gttatttac gaataaacga | 1680 |
| actagaggac cgttgggaat tttatcaaac tacgtcaaga ctcttcttat ttctatgtat | 1740 |
| tgttccaaaa catttttaga cgattccaac aaacgaaagg tattggcgat tgattttgga | 1800 |
| aacggtgctg acctggaaaa atactttat ggagagattg cgttattggt agcgacggat | 1860 |

| | |
|---|---|
| ccggatgctg atgctatagc tagaggaaat gaaagataca acaaattaaa ctctggaatt | 1920 |
| aaaaccaagt actacaaatt tgactacatt caggaaacta ttcgatccga tacatttgtc | 1980 |
| tctagtgtca gagaagtatt ctattttgga aagtttaata tcatcgactg cagtttgct | 2040 |
| atccattatt cttttcatcc gagacattat gctaccgtca tgaataactt atccgaacta | 2100 |
| actgcttctg gaggcaaggt attaatcact accatggacg gagacaaatt atcaaaatta | 2160 |
| acagataaaa agacttttat aattcataag aatttaccta gtagcgaaaa ctatatgtct | 2220 |
| gtagaaaaaa tagctgatga tagaatagtg gtatataatc catcaacaat gtctactcca | 2280 |
| atgactgaat acattatcaa aaagaacgat atagtcagag tgtttaacga atacggatt | 2340 |
| gttcttgtag ataacgttga tttcgctaca attatagaac gaagtaaaaa gtttattaat | 2400 |
| ggcgcatcta caatggaaga tagaccatct acaagaaact ttttcgaact aaatagagga | 2460 |
| gccattaaat gtgaaggttt agatgtcgaa gacttactta gttactatgt tgtttatgtc | 2520 |
| ttttctaagc ggtaa | 2535 |

<210> SEQ ID NO 30
<211> LENGTH: 864
<212> TYPE: DNA
<213> ORGANISM: Vaccinia virus

<400> SEQUENCE: 30

| | |
|---|---|
| atggatgaaa ttgtaaaaaa tatccgggag ggaacgcatg tccttcttcc attttatgaa | 60 |
| acattgccag aacttaatct gtctctaggt aaaagcccat acctagtct ggaatacgga | 120 |
| gctaattact ttcttcagat ttctagagtt aatgatctaa atagaatgcc gaccgacatg | 180 |
| ttaaaacttt ttacacatga tatcatgtta ccagaaagcg atctagataa agtctatgaa | 240 |
| attttaaaga ttaatagcgt aaagtattat gggaggagta ctaaagcgga cgccgtagtt | 300 |
| gccgacctca gcgcacgcaa taaactgttc aaacgtgaac gagatgctat taaatctaat | 360 |
| aatcatctca ctgaaaacaa tctatacatt agcgattata agatgttaac cttcgacgtg | 420 |
| tttcgaccat tatttgattt tgtaaacgaa aatattgta ttattaaact tccaacttta | 480 |
| ttcggtagag gtgtaatcga tactatgaga atatattgta gtctctttaa aaatgttaga | 540 |
| ctgctaaaat gcgtaagcga tagctggtta aaagatagcg ccattatggt ggctagtgat | 600 |
| gtttgtaaaa aaaatttgga tttatttatg tctcatgtta agtccgtcac taagtcttct | 660 |
| tcttggaagg atgtgaacag tgttcaattt agtattttaa acaatccagt ggatacggaa | 720 |
| ttcattaata agttcttaga gttttcgaat agagtatacg aagctctcta ttacgttcac | 780 |
| tcgttgcttt attctagtat gacttctgat tcaaaaagta tcgaaaacaa acatcagaga | 840 |
| agactagtta aactactgct gtga | 864 |

<210> SEQ ID NO 31
<211> LENGTH: 516
<212> TYPE: DNA
<213> ORGANISM: Oplophorus gracilirostris

<400> SEQUENCE: 31

| | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |

-continued

```
atcgacgggg ttacgccgaa catgatcgac tatttcggac ggccgtatga aggcatcgcc    360
gtgttcgacg gcaaaaagat cactgtaaca gggaccctgt ggaacggcaa caaaattatc    420
gacgagcgcc tgatcaaccc cgacggctcc ctgctgttcc gagtaaccat caacggagtg    480
accggctggc ggctgtgcga acgcattctg gcgtaa                              516
```

<210> SEQ ID NO 32
<211> LENGTH: 750
<212> TYPE: DNA
<213> ORGANISM: Rotavirus

<400> SEQUENCE: 32

```
ggcttttaaa agttctgttc cgagagagcg cgtgcggaaa gatggataag cttgccgacc     60
tcaactacac attgagtgta atcactctaa tgaatgacac attgcattct ataattcagg    120
atcctggaat ggcgtatttt acatatattg catctgttct aacagttttg ttcacattac    180
ataaagcttc aattccaacc atgaaaatag cattgaaaac atcaaaatgt tcatataaag    240 tgattaaaata ttgtatagtc acgatcatta atactctttt aagattggct ggatataaag    300
agcaggttac tactaaagac gaaattgagc aacagatgga tagaattgtt aaagagatga    360
gacgtcagct ggagatgatt gataaactaa ctactcgtga aattgaacag gttgaattgc    420
ttaaaagtat acatgacaac ttgataacta gatcagttga cgttatagat atgtcgaagg    480
aattcaatca gaaaaacatc aaaacgctag atgaatggga gagtggaagg aatccatatg    540
aaccgtcaga ggtgactgca tccatgtgag aggttgagtt accgtcgtct gtcttcggaa    600
gcggcggaac tcttcaccgc aagccccatt agacctgatg attgactgag aagccacagt    660
caatcatatc gcgtgtggct cagccttaat cccgtttaac caatccagcg agtgttggac    720
gttaatggaa ggaatggtct tagtgtgacc                                     750
```

<210> SEQ ID NO 33
<211> LENGTH: 696
<212> TYPE: DNA
<213> ORGANISM: Zoanthus sp.

<400> SEQUENCE: 33

```
atggctcagt caaagcacgg tctaacaaaa gaaatgacaa tgaaataccg tatggaaggg     60
tgcgtcgatg gacataaatt tgtgatcacg ggagagggca ttggatatcc gttcaagggg    120
aaacaggcta ttaatctgtg tgtggtcgaa ggtggaccat tgccatttgc cgaagacata    180
ttgtcagctg cctttatgta cggaaacagg gttttcactg aatatcctca agacatagct    240
gactatttca gaactcgtgt cctgctggt tatacatggg acaggtcttt tctctttgag     300
gatggagcag tttgcatatg taatgcagat ataacagtga tgttgaaga aaactgcatg     360 tatcatgagt ccaaattta tggagtgaat tttcctgctg atggacctgt gatgaaaaag    420
atgacagata actgggagcc atcctgcgag aagatcatac cagtacctaa gcaggggata    480
ttgaaggggg atgtctccat gtacctcctt ctgaaggatg gtgggcgttt acggtgccaa    540
ttcgacacag tttacaaagc aaagtctgtg ccaagaaaga tgccggactg gcacttcatc    600
cagcataagc tcacccgtga agaccgcagc gatgctaaga atcagaaatg gcatctgaca    660
gaacatgcta ttgcatccgg atctgcattg ccctga                              696
```